US006238889B1

(12) United States Patent
Dorssers et al.

(10) Patent No.: US 6,238,889 B1
(45) Date of Patent: May 29, 2001

(54) MOLECULAR CLONING AND EXPRESSION OF THE PRO[8] ISOFORM OF HUMAN IL-3

(75) Inventors: Lambertus Christian Johannes Dorssers, Randwijk; Gerard Wagemaker, Den Haag; Yvonne Johanna Vos, Capelle a/d IJssel; Robert Willem Van Leen, Nijmegen, all of (NL)

(73) Assignee: DSM N.V. (NL)

( * ) Notice: Subject to any disclaimer, the term of this patent is extended or adjusted under 35 U.S.C. 154(b) by 0 days.

(21) Appl. No.: 08/470,369

(22) Filed: Jun. 6, 1995

Related U.S. Application Data

(62) Continuation of application No. 08/321,480, filed on Oct. 11, 1994, now abandoned, which is a continuation of application No. 07/854,297, filed on Mar. 19, 1992, now abandoned, which is a continuation of application No. 07/249,184, filed as application No. PCT/NL87/00037 on Dec. 16, 1987, now abandoned.

(30) Foreign Application Priority Data

| | | |
|---|---|---|
| Dec. 16, 1986 | (NL) | 86202285 |
| Jul. 13, 1987 | (NL) | 87201322 |

(51) Int. Cl.[7] .......................... C12N 15/24; C07K 14/54; A61K 38/20

(52) U.S. Cl. .................................. 435/69.52; 435/320.1; 435/325; 435/348; 435/354; 435/365.1; 435/252.3; 435/252.31; 435/252.33; 435/254.11; 435/254.2; 435/254.21; 536/23.51; 530/351; 424/85.2

(58) Field of Search ............................ 435/69.52, 320.1, 435/240.2, 252.3, 254.11, 325, 348, 354, 254.2, 254.21, 252.31, 252.33; 536/23.5, 23.51; 530/351; 424/85.2

(56) References Cited

U.S. PATENT DOCUMENTS

| | | | | |
|---|---|---|---|---|
| 4,675,285 | * | 6/1987 | Clark et al. | 435/6 |
| 4,703,008 | * | 10/1987 | Lin | 435/360 |
| 4,727,138 | * | 2/1988 | Goeddel et al. | 536/23.52 |
| 4,810,643 | * | 3/1989 | Souza | 435/69.5 |
| 4,877,729 | * | 10/1989 | Clark et al. | 435/69.52 |

FOREIGN PATENT DOCUMENTS

| | | |
|---|---|---|
| 0138133 | 4/1985 | (EP) . |
| 0224294 | 6/1987 | (EP) . |
| 0244042 | 11/1987 | (EP) . |
| 8800598 | 1/1988 | (WO) . |
| 8804691 | 6/1988 | (WO) . |

OTHER PUBLICATIONS

Yang et al., *Cell* (1986)47:3–10.
Clark–Lewis et al., *Science* (1986) 231:134–139.
DeLamarter et al., *EMBO J.* (1985) 4(10):2575–2581.
Dorssers et al., *Exp. Hematol.* (1984) 12(6):357.
Fung et al., *Nature* (1984) 307:233–237.
Garland et al., *Exp. Hematol.* (1983) 11(8):757–761.
Hapel et al., *Blood* (1985) 65(6):1453–1459.
Higashi et al., *J. Bio. Chem.* (1983) 258(15):9522–9527.
Ihle et al., *Adv. Viral. Oncology* (1984) 4:95–137.
Kinder et al., *Proc. Natl. Acad. Sci.* (1986) 83:1001–1005.
Kriegler et al., *Blood* (1982) 60(2):503–508.
Lemischka et al., *Cell* (1985) 45:917–927.
March et al., *Nature* (1985) 315:641–647.
Metcalf et al., *Blood* (1986) 67(2):257–267.
Metcalf, *Brit. J. Hematol.* (1986) 62:409–412.
Miyatake et al., *Proc. Natl. Acad. Sci.* (1985) 82:316–320.
Schrader et al., *Proc. Natl. Acad. Sci.* (1986) 83:2458–2462.
Shaw et al., *Cell* (1986) 46:659–667.
van Bekkum et al., Bone Marrow Transplantation: Biological Mechanisms and Clinical Practice, Marcel Dekker, Inc., New York, 1985, pp. 1–72.
Whetton et al., *TIBS* May, 1986, pp. 207–211.
Yokota et al., *Adv. Gene Technol.* (1985) 2:49–52.
Yokota et al., *Proc. Natl. Acad. Sci.* (1984) 91:1070–1074.
Zwarthoff et al., *Nuc. Acid Res.* (1985) 13(3):791–804.
Cohen et al., *Nucleic Acids Research* (1986) 14(9):3641–3658.
Parks et al., *Journal of Biological Chemistry* (1989) 264(10):5420–5427.
Park et al., *J. Biol. Chem.* (1989) 264(10):5420–5422.
Alberts, B. et al., Eds., "Molecular Biology of The Cell" Second Edition, (1989) Garland Publishing, Inc., New York, p. 115.
Ayala, F.J., & Kiger, V.A. (1980) *Modern Genetics*, Menlo Park: Benjamin/Cummings; pp. 45, 47, 48.*
Hopp, T.P. (1986) *J. Immunol. Meth.* 88: 1–18.*
Jeong, M.C., et al. (1998) *Mol. Cell. Probes* 12: 49–53, 1998.*
Schweiger, A., et al. *J. Allergy Clin. Immunol.* 105 (1,2S):189, Jan. 2000.*

* cited by examiner

*Primary Examiner*—David L. Fitzgerald
(74) *Attorney, Agent, or Firm*—Morrison & Foerster LLP

(57) ABSTRACT

The invention relates to nucleotide sequences encoding human interleukin-3 (hIL-3) as well as recombinant DNAs, expression cassettes, transformed host cells, and recombinant expression methods comprising such sequences. Additionally, the invention describes proteins having hIL-3 activity, as purified, recombinantly produced, or fusion protein forms of hIL-3, as well as methods of using such proteins to produce antibodies capable of immunospecific reaction with hIL-3.

34 Claims, 32 Drawing Sheets

```
      ILE PHE ***
H:489 ATC TTT TGAGTCCAACGTCCAGCTCGTTCTCTGGGCCTTCTCACCACAGAGCCTCGGGACATCAAAAACAGCAGAACTTCTGAAACCTCTGGGTCATCTCTCACACAT
M:479 ... ... ..CAGCCCGCATCTGGCTCCGTCTCT......CCTAACCGTGGAACCGTGGAATGTTAA.AACAGCAGGCAGAGCACCTAAAGTCTG.AATGTTCCTCATGG
            GLNPROALASERGLYSERVALSER      PROASNARGGLYTHRVALGLUCYS***
                       130                                140

H:597 TCCAGGACCAGAAGCATTTCACCTTTTCCTGCGGCATCAGATGAATTGTTAA.TTATCTAATTTCTGAAATGTGCAGCTCCCATTTGGCCTTGTGCGGTTGTGTTCTCAT
M:571 CCCATGGTCAAAAGGATTTTACATTCCTTTATGCCATCAAATGTCTTATCAATTTATCTACTTTCTGAAATTTACAACTCTCCTTTGGCTTTACCTAATTATGTTC.CTA

H:706 TTTTATCCCATTGAGACTATTTATTTATGTATGTATGTATTTATTTATTTATTGCCTGGAGTG..TGAACTGTATTTATTTTAGCAGAGGAGCCATGTCCTGCTGCTTCT
M:680 TTTTATTCCATTAAGGCTATTTATTTATGTATTTATGTATTTATTTATTTATTGCCTTCTGTGATGTGAGTATATCTGTTTTAGCTGAGGAGGAGTTTC........TCC

H:814 GCAAAAAACTCAGAGTGGGGTGGGGAGCATGTTCATTTGTACCTCGAGTTTTAAACTGGTTCCTAGGGATGTGTGAGAATAAACTAGACTCTGAACA  910
M:782 AAAGAAAATTCCAAGGAAGACTGGGGCCATGTTCATTTGTCCCTTGTGGAAATAAATAACTTTGAACAAA  852
```

FIG. 1B pTZ18R  gggaattcgagctcggtacccggggatcctctagagtcgacctgcaggcatgcaagcttg

EcoRI SacI KpnI SmaI BamHI XbaI SalI PstI SphI HindIII pT1  gggaattcgagctcgatatcaagcttagatctcgagggggatcctctagagtcgacctgcag EcoRI SacI EcoRV HindIII BglII BamHI XbaI SalI PstI gcatgcaagctgcatatgcagcttg SphI NdeI

FIG. 6 pGB/IL-301

Met Thr Met Ile Thr Asn Ser Arg Gly Ser Gly Pro
atg acc atg att acg aat tcc cgg gga tct gGA CCA Glu Gln Asp Arg Val Pro Pro Ala Asp Pro Asn Met
GAA CAA GAC AGA GTG CCT CCT GCC GAT CCA AAC ATG Ser Arg Leu Pro Val Leu Leu Leu Leu Gln Leu Leu
AGC CGC CTG CCC GTC CTG CTC CTG CTC CAA CTC CTG Val Arg Pro Gly Leu Gln Ala[1] Pro Met Thr Gln Thr
GTC CGC CCC GGA CTC CAA GCT CCC ATG ACC CAG ACA Thr Pro Leu Lys Thr Ser Trp Val Asn Cys Ser Asn
ACG CCC TTG AAG ACA AGC TGG GTT AAC TGC TCT AAC Met Ile Asp
ATG ATC GAT pGB/IL-302

Met Thr Met Ile Thr Asn Ser Arg Gly Ser Ser Arg
atg acc atg att acg aat tcc cgg gga tcc tct aga Val Asp Pro[2] Met Thr Gln Thr Thr Pro Leu Lys Thr
gtc gac CCC ATG ACC CAG ACA ACG CCC TTG AAG ACA Ser Arg Val Asn Cys Ser Asn Met Ile Asp
AGC CGG GTT AAC TGC TCT AAC ATG ATC GAT pGB/IL-303

Met Thr Met Ile Thr Asn Ser Arg Gly Ser Ser Arg
atg acc atg att acg aat tcc cgg gga tcc tct aga Val Asp Pro[2] Met Thr Gln Thr Thr Pro Pro Lys Thr
gtc gac CCC ATG ACC CAG ACA ACG CCC CCG AAG ACA Ser Arg Val Asn Cys Ser Asn Met Ile Asp
AGC CGG GTT AAC TGC TCT AAC ATG ATC GAT pGB/IL-304

Met Thr Met Ile Thr Asn Leu Ile Arg Leu Thr Ile
atg acc atg att acg aat tta ata cga ctc act ata Gly Asn Ser Ser Ser Val Pro Gly Asp Pro Leu Glu
ggg aat tcg agc tcg gta ccc ggg gat cct cta gag Ser Ile Asp Pro[2] Thr Thr Glu Thr Thr Pro Leu Lys
tcg atc gac CCC ACG ACC CAG ACA ACG CCC CTG AAG Thr Ser Trp Val Asn Cys Ser Asn Met Ile Asp
ACA AGC TGG GTT AAC TGC TCT AAC ATG ATC GAT

FIG. 8A pGB/IL-305

Met Thr Met Ile Thr Asn Leu Ile Arg Leu Thr Ile
atg acc atg att acg aat tta ata cga ctc act ata Gly Asn Ser Ser Ser Val Pro Gly Asp Pro Leu Glu
ggg aat tcg agc tcg gta ccc ggg gat cct cta gag Asn[15] Cys Ser Asn Met Ile Asp
AAC TGC TCT AAC ATG ATC GAT pGB/IL-306

Met Ala[1] Pro Met Thr Gln Thr Thr Pro Leu Lys Thr
atg GCT CCC ATG ACC CAG ACA ACG CCC TTG AAG ACA Ser Trp Val Asn Cys Ser Asn Met Ile Asp
AGC TGG GTT AAC TGC TCT AAC ATG ATC GAT

FIG. 8B

*Sequence of the N-terminus of the fusion protein:*

Met Ser Tyr Ala Val Cys Arg Met Glu Lys

Val Lys Ser Gly Val Pro Ser Ser Asn Ser Gly

Pro Glu Gln Asp Arg Val Pro Pro Ala Asp Pro

Asn Met Ser Arg Leu .................. Ala Pro .......

−19 → hIL−3 signal sequence +1 → hIL−3 mature sequence pIL-3:precursor gene human IL-3.

```
        10        20        30        40        50        60        70
AATTCACCTCGAAAGCAAGCTGATAAACCGATACAATTAAAGGCTCCTTTTGGAGCCTTTTTTTTTGGAGATTTT

 80        90       100       110       120       130       140       150
CAACGTGAAAAAATTATTATTCGCAATTCCAAGCTAATTCACCTCGAAAGCAAGCTGATAAACCGATACAATTAA

       160       170       180       190       200       210       220
AGGCTCCTTTTGGAGCCTTTTTTTTTGGAGATTTTCAACGTGAAAAAATTATTATTCGCAATTCCAAGCTCTGCC

230       240       250       260       270       280       290       300
TCGCGCGTTTCGGTGATGACGGTGAAAACCTCTGACACATGCAGCTCCCGGAGACGGTCACAGCTTGTCTGTAAG

       310       320       330       340       350       360       370
CGGATGCAGATCACGCGCCCTGTAGCGGCGCATTAAGCGCGGCGGGTGTGGTGGTTACGCGCAGCGTGACCGCTA

380       390       400       410       420       430       440       450
CACTTGCCAGCGCCCTAGCGCCCGCTCCTTTCGCTTTCTTCCCTTCCTTTCTCGCCACGTTCGCCGGCTTTCCCC

       460       470       480       490       500       510       520
GTCAAGCTCTAAATCGGGGGCTCCCTTTAGGGTTCCGATTTAGTGCTTTACGGCACCTCGACCCCAAAAAACTTG

530       540       550       560       570       580       590       600
ATTAGGGTGATGGTTCACGTAGTGGGCCATCGCCCTGATAGACGGTTTTTCGCCCTTTGACGTTGGAGTCCACGT

       610       620       630       640       650       660       670
TCTTTAATAGTGGACTCTTGTTCCAAACTGGAACAACACTCAACCCTATCTCGGTCTATTCTTTTGATTTATAAG

680       690       700       710       720       730       740       750
GGATTTTGCCGATTTCGGCCTATTGGTTAAAAAATGAGCTGATTTAACAAAAATTTAACGCGAATTTTAACAAAA

       760       770       780       790       800       810       820
TATTAACGTTTACAATTTGATCTGCGCTCGGTCGTTCGGCTGCGGCGAGCGGTATCAGCTCACTCAAAGGCGGTA

830       840       850       860       870       880       890       900
ATACGGTTATCCACAGAATCAGGGGATAACGCAGGAAAGAACATGTGAGCAAAAGGCCAGCAAAAGGCCAGGAAC

       910       920       930       940       950       960       970
CGTAAAAAGGCCGCGTTGCTGGCGTTTTTCCATAGGCTCCGCCCCCCTGACGAGCATCACAAAAATCGACGCTCA

980       990      1000      1010      1020      1030      1040      1050
AGTCAGAGGTGGCGAAACCCGACAGGACTATAAAGATACCAGGCGTTTCCCCCTGGAAGCTCCCTCGTGCGCTCT

      1060      1070      1080      1090      1100      1110      1120
CCTGTTCCGACCCTGCCGCTTACCGGATACCTGTCCGCCTTTCTCCCTTCGGGAAGCGTGGCGCTTTCTCAATGC

1130      1140      1150      1160      1170      1180      1190      1200
TCACGCTGTAGGTATCTCAGTTCGGTGTAGGTCGTTCGCTCCAAGCTGGGCTGTGTGCACGAACCCCCCGTTCAG

      1210      1220      1230      1240      1250      1260      1270
CCCGACCGCTGCGCCTTATCCGGTAACTATCGTCTTGAGTCCAACCCGGTAAGACACGACTTATCGCCACTGGCA

1280      1290      1300      1310      1320      1330      1340      1350
GCAGCCACTGGTAACAGGATTAGCAGAGCGAGGTATGTAGGCGGTGCTACAGAGTTCTTGAAGTGGTGGCCTAAC
```

FIG. 17A 1360 1370 1380 1390 1400 1410 1420
TACGGCTACACTAGAAGGACAGTATTTGGTATCTGCGCTCTGCTGAAGCCAGTTACCTTCGGAAAAAGAGTTGGT 1430 1440 1450 1460 1470 1480 1490 1500
AGCTCTTGATCCGGCAAACAAACCACCGCTGGTAGCGGTGGTTTTTTTGTTTGCAAGCAGCAGATTACGCGCAGA 1510 1520 1530 1540 1550 1560 1570
AAAAAAGGATCTCAAGAAGATCCTTTGATCTTTTCTACGGGGTCTGACGCTCAGTGGAACGAAAACTCACGTTAA 1580 1590 1600 1610 1620 1630 1640 1650
GGGATTTTGGTCATGAGATTATCAAAAAGGATCTTCACCTAGATCCTTTTAAATTAAAAATGAAGTTTTAAATCA 1660 1670 1680 1690 1700 1710 1720
ATCTAAAGTATATATGAGTAAACTTGGTCTGACAGTTACCAATGCTTAATCAGTGAGGCACCTATCTCAGCGATC 1730 1740 1750 1760 1770 1780 1790 1800
TGTCTATTTCGTTCATCCATAGTTGCCTGACTCCCCGTCGTGTAGATAACTACGATACGGGAGGGCTTACCATCT 1810 1820 1830 1840 1850 1860 1870
GGCCCCAGTGCTGCAATGATACCGCGAGACCCACGCTCACCGGCTCCAGATTTATCAGCAATAAACCAGCCAGCC 1880 1890 1900 1910 1920 1930 1940 1950
GGAAGGGCCGAGCGCAGAAGTGGTCCTGCAACTTTATCCGCCTCCATCCAGTCTATTAATTGTTGCCGGGAAGCT 1960 1970 1980 1990 2000 2010 2020
AGAGTAAGTAGTTCGCCAGTTAATAGTTTGCGCAACGTTGTTGCCATTGCTGCAGGCATCGTGGTGTCACGCTCG 2030 2040 2050 2060 2070 2080 2090 2100
TCGTTTGGTATGGCTTCATTCAGCTCCGGTTCCCAACGATCAAGGCGAGTTACATGATCCCCCATGTTGTGCAAA 2110 2120 2130 2140 2150 2160 2170
AAAGCGGTTAGCTCCTTCGGTCCTCCGATCGTTGTCAGAAGTAAGTTGGCCGCAGTGTTATCACTCATGGTTATG 2180 2190 2200 2210 2220 2230 2240 2250
GCAGCACTGCATAATTCTCTTACTGTCATGCCATCCGTAAGATGCTTTTCTGTGACTGGTGAGTACTCAACCAAG 2260 2270 2280 2290 2300 2310 2320
TCATTCTGAGAATAGTGTATGCGGCGACCGAGTTGCTCTTGCCCGGCGTCAACACGGGATAATACCGCGCCACAT 2330 2340 2350 2360 2370 2380 2390 2400
AGCAGAACTTTAAAAGTGCTCATCATTGGAAAACGTTCTTCGGGGCGAAAACTCTCAAGGATCTTACCGCTGTTG 2410 2420 2430 2440 2450 2460 2470
AGATCCAGTTCGATGTAACCCACTCGTGCACCCAACTGATCTTCAGCATCTTTTACTTTCACCAGCGTTTCTGGG 2480 2490 2500 2510 2520 2530 2540 2550
TGAGCAAAAACAGGAAGGCAAAATGCCGCAAAAAAGGGAATAAGGGCGACACGGAAATGTTGAATACTCATACTC 2560 2570 2580 2590 2600 2610 2620
TTCCTTTTTCAATATTATTGAAGCAGACAGTTTTATTGTTCATGATGATATATTTTTATCTTGTGCAATGTAACA 2630 2640 2650 2660 2670 2680 2690 2700
TCAGAGATTTTGAGACACAACGTGGCTTTGTTGAATAAATCGAACTTTTGCTGAGTTGACTCCCCGCGCGCGATG

FIG. 17B

```
        2710      2720      2730      2740      2750      2760      2770
GGTCGAATTTGCTTTCGAAAAAAAAGCCCGCTCATTAGGCGGGCTAAAAAAAAGCCCGCTCATTAGGCGGGCTCG

 2780      2790      2800      2810      2820      2830      2840      2850
AATTTCTGCCATTCATCCGCTTATTATCACTTATTCAGGCGTAGCAACCAGGCGTTTAAGGGCACCAATAACTGC

        2860      2870      2880      2890      2900      2910      2920
CTTAAAAAAATTACGCCCCGCCCTGCCACTCATCGCAGTACTGTTGTAATTCATTAAGCATTCTGCCGACATGGA

 2930      2940      2950      2960      2970      2980      2990      3000
AGCCATCACAGACGGCATGATGAACCTGAATCGCCAGCGGCATCAGCACCTTGTCGCCTTGCGTATAATATTTGC

        3010      3020      3030      3040      3050      3060      3070
CCATAGTGAAAACGGGGGCGAAGAAGTTGTCCATATTCGCCACGTTTAAATCAAAACTGGTGAAACTCACCCAGG

 3080      3090      3100      3110      3120      3130      3140      3150
GATTGGCTGAGACGAAAAACATATTCTCAATAAACCCTTTAGGGAAATAGGCCAGGTTTTCACCGTAACACGCCA

        3160      3170      3180      3190      3200      3210      3220
CATCTTGCGAATATATGTGTAGAAACTGCCGGAAATCGTCGTGGTATTCACTCCAGAGCGATGAAAACGTTTCAG

 3230      3240      3250      3260      3270      3280      3290      3300
TTTGCTCATGGAAAACGGTGTAACAAGGGTGAACACTATCCCATATCACCAGCTCACCGTCTTTCATTGCCATAC

        3310      3320      3330      3340      3350      3360      3370
GAAATTCCGGATGAGCATTCATCAGGCGGGCAAGAATGTGAATAAAGGCCGGATAAAACTTGTGCTTATTTTTCT

 3380      3390      3400      3410      3420      3430      3440      3450
TTACGGTCTTTAAAAAGGCCGTAATATCCAGCTAAACGGTCTGGTTATAGGTACATTGAGCAACTGACTGAAATG

        3460      3470      3480      3490      3500      3510      3520
CCTCAAAATGTTCTTTACGATGCCATTGGGATATATCAACGGTGGTATATCCAGTGATTTTTTTCTCCATTTTAG

 3530      3540      3550      3560      3570      3580      3590      3600
CTTCCTTAGCTCCTGAAAATCTCGATAACTCAAAAAATACGCCCGGTAGTGATCTTATTTCATTATGGTGAAAGT

        3610      3620      3630      3640      3650      3660      3670
TGGAACCTCTTACGTGCCGATCAACGTCTCATTTTCGCCAAAAGTTGGCCCAGGGCTTCCCGGTATCAACAGGGA

 3680      3690      3700      3710      3720      3730      3740      3750
CACCAGGATTTATTTATTCTGCGAAGTGATCTTCCGTCACAGGTATTTATTCGAAGACGAAAGGGCATCGCGCGC

        3760      3770      3780      3790      3800      3810      3820
GGGGAATTCCCGGGAGAGCTCGATATCGCATGCGGTACCTCTAGAAGAAGCTTGGAGACAAGGTAAAGGATAAAA

 3830      3840      3850      3860      3870      3880      3890      3900
CAGCACAATTCCAAGAAAAACACGATTTAGAACCTAAAAAGAACGAATTTGAACTAACTCATAACCGAGAGGTAA

        3910      3920      3930      3940      3950      3960      3970
AAAAAGAACGAAGTCGAGATCAGGGAATGAGTTTATAAAATAAAAAAAGCACCTGAAAAGGTGTCTTTTTTTGAT

 3980      3990      4000      4010      4020      4030      4040      4050
GGTTTTGAACTTGTTCTTTCTTATCTTGATACATATAGAAATAACGTCATTTTTATTTTAGTTGCTGAAAGGTGC
```

FIG. 17C

```
      4060      4070      4080      4090      4100      4110      4120
GTTGAAGTGTTGGTATGTATGTGTTTTAAAGTATTGAAAACCCTTAAAATTGGTTGCACAGAAAAACCCCATCTG

 4130      4140      4150      4160      4170      4180      4190      4200
TTAAAGTTATAAGTGACTAAACAAATAACTAAATAGATGGGGGTTTCTTTTAATATTATGTGTCCTAATAGTAGC

      4210      4220      4230      4240      4250      4260      4270
ATTTATTCAGATGAAAAATCAAGGGTTTTAGTGGACAAGACAAAAAGTGGAAAAGTGAGACCATGGAGAGAAAAG

 4280      4290      4300      4310      4320      4330      4340      4350
AAAATCGCTAATGTTGATTACTTTGAACTTCTGCATATTCTTGAATTTAAAAAGGCTGAAAGAGTAAAAGATTGT

      4360      4370      4380      4390      4400      4410      4420
GCTGAAATATTAGAGTATAAACAAAATCGTGAAACAGGCGAAAGAAAGTTGTATCGAGTGTGGTTTTGTAAATCC

 4430      4440      4450      4460      4470      4480      4490      4500
AGGCTTTGTCCAATGTGCAACTGGAGGAGAGCAATGAAACATGGCATTCAGTCACAAAAGGTTGTTGCTGAAGTT

      4510      4520      4530      4540      4550      4560      4570
ATTAAACAAAAGCCAACAGTTCGTTGGTTGTTTCTCACATTAACAGTTAAAAATGTTTATGATGGCGAAGAATTA

 4580      4590      4600      4610      4620      4630      4640      4650
AATAAGAGTTTGTCAGATATGGCTCAAGGATTTCGCCGAATGATGCAATATAAAAAAATTAATAAAAATCTTGTT

      4660      4670      4680      4690      4700      4710      4720
GGTTTTATGCGTGCAACGGAAGTGACAATAAATAATAAAGATAATTCTTATAATCAGCACATGCATGTATTGGTA

 4730      4740      4750      4760      4770      4780      4790      4800
TGTGTGGAACCAACTTATTTTAAGAATACAGAAAACTACGTGAATCAAAAACAATGGATTCAATTTTGGAAAAAG

      4810      4820      4830      4840      4850      4860      4870
GCAATGAAATTAGACTATGATCCAAATGTAAAAGTTCAAATGATTCGACCGAAAAATAAATATAAATCGGATATA

 4880      4890      4900      4910      4920      4930      4940      4950
CAATCGGCAATTGACGAAACTGCAAAATATCCTGTAAAGGATACGGATTTTATGACCGATGATGAAGAAAAGAAT

      4960      4970      4980      4990      5000      5010      5020
TTGAAACGTTTGTCTGATTTGGAGGAAGGTTTACACCGTAAAAGGTTAATCTCCTATGGTGGTTTGTTAAAAGAA

 5030      5040      5050      5060      5070      5080      5090      5100
ATACATAAAAAATTAAACCTTGATGACACAGAAGAAGGCGATTTGATTCATACAGATGATGACGAAAAAGCCGAT

      5110      5120      5130      5140      5150      5160      5170
GAAGATGGATTTTCTATTATTGCAATGTGGAATTGGGAACGGAAAAATTATTTTATTAAAGAGTAGTTCAACAAA

 5180      5190      5200      5210      5220      5230      5240      5250
CGGGCCAGTTTGTTGAAGATTAGATGCTATAATTGTTATTAAAAGGATTGAAGGATGCTTAGGAAGACGAGTTAT

      5260      5270      5280      5290      5300      5310      5320
TAATAGCTGAATAAGAACGGTGCTCTCCAAATATTCTTATTTAGAAAAGCAAATCTAAAATTATCTGAAAAGGGA

 5330      5340      5350      5360      5370      5380      5390      5400
ATGAGAATAGTGAATGGACCAATAATAATGACTAGAGAAGAAAGAATGAAGATTGTTCATGAAATTAAGGAACGA
```

FIG. 17D 5410 5420 5430 5440 5450 5460 5470
ATATTGGATAAATATGGGGATGATGTTAAGGCTATTGGTGTTTATGGCTCTCTTGGTCGTCAGACTGATGGGCCC 5480 5490 5500 5510 5520 5530 5540 5550
TATTCGGATATTGAGATGATGTGTGTCATGTCAACAGAGGAAGCAGAGTTCAGCCATGAATGGACAACCGGTGAG 5560 5570 5580 5590 5600 5610 5620
TGGAAGGTGGAAGTGAATTTTGATAGCGAAGAGATTCTACTAGATTATGCATCTCAGGTGGAATCAGATTGGCCG 5630 5640 5650 5660 5670 5680 5690 5700
CTTACACATGGTCAATTTTTCTCTATTTTGCCGATTTATGATTCAGGTGGATACTTAGAGAAAGTGTATCAAACT 5710 5720 5730 5740 5750 5760 5770
GCTAAATCGGTAGAAGCCCAAACGTTCCACGATGCGATTTGTGCCCTTATCGTAGAAGAGCTGTTTGAATATGCA 5780 5790 5800 5810 5820 5830 5840 5850
GGCAAATGGCGTAATATTCGTGTGCAAGGACCGACAACATTTCTACCATCCTTGACTGTACAGGTAGCAATGGCA 5860 5870 5880 5890 5900 5910 5920
GGTGCCATGTTGATTGGTCTGCATCATCGCATCTGTTATACGACGAGCGCTTCGGTCTTAACTGAAGCAGTTAAG 5930 5940 5950 5960 5970 5980 5990 6000
CAATCAGATCTTCCTTCAGGTTATGACCATCTGTGCCAGTTCGTAATGTCTGGTCAACTTTCCGACTCTGAGAAA 6010 6020 6030 6040 6050 6060 6070
CTTCTGGAATCGCTAGAGAATTTCTGGAATGGGATTCAGGAGTGGACAGAACGACACGGATATATAGTGGATGTG 6080 6090 6100 6110 6120 6130 6140 6150
TCAAAACGCATACCATTTTGAACGATGACCTCTAATAATTGTTAATCATGTTGGTTACGTATTTATTAACTTCTC 6160 6170 6180 6190 6200 6210 6220
CTAGTATTAGTAATTATCATGGCTGTCATGGCGCATTAACGGAATAAAGGGTGTGCTTAAATCGGGCCATTTTGC 6230 6240 6250 6260 6270 6280 6290 6300
GTAATAAGAAAAAGGATTAATTATGAGCGAATTGAATTAATAATAAGGTAATAGATTTACATTAGAAAATGAAAG 6310 6320 6330 6340 6350 6360 6370
GGGATTTTATGCGTGAGAATGTTACAGTCTATCCCGGCATTGCCAGTCGGGGATATTAAAAAGAGTATAGGTTTT 6380 6390 6400 6410 6420 6430 6440 6450
TATTGCGATAAACTAGGTTTCACTTTGGTTCACCATGAAGATGGATTCGCAGTTCTAATGTGTAATGAGGTTCGG 6460 6470 6480 6490 6500 6510 6520
ATTCATCTATGGGAGGCAAGTGATGAAGGCTGGCGCTCTCGTAGTAATGATTCACCGGTTTGTACAGGTGCGGAG 6530 6540 6550 6560 6570 6580 6590 6600
TCGTTTATTGCTGGTACTGCTAGTTGCCGCATTGAAGTAGAGGGAATTGATGAATTATATCAACATATTAAGCCT 6610 6620 6630 6640 6650 6660 6670
TTGGGCATTTTGCACCCCAATACATCATTAAAAGATCAGTGGTGGGATGAACGAGACTTTGCAGTAATTGATCCC 6680 6690 6700 6710 6720 6730 6740 6750
GACAACAATTTGATTAGCTTTTTTCAACAAATAAAAAGCTAAAATCTATTATTAATCTGTTCAGCAATCGGGCGC

FIG. 17E

```
       6760      6770      6780      6790      6800      6810      6820
GATTGCTGAATAAAAGATACGAGAGACCTCTCTTGTATCTTTTTTATTTTGAGTGGTTTTGTCCGTTACACTAGA

 6830      6840      6850      6860      6870      6880      6890      6900
AAACCGAAAGACAATAAAAATTTTATTCTTGCTGAGTCTGGCTTTCGGTAAGCTAGACAAAACGGACAAAATAAA

       6910      6920      6930      6940      6950      6960      6970
AATTGGCAAGGGTTTAAAGGTGGAGATTTTTTGAGTGATCTTCTCAAAAAATACTACCTGTCCCTTGCTGATTTT

 6980      6990      7000      7010      7020      7030      7040      7050
TAAACGAGCACGAGAGCAAAACCCCCCTTTGCTGAGGTGGCAGAGGGCAGGTTTTTTTGTTTCTTTTTTCTCGTA

       7060      7070      7080      7090      7100      7110      7120
AAAAAAAGAAAGGTCTTAAAGGTTTTATGGTTTTGGTCGGCACTGCCGACAGCCTCGCAGGACACACACTTTATG

 7130      7140      7150      7160      7170      7180      7190      7200
AATATAAAGTATAGTGTGTTATACTTTACTTGGAAGTGGTTGCCGGAAAGAGCGAAAATGCCTCACATTTGTGCC

       7210      7220      7230      7240      7250      7260      7270
ACCTAAAAAGGAGCGATTTACATATGAGTTATGCAGTTTGTAGAATGCAAAAAGTGAAATCAGGGGGATCCTCTA

 7280      7290      7300      7310      7320      7330
GAGTCGAGCTCAAGCTAGCTTGGTACGTACCAGATCTGAGATCACGCGTTCTAGAGGTCGA
```

FIG. 17F

Sequence:

S.D.

Hpall promoter-AAAGGAGCGATTTACAT ATG AGT
met ser

TAT GCA GTT TGT AGA ATG CAA AAA GTG
tyr ala val cys arg met gln lys val

S.D.

AAA TCA GGG GGA TCC AAG GAG GTG ATC
lys ser gly gly ser lys glu val ile

TAG AGT CGA CATG...pIL-3
stop met

| 4466 | 4476 | 4486 | 4496 | 4506 | 4516 | 4526 | 4536 | 4546 | 4556 |
|---|---|---|---|---|---|---|---|---|---|
| CCGCGGGGAT | CGACTCATAA | AATAGTAACC | TTCTAATGCG | TATCTATTGA | CTACCAACCA | TTAGTGTGGT | TGCAGAAGGC | GGAATTCTCC | CTTCTTCGAA |
| 4566 | 4576 | 4586 | 4596 | 4606 | 4616 | 4626 | 4636 | 4646 | 4656 |
| TTCAGCTTGC | TTTTCATTTT | TATTTTCCAT | TTTTCAGTTT | TTGTTTGTGT | CGAATTTAGC | CAGTTGCTTC | TCCAAGATGA | AAAAACCCCT | GCGCAGTTTC |
| 4666 | 4676 | 4686 | 4696 | 4706 | 4716 | 4726 | 4736 | 4746 | 4756 |
| TGTGTCGCAA | GATCCTAATC | GACTTTTCCA | CCCCCCACAA | AAGTAAATGT | TTCTTTGTTA | CATTCGCGTG | GGTAGCTAGC | TCCCCGAATC | TCAAAGGACT |
| 4766 | 4776 | 4786 | 4796 | 4806 | 4816 | 4826 | 4836 | 4846 | 4856 |
| TAGGGACTGC | ACTACATCAG | AGTGTGTTCA | CCTGGTTTGC | TGCCTGGTTT | GAAAGAAAAG | AGCGGGAACT | CGCGGGTTCC | CGGCGAATAA | TCATGCGATA |
| 4866 | 4876 | 4886 | 4896 | 4906 | 4916 | 4926 | 4936 | 4946 | 4956 |
| GTCCTTTGGC | CTTCCAAGTC | GCATGTAGAG | TAGACAACAG | ACAGGGAGGG | CAGGAAGGAT | CTTTCACTGA | GATCCTGTAT | CTTGTTGGGT | AAGTCGGATG |
| 4966 | 4976 | 4986 | 4996 | 5006 | 5016 | 5026 | 5036 | 5046 | 5056 |
| AAAGGGGAAT | CGTATGAGAT | TGGAGAGGAT | GCGGAAGAGG | TAACGCCTTT | TGTTAACTTG | TTTAATTATT | ATGGGGCAGG | CGAGAGGGGG | AGGAATGTAT |
| 5066 | 5076 | 5086 | 5096 | 5106 | 5116 | 5126 | 5136 | 5146 | 5156 |
| GTGTGTGAGG | CGGGCGAGAC | GGAGCCATCC | AGGCCAGGTA | GAAATAGAGA | AAGCCGAATG | TTAGACAATA | TGGCAGCGTA | GTAGAGTAGG | TAGGTAGGCA |
| 5166 | 5176 | 5186 | 5196 | 5206 | 5216 | 5226 | 5236 | 5246 | 5256 |
| AGTACTGCTA | GCAAAGAGGA | GAAGGGTAAG | CTCACTCTTC | GCATTCCACA | CCGTTAGTGT | GTCAGTTTAG | ACAAAAAAAC | AACTACTATA | CCAATTAGTA |
| 5266 | 5276 | 5286 | 5296 | 5306 | 5316 | 5326 | 5336 | 5346 | 5356 |
| GACTGTGAAC | TGACTTTTGG | AACGGCTTTT | CGGACTGCGA | TTATTCGTGA | GGAATCAAGG | TAGGAATTTG | GTCATATTTA | CGGACAACAG | TGGGTGATTC |
| 5366 | 5376 | 5386 | 5396 | 5406 | 5416 | 5426 | 5436 | 5446 | 5456 |
| CCATATGGAG | TAGGAAAACG | AGATCATGGT | ATCCTCAGAT | ATGTTGCGGA | ATTCTGTTCA | CCGCAAAGTT | CAGGGTGCTC | TGGTGGGTTT | CGGTTGGTCT |
| 5466 | 5476 | 5486 | 5496 | 5506 | 5516 | 5526 | 5536 | 5546 | 5556 |
| TTGCTTTGCT | TCTCCCTTGT | CTTGCATGTT | AATAATAGCC | TAGCCTGTGA | GCCGAAACTT | AGGGTAGGCT | TAGTGTTGGA | ACGTACATAT | GTATCACGTT |
| 5566 | 5576 | 5586 | 5596 | 5606 | 5616 | 5626 | 5636 | 5646 | 5656 |
| GACTTGGTTT | AACCAGGCGA | CCTGGTAGCC | AGCCATACCC | ACACACGTTT | TTTGTATTCT | TCAGTATAGT | TGTGAAAAGT | GTAGCGGAAA | TATGTGGTCC |
| 5666 | 5676 | 5686 | 5696 | 5706 | 5716 | 5726 | 5736 | 5746 | 5756 |
| GAGCAACAGC | GTCTTTTTCT | AGTAGTGCGG | TCGGTTACTT | GGTTGACATT | GGTATTTGGA | CTTTGTTGCT | ACACCATTCA | CTACTTGAAG | TCGAGTGTGA |
| 5766 | 5776 | 5786 | 5796 | 5806 | 5816 | 5826 | 5836 | 5846 | 5856 |
| AGGGTATGAT | TTCTAGTGGT | GAACACCTTT | AGTTACGTAA | TGTTTTCATT | GCTGTTTTAC | TTGAGATTTC | GATTGAGAAA | AAGGTATTTA | ATAGCTCGAA |

FIG. 22A

| | | | | | | | | | |
|---|---|---|---|---|---|---|---|---|---|
| 5866 | 5876 | 5889 | 5896 | 5906 | 5916 | 5926 | 5936 | 5946 | 5956 |
| TCAATGTGTT | ATCATTGTGA | AGATGTTCTT | CCCTAACTCG | AAAGGTATAT | GAGGCTTGTG | TTTCTTAGGA | GAATTATTAT | TCTTTTGTTA | TGTTGCGCTT |
| 5966 | 5976 | 5986 | 5996 | 6006 | 6016 | 6026 | 6036 | 6046 | 6056 |
| GTAGTTGGAA | AAGGTGAAGA | GACAAAAGCT | TAACACTTGA | AATTTAGGAA | AGAGCAGAAT | TTGGCAAAAA | AAATAAAAAA | AAAATAAACA | CGTCGACTTG |
| 6066 | 6076 | 6086 | 6096 | 6106 | 6116 | 6126 | 6136 | 6146 | 6156 |
| TGAGCGGATA | ACAATCGACA | CATACTCATC | GAGAACTGAA | AGATATGAGA | TTTCCATCGA | TTTTTACTGC | AGTTTTATTC | GCAGCATCCT | CCGCATTAGC |
| 6166 | 6176 | 6186 | 6196 | 6206 | 6216 | 6226 | 6236 | 6246 | 6256 |
| TGCTCCAGTC | AACACTACAA | CAGAAGATGA | AACGGCACAA | ATTCCGGCTG | AAGCTGTCAT | CGGTTACTTA | GATTTAGAAG | GGGATTTCGA | TGTTGCTGTT |
| 6266 | 6276 | 6286 | 6296 | 6306 | 6316 | 6326 | 6336 | 6346 | 6356 |
| TTGCCATTTT | CCAACAGCAC | AAATAACGGG | TTATTGTTTA | TAAATACTAC | TATTGCCAGC | ATTGCTGCTA | AAGAAGAAGG | GGTATCTCTA | GATAAAAGAG |
| 6366 | 6376 | 6386 | 6396 | 6406 | 6416 | 6426 | 6436 | 6446 | 6456 |
| CTCCCATGAC | CCAGACAACG | CCCTTGAAGA | CAAGCTGGGT | TAACTGCTCT | AACATGATCG | ATGAAATTAT | AACACACTTA | AAGCAGCCAC | CTTTGCCTTT |
| 6466 | 6476 | 6486 | 6496 | 6506 | 6516 | 6526 | 6536 | 6546 | 6556 |
| GCTGGACTTC | AACAACCTCA | ATGGGGAAGA | CCAAGACATT | CTGATGGAAA | ATAACCTTCG | AAGGCCAAAC | CTGGAGGCAT | TCAACAGGGC | TGTCAAGAGT |
| 6566 | 6576 | 6586 | 6596 | 6606 | 6616 | 6626 | 6636 | 6646 | 6656 |
| TTACAGAACG | CATCAGCAAT | TGAGAGCATT | CTTAAAAATC | TCCTGCCATG | TCTGCCCCTG | GCCACGGCCG | CACCCACGCG | ACATCCAATC | CATATCAAGG |
| 6666 | 6676 | 6686 | 6696 | 6706 | 6716 | 6726 | 6736 | 6746 | 6756 |
| ACGGTGACTG | GAATGAATTC | CGGAGGAAAC | TGACGTTCTA | TCTGAAAACC | CTTGAGAATG | CGCAGGCTCA | ACAGACGACT | TTGAGCCTCG | CGATCTTTTG |
| 6766 | 6776 | 6786 | 6796 | 6806 | 6816 | 6826 | 6836 | 6846 | 6856 |
| AGTCCAACGT | CCAGCTCGTT | CTCTGGGCCT | TCTCACCACA | GAGCCTCGGG | ACATCAAAAA | CAGCAGAACT | TCTGAAACCT | CTGGGTCATC | TCTCACACAT |
| 6866 | 6876 | 6886 | 6896 | 6906 | 6916 | 6926 | 6936 | 6946 | 6956 |
| TCCAGGACCA | GAAGCATTTC | ACCTTTTCCT | GCGGCATCAG | ATGAATTGTT | AATTATCTAA | TTTCTGAAAT | GTGCAGCTCC | CATTTGGCCT | TGTGCGGTTG |
| 6966 | 6976 | 6986 | 6996 | 7006 | 7016 | 7026 | 7036 | 7046 | 7056 |
| TGTTCTCATT | TTTATCCCAT | TGAGACTATT | TATTTATGTA | TGTATGTATT | TATTTATTTA | TTGCCTGGAG | TGTGAACTGT | ATTTATTTTA | GCAGAGGAGC |
| 7066 | 7076 | 7086 | 7096 | 7106 | 7116 | 7126 | 7136 | 7146 | 7156 |
| CATGTCCTGC | TGCTTCTGCA | AAAAACTCAG | AGTGGGGTGG | GGAGCATGTT | CATTTGTACC | TCGAGAATTT | ATACTTAGAT | AAGTATGTAC | TTACAGGTAT |
| 7166 | 7176 | 7186 | 7196 | | | | | | |
| ATTTCTATGA | GATACTGATG | TATACATGCA | TGATAATATT | TAAAGCTT | | | | | |

FIG. 22B

| | | | | | | | | | |
|---|---|---|---|---|---|---|---|---|---|
| 4466 | 4476 | 4486 | 4496 | 4506 | 4516 | 4526 | 4536 | 4546 | 4556 |
| CCGCGGGGAT | CGACTCATAA | AATAGTAACC | TTCTAATGCG | TATCTATTGA | CTACCAACCA | TTAGTGTGGT | TGCAGAAGGC | GGAATTCTCC | CTTCTTCGAA |
| 4566 | 4576 | 4586 | 4596 | 4606 | 4616 | 4626 | 4636 | 4646 | 4656 |
| TTCAGCTTGC | TTTTCATTTT | TATTTTCCAT | TTTTCAGTTT | TTGTTTGTGT | CGAATTTAGC | CAGTTGCTTC | TCCAAGATGA | AAAAACCCCT | GCGCAGTTTC |
| 4666 | 4676 | 4686 | 4696 | 4706 | 4716 | 4726 | 4736 | 4746 | 4756 |
| TGTGTCGCAA | GATCCTAATC | GACTTTTCCA | CCCCCCACAA | AAGTAAATGT | TTCTTTGTTA | CATTCGCGTG | GGTAGCTAGC | TCCCCGAATC | TCAAAGGACT |
| 4766 | 4776 | 4786 | 4796 | 4806 | 4816 | 4826 | 4836 | 4846 | 4856 |
| TAGGGACTGC | ACTACATCAG | AGTGTGTTCA | CCTGGTTTGC | TGCCTGGTTT | GAAAGAAAAG | AGCGGGAACT | CGCGGGTTCC | CGGCGAATAA | TCATGCGATA |
| 4866 | 4876 | 4886 | 4896 | 4906 | 4916 | 4926 | 4936 | 4946 | 4956 |
| GTCCTTTGGC | CTTCCAAGTC | GCATGTAGAG | TAGACAACAG | ACAGGGAGGG | CAGGAAGGAT | CTTTCACTGA | GATCCTGTAT | CTTGTTGGGT | AAGTCGGATG |
| 4966 | 4976 | 4986 | 4996 | 5006 | 5016 | 5026 | 5036 | 5046 | 5056 |
| AAAGGGGAAT | CGTATGAGAT | TGGAGAGGAT | GCGGAAGAGG | TAACGCCTTT | TGTTAACTTG | TTTAATTATT | ATGGGGCAGG | CGAGAGGGGG | AGGAATGTAT |
| 5066 | 5076 | 5086 | 5096 | 5106 | 5116 | 5126 | 5136 | 5146 | 5156 |
| GTGTGTGAGG | CGGGCGAGAC | GGAGCCATCC | AGGCCAGGTA | GAAATAGAGA | AAGCCGAATG | TTAGACAATA | TGGCAGCGTA | GTAGAGTAGG | TAGGTAGGCA |
| 5166 | 5176 | 5186 | 5196 | 5206 | 5216 | 5226 | 5236 | 5246 | 5256 |
| AGTACTGCTA | GCAAAGAGGA | GAAGGGTAAG | CTCACTCTTC | GCATTCCACA | CCGTTAGTGT | GTCAGTTTAG | ACAAAAAAAC | AACTACTATA | CCAATTAGTA |
| 5266 | 5276 | 5286 | 5296 | 5306 | 5316 | 5326 | 5336 | 5346 | 5356 |
| GACTGTGAAC | TGACTTTTGG | AACGGCTTTT | CGGACTGCGA | TTATTCGTGA | GGAATCAAGG | TAGGAATTTG | GTCATATTTA | CGGACAACAG | TGGGTGATTC |
| 5366 | 5376 | 5386 | 5396 | 5406 | 5416 | 5426 | 5436 | 5446 | 5456 |
| CCATATGGAG | TAGGAAAACG | AGATCATGGT | ATCCTCAGAT | ATGTTGCGGA | ATTCTGTTCA | CCGCAAAGTT | CAGGGTGCTC | TGGTGGGTTT | CGGTTGGTCT |
| 5466 | 5476 | 5486 | 5496 | 5506 | 5516 | 5526 | 5536 | 5546 | 5556 |
| TTGCTTTGCT | TCTCCCTTGT | CTTGCATGTT | AATAATAGCC | TAGCCTGTGA | GCCGAAACTT | AGGGTAGGCT | TAGTGTTGGA | ACGTACATAT | GTATCACGTT |
| 5566 | 5576 | 5586 | 5596 | 5606 | 5616 | 5626 | 5636 | 5646 | 5656 |
| GACTTGGTTT | AACCAGGCGA | CCTGGTAGCC | AGCCATACCC | ACACACGTTT | TTTGTATTCT | TCAGTATAGT | TGTGAAAAGT | GTAGCGGAAA | TATGTGGTCC |
| 5666 | 5676 | 5686 | 5696 | 5706 | 5716 | 5726 | 5736 | 5746 | 5756 |
| GAGCAACAGC | GTCTTTTTCT | AGTAGTGCGG | TCGGTTACTT | GGTTGACATT | GGTATTTGGA | CTTTGTTGCT | ACACCATTCA | CTACTTGAAG | TCGAGTGTGA |
| 5766 | 5776 | 5786 | 5796 | 5806 | 5816 | 5826 | 5836 | 5846 | 5856 |
| AGGGTATGAT | TTCTAGTGGT | GAACACCTTT | AGTTACGTAA | TGTTTTCATT | GCTGTTTTAC | TTGAGATTTC | GATTGAGAAA | AAGGTATTTA | ATAGCTCGAA |

FIG. 23A 5866 5876 5886 5896 5906 5916 5926 5936 5946 5956
TCAATGTGTT ATCATTGTGA AGATGTTCTT CCCTAACTCG AAAGGTATAT GAGGCTTGTG TTTCTTAGGA GAATTATTAT TCTTTTGTTA TGTTGCGCTT 5966 5976 5986 5996 6006 6016 6026 6036 6046 6056
GTAGTTGGAA AAGGTGAAGA GACAAAAGCT TAACACTTGA AATTTAGGAA AGAGCAGAAT TTGGCAAAAA AAATAAAAAA AAAATAAACA CGTCGACTTG 6066 6076 6086 6096 6106 6116 6126 6136 6146 6156
TGAGCGGATA ACACTCGAGG GATCTTCATT ATGAAATTCT CTACTATATT AGCCGCATCT ACTGCTTTAA TTTCCGTTGT TATGGCTGCT CCAGTTTCTA 6166 6176 6186 6196 6206 6216 6226 6236 6246 6256
CCGAAACTGA CATCGACGAT CTTCCAATTT CGGTTCCAGA AGAAGCCTTG ATTGGATTCA TTGACTTAAC CGGGGATGAA GTTTCCTTGT TGCCTGTTAA 6266 6276 6286 6296 6306 6316 6326 6336 6346 6356
TAACGGAACC CACACTGGTA TTCTATTCTT AAACACCACC ATCGCTGAAG CTGCTTTCGC TGACAAGGAT GATTTGAAGA AGCGCGCTCC CATGACCCAG 6366 6376 6386 6396 6406 6416 6426 6436 6446 6456
ACAACGCCCT TGAAGACAAG CTGGGTTAAC TGCTCTAACA TGATCGATGA AATTATAACA CACTTAAAGC AGCCACCTTT GCCTTTGCTG. GACTTCAACA 6466 6476 6486 6496 6506 6516 6526 6536 6546 6556
ACCTCAATGG GGAAGACCAA GACATTCTGA TGGAAAATAA CCTTCGAAGG CCAAACCTGG AGGCATTCAA CAGGGCTGTC AAGAGTTTAC AGAACCCATC 6566 6576 6586 6596 6606 6616 6626 6636 6646 6656
AGCAATTGAG AGCATTCTTA AAAATCTCCT GCCATGTCTG CCCCTGGCCA CGGCCGCACC CACGCGACAT CCAATCCATA TCAAGGACGG TGACTGGAAT 6666 6676 6686 6696 6706 6716 6726 6736 6746 6756
GAATTCCGGA GGAAACTGAC GTTCTATCTG AAAACCCTTG AGAATGCGCA GGCTCAACAG ACGACTTTGA GCCTCGCGAT CTTTTGAGTC CAACGTCCAG 6766 6776 6786 6796 6806 6816 6826 6836 6846 6856
CTCGTTCTCT GGGCCTTCTC ACCACAGAGC CTCGGGACAT CAAAAACAGC AGAACTTCTG AAACCTCTGG GTCATCTCTC ACACATTCCA GGACCAGAAG 6866 6876 6886 6896 6906 6916 6926 6936 6946 6956
CATTTCACCT TTTCCTGCGG CATCAGATGA ATTGTTAATT ATCTAATTTC TGAAATGTGC AGCTCCCATT TGGCCTTGTG CGGTTGTGTT CTCATTTTTA 6966 6976 6986 6996 7006 7016 7026 7036 7046 7056
TCCCATTGAG ACTATTTATT TATGTATGTA TGTATTTATT TATTTATTGC CTGGAGTGTG AACTGTATTT ATTTTAGCAG AGGAGCCATG TCCTGCTGCT 7066 7076 7086 7096 7106 7116 7126 7136 7146 7156
TCTGCAAAAA ACTCAGAGTG GGGTGGGGAG CATGTTCATT TGTACCTCGA GAATTTATAC TTAGATAAGT ATGTACTTAC AGGTATATTT CTATGAGATA 7166 7176 7186
CTGATGTATA CATGCATGAT AATATTTAAA GCTT

FIG.23B

| 10 | 20 | 30 | 40 | 50 | 60 | 70 | 80 | 90 | 100 |
|---|---|---|---|---|---|---|---|---|---|
| TCGAATTTGC | GGGGAGAAGA | TGGATCTATG | CTAAATCTAA | ATAGGCATTT | GAAAAACGAC | GACGAGTTAC | ACGACATATC | GCCATCTTTA | AATGAGCAAC |
| 110 | 120 | 130 | 140 | 150 | 160 | 170 | 180 | 190 | 200 |
| CACACTGGGA | CCTCATAGAG | GACGGGTCTC | GCTGGAGTAA | ATTTTTCAAC | GGGATAATTA | AGACGACAAG | AAGGTTCACG | AAATCTTTAA | TGAGGTCTTT |
| 210 | 220 | 230 | 240 | 250 | 260 | 270 | 280 | 290 | 300 |
| AGTCAGAGGC | AGGAACAGCC | GTCAAGGGGG | CATAAGACTA | CGGTCATCCC | CATCTGCCTC | TTCGTCCAGC | CTTGCCAACA | GGGAGTTCTT | CAGAGACATG |
| 310 | 320 | 330 | 340 | 350 | 360 | 370 | 380 | 390 | 400 |
| GAGGCTCAAA | ACGAAATTAT | TGACAGCCTA | GACATCAATA | GTCATACAAC | AGAAAGCGAC | CACCCAACTT | TGGCTGATAA | TAGCGTATAA | ACAATGCATA |
| 410 | 420 | 430 | 440 | 450 | 460 | 470 | 480 | 490 | 500 |
| CTTTGTACGT | TCAAAATACA | ATGCAGTAGA | TATATTTATG | CATATTACAT | ATAATACATA | TCACATAGGA | AGCAACAGGC | GCGTTGGACT | TTTAATTTTC |
| 510 | 520 | 530 | 540 | 550 | 560 | 570 | 580 | 590 | 600 |
| GAGGACCGCG | AATCCTTACA | TCACACCCAA | TCCCCCACAA | GTGATCCCCC | ACACACCATA | GCTTCAAAAT | GTTTCTACTC | CTTTTTTACT | CTTCCAGATT |
| 610 | 620 | 630 | 640 | 650 | 660 | 670 | 680 | 690 | 700 |
| TTCTCGGACT | CCGCGCATCG | CCGTACCACT | TCAAAACACC | CAAGCACAGC | ATACTAAATT | TCCCCTCTTT | CTTCCTCTAG | GGTGTCGTTA | ATTACCCGTA |
| 710 | 720 | 730 | 740 | 750 | 760 | 770 | 780 | 790 | 800 |
| CTAAAGGTTT | GGAAAAGAAA | AAAGAGACCG | CCTCGTTTCT | TTTTCTTCGT | CGAAAAAGGC | AATAAAAATT | TTTATCACGT | TTCTTTTTCT | TGAAAATTTT |
| 810 | 820 | 830 | 840 | 850 | 860 | 870 | 880 | 890 | 900 |
| TTTTTTTGAT | TTTTTTCTCT | TTCGATGACC | TCCCATTGAT | ATTTAAGTTA | ATAAACGGTC | TTCAATTTCT | CAAGTTTCAG | TTTCATTTTT | CTTGTTCTAT |
| 910 | 920 | 930 | 940 | 950 | 960 | 970 | 980 | 990 | 1000 |
| TACAACTTTT | TTTACTTCTT | GCTCATTAGA | AAGAAAGCAT | AGCAATCTAG | TCGACAGATC | TCTCGAGTGC | TTTTGTGCGC | GTATGTTTAT | GTATGTACCT |
| 1010 | 1020 | 1030 | 1040 | 1050 | 1060 | 1070 | 1080 | 1090 | 1100 |
| CTCTCTCTAT | TTCTATTTTT | AAACCACCCT | CTCAATAAAA | TAAAAATAAT | AAAGTATTTT | TAAGGAAAAG | ACGTGTTTAA | GCACTGACTT | TATCTACTTT |
| 1110 | | | | | | | | | |
| TTGTACGTCT | AGA | | | | | | | | |

FIG. 24

MOLECULAR CLONING AND EXPRESSION OF THE PRO$^8$ ISOFORM OF HUMAN IL-3

This application is a continuation of U.S. Ser. No. 08/321,480, filed Oct. 11, 1994 and now abandoned, which is a a continuation of U.S. Ser. No. 07/854,297, filed Mar. 19, 1992, now abandoned, which is in turn a continuation of U.S. Ser. No. 07/249,184, filed Aug. 16, 1988, now abandoned, which is the national stage (35 U.S.C. §371) of international application PCT/NL87/00037 filed Dec 16, 1987. The international application claims priority from Netherlands applications 86/202,285.2, filed Dec. 16, 1986, and 87/201,322.2, filed Jul. 13, 1987.

FIELD OF THE INVENTION

The present invention relates to cDNA encoding human interleukin-3 (hIL-3) and its use, inter alia, in the cloning and expression in various organisms, including microorganisms, in particular yeasts, bacteria and fungi, tissue culture cells and transgenic animals and plants.

BACKGROUND OF THE INVENTION

Hemopoiesis involves the active process of proliferation and differentation of pluripotent progenitor cells into all types of mature blood cells and some specialized tissue calls. Production of functional blood cells is regulated by specific proteins, the hemopoietic growth factors (HGFs). Some of the HGFs control maturation of a specific maturation lineage, whereas others stimulate proliferation and differentiation of progenitors along multiple pathways. Much of our knowledge of the hemopoietic differentiation process has been obtained from mouse studies in vitro and in vivo, using purified growth factors. The murine growth factor interleukin-3 (mIL-3), also termed Multi-CSF, mast cell growth factor, stem cell activating factor or several other designations, stimulates the proliferation of developmentally early, multipotent cells (CFU-S) as detected by the spleen colony assay, resulting in the production of progenitor cells along the erythroid, megacaryocyte, granulocyte/macrophage, osteoblast and several other lineages. Furthermore, mIL-3 has been implicated in replication of pluripotent stem cells, probably in synergism with other HGFs.

In recent years, several groups have succeeded in cloning mIL-3 cDNA. No results have been reported so far of identifying homologous sequences in human DNA using mIL-3 DNA as a probe. Presumably, the human gene has diverged extensively from the mIL-3 gene or has lost its function during primate evolution. However, human leukocytes were found to produce a HGF(s) which can replace mIL-3 in supporting the proliferation of murine CFU-S. Thus, the existence of a human HGF was postulated, which shares biological properties with mIL-3 and therefore could be the human homolog. Yang, Y-C, et al, *Cell* (1986) 47:3–10, dated 10 October discloses cDNA encoding a protein having IL-3 Like activity from gibbon T-cells, and retrieval of a genomic DNA which encodes the human counterpart. The sequence of a cDNA encoding human IL-3 can be deduced from the human gene sequence published by Yang et al. However, said article does neither disclose nor teach a method for isolation of a cDNA encoding human IL-3, nor was the production of hIL-3 achieved. This invention describes for the first the isolation of a cDNA comprising the entire coding sequence for human IL-3.

Human IL-3 protein has never been prepared in purified form, nor have its characteristics, other than its activity in certain in vitro proliferation assays and deduced primary structure, been disclosed. The present invention permits the recovery of purified human IL-3, and identification of its characteristics through recombinant production: from a cDNA clone.

SUMMARY OF THE INVENTION

As stated above, the present invention for the time describes the isolation of a cDNA comprising the entire coding sequence for human IL-3. The low degree of homology between the DNA sequences coding for murine and human IL-3 does not permit the retrieval of a cDNA for hIL-3 by hybridization with the mIL-3 coding sequence. Unexpectedly, the hIL-3 cDNA clone could be isolated by exploiting the rather high degree of homology in the 3' noncoding part of the cDNA's. The availability of the cDNA clone permits the production of hIL-3 by a wide range of host organisms. Subsequent to large scale production the protein may be purified and used therapeutically.

The present invention permits production of recombinant human IL-3 protein in a wide range of host cells by transcription and translation from a cDNA sequence encoding the human IL-3 protein. The production of the protein is illustrated in several hosts, including *E. coli,* COS cells, C127 cells, *B. subtilis* and *B. licheniformis, S. cerevisiae* and *K. lactis,* hereinbelow. Production in other hosts using appropriate expression systems is also made possible by provision of the intronless cDNA. More generally, the availability of antihuman IL-3 antibodies which permit identification of colonies exhibiting successful production of the recombinant protein aids in production of human IL-3 from any recombinant system.

In one aspect, therefore, the invention is directed to a recombinant, intronless, DNA encoding human IL-3 protein.

In another aspect, it is directed to expression systems capable of effecting the expression of said DNA sequence encoding hIL-3 in an appropriate host.

In other aspects, the invention is directed to recombinant human IL-3 protein in glycosylated or unglycosylated form, to human IL-3 free of substances normally accompanying said protein, and to antibodies specifically reactive with these recombinant or purified proteins.

BRIEF DESCRIPTION OF THE DRAWINGS

FIG. 6 (SEQ ID NO:5 & SEQ ID NO:6) shows the sequence of the multicloning site in pTZ18R (Pharmacia) and its derivative pT1.

FIG. 8 (SEQ ID NO:7, SEQ ID NO:8, SEQ ID NO:9, SEQ ID NO:10, SEQ ID :11, SEQ ID NO:12, SEQ ID NO:13, SEQ ID NO:14, SEQ ID NO:15, SEQ ID NO:16, SEQ ID NO:17 and SEQ ID NO:18) shows the sequences of fusion regions of lacZ/hmulti-CSF DNA for various bacterial expression vectors. The sequence of clones is given from the start of the lacZ protein in either pUC8 or pTZ18R (lower case letters) and of hmulti-CSF DNA sequence up to the ClaI site at position 158. Mutations in the hmulti-CSF DNA sequence are underlined, resulting in: $trp^{13} \rightarrow arg^{13}$ (pGB/IL-302); $leu^9 \rightarrow pro^9$ and $trp^{13} \rightarrow arg^{13}$ (pGB/IL-303); $met^3 \rightarrow thr^3$ and a silent change (pGB/IL-304). The superscripts denote the amino acid residue number of the mature protein.

FIG. 17 (SEQ ID NO:21) shows the nucleotide sequence of plasmid pBHA1.

FIG. 21 shows a schematic representation of plasmid pGB/IL-316.

FIG. 22 (SEQ ID NO:25) shows the nucleotide sequence of plasmid pGB/IL-316 between the unique SacII site in the lactase promoter and the HindIII site behind the terminator (residues 4457 to 7204).

FIG. 23 (SEQ ID NO:26) shows the nucleotide sequence of-plasmid pGB/IL-318 between the unique SacII site in the lacatse promoter and the HindIII site behind the terminator (residues 4457 to 7190).

FIG. 24 (SEQ ID NO:27) shows the nucleotide sequence of the EF-1α promoter, SalI-BglII-XhoI linker and actin terminator as present on plasmid pGB/TEFact.

DETAILED DESCRIPTION OF THE INVENTION

A. Definitions

As used herein, "human IL-3", "hIL-3, "human multi-CSF", and "hmulti-CSF" are used interchangeably, and designate a protein preparation which exhibits the following activities:

1. The protein stimulates colony formation by human hemopoietic progenitor cells wherein the colonies formed include erythroids, granulocytes, granulocyte macrophages, and mixed.

2. The protein stimulates DNA synthesis by human acute myelogenous leukemia (AML) blasts, as evidenced, for example, by labeled thymidine uptake.

To fit the definition of hmulti-CSF, the activity in the foregoing assay must not be substantially inhibited by antibodies raised in response to, and immunospecific for, GM-CSF, unless these antibodies also inhibit these activities by the illustrative hmulti-CSF below.

Figure 1A:
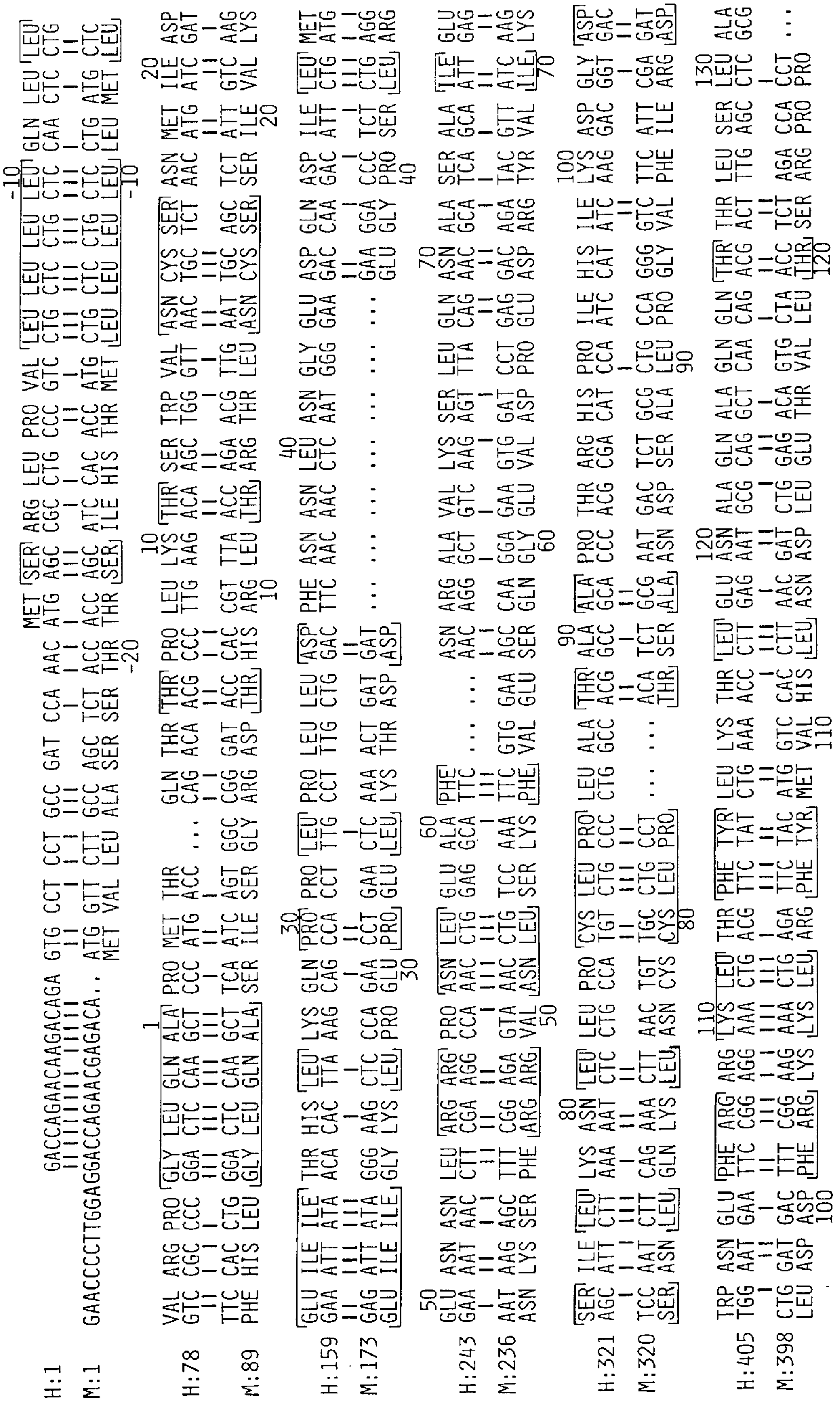
FIG. 1 (SEQ ID NO:1, SEQ ID NO:2, SEQ ID NO:3& SEQ ID NO:4)shows a comparison of DNA and protein sequences of human multi-CSF and mouse IL-3. The hmulti-CSF protein and DNA sequence (clone D11, top lines) were aligned with the mIL-3 DNA (11, 35) and protein sequence (30). Identical nucleotides are indicated by a vertical line, identical amino acids are shown in boxes. Black dots indicate a polyadenylation signal sequence and horizontal bars mark ATTTA repeat units.

One illustrative form of hmulti-CSF is shown in FIG. 1 as a 133 amino acid mature protein, having a 19 amino acid signal sequence. The amino acid sequence of FIG. 1 is identical with that disclosed by Yang, Y-C., et al., *Cell* (1986) 47:3–10 (supra) except at position 8 of the mature protein wherein he Ser of the Yang protein is replaced by Pro herein. As shown herein, this amino acid sequence is effective in its nonglycosylated form. However, it contains two glycosylation sites, and the glycosylated form is also included within the scope of the invention. It is also recognized that the protein may exist in acid addition salt form, basic salt form, or may be neutral, depending upon the pH of its surroundings. Derivatization by phosphorylation, acetylation, and so forth, to the extent that activity is not destroyed, also results in a protein included within the scope of the invention.

It is also recognized that the entire sequence may not be necessary for activity. Parts of the amino acid sequence may be deleted or replaced, while retaining biological activity. As illustrated herein, the alanine at position 1 may be deleted, as may as many as the first fourteen amino acid residues if replaced by a sequence of residues of a fused peptide sequence. In addition, it is believed that the murine form of the protein requires only the first 79 residues for activity; this corresponds approximately to the first 83 residues of the human counterpart. Accordingly, fragments which comprise only the first 83 amino acid residues of the protein, and the N-terminal replaced forms thereof are also included within the scope of the invention. Furthermore, it should be considered that the N-terminus of mature hIL-3 is formed by the residues ala-pro-met etc. (see FIG. 1). It is known that the protein, when secreted by a yeast host, may in some instances be shortened by two amino acids (ala-pro), due to the interaction with a dipeptidylaminopeptidase (72). The hIL-3 without the N-terminal alanine and proline still retains its biological activity. Yeast strains carrying a null mutation of the X-prolyl dipeptidylaminopeptidase gene will produce complete hIL-3 (amino acids 1–133). Accordingly, included in the multi-CSFs of the invention are those which contain and those which do not contain the N-terminal alanine and proline, produced by X-prolyl dipeptidylaminopeptidase mutants and wild type hosts, respectively.

When produced as a mature protein in a procaryotic host, the coding sequence for the mature protein will be prefaced by an ATG start codon. The resulting N-terminal methionine may then be removed, or partially removed, by processing within the bacterial host, depending on the nature of the subsequent amino acid sequence. Again, both forms of hIL-3 are biologically active. Therefore, included in the hmulti-CSFs of the invention are those which-contain and those which do not contain the N-terminal methionine.

From the above it is clear that amino acid changes may be introduced into the human IL-3 protein, without affecting its biological function. It is recognized that minor changes in amino acid sequences by chemical modification of the encoded residue; substitution of a different residue, or deletion or addition of one or more, but preferably only one, residue results in proteins which retain activity. Accordingly, these nondestructive mutations are also included within the invention, in particular, the naturally occurring allelic variations and other mutations which are nonlethal to the activity.

On the other hand it should be considered that amino acid changes in the human IL-3 protein may be beneficial to the therapeutic use of the protein. As recognized herein, the mature protein has four conserved domains at residues 15–36, 54–61, 74–91, and 107–118. Proteins containing single and multiple amino acid changes in the nonconserved regions, 1–14 (which are, in any event, replacable by the sequences of host derived fusion proteins), 37–53, 62–73, 92–106, and 119–133 are possible. However, it appears that the cysteine residues at positions 16 and 84 may be necessary for disulfide bridge formation as they are conserved between species. Changes in the conserved domains mentioned above may influence biological properties of the protein, such as receptor binding and signal transduction. It is envisaged that hIL-3 having altered properties are of therapeutic use. Such derivatives of hIL-3, which may be made by known protein engineering techniques, are to be understood within the scope of the present invention.

The protein preparation may contain the hmulti-CSF peptides in monomeric or aggregated form, provided the aggregates retain activity as above-defined.

As used herein, "expression system" refers to a DNA sequence which contains both a coding sequence whose expression is desired and appropriate control sequences in operable linkage with it which permits its expression when the control sequences are compatible with the host into which the expression system is placed. As is generally understood, "control sequences" refers to DNA segments which are required for or regulate the expression of the coding sequence with which they are operably linked.

Control sequences for all hosts include promoters, which may or may not be controllable by regulation of their environment. Typical promoters suitable for procaryotes include, for example, the trp promoter (inducible by tryptophan deprivation), the lac promoter (inducible with the galactose analog IPTG), the beta-lactamase promoter, and the phage-derived $P_L$ promoter (inducible by temperature variation). Additionally, especially for expression in Bacillus, useful promoters include those for alpha-amylase, protease, Spo2 and synthetic promoter sequences. Suitable promoters for expression in yeast include the 3-phosphoglycerate kinase promoter and those for other glycolytic. enzymes, as well as promoter regions for alcohol dehydrogenase and yeast phosphatase. Also useful are the transcription elongation factor (TEF) and lactase promoters. Mammalian expression generally employs promoters derived from viruses such as the adenovirus promoters and the SV40 promoter systems, but they also include regulatable promoters such as the metallothionein promoter, which is controlled by heavy metals or glucocorticoid concentration. There are also now available viral-based insect cell expression systems, as well as expression systems based on plant cell promoters such as the nopaline synthetase promoters.

In addition to the promoter DNA sequence, which is necessary for the transcription of the gene by RNA polymerase, a variety of control sequences, including those regulating termination (for example, resulting in polyadenylation sequences in eucaryotic systems) are also useful in controlling expression. Some systems also contain enhancer elements which are desirable but not necessarily necessary in effecting expression.

Translation controls include a ribosome binding site (RBS) in procaryotic systems, whereas in eucaryotic systems translation may be controlled by the nucleotide sequence around the AUG codon.

As implied above, recombinant protein production can be effected in a wide variety of hosts, including bacteria (predominantly *E. coli,* Bacillus, and Streptomyces), in yeast and fungi (such as Saccharomyces, Kluyveromyces, and Aspergillus), and in mammalian and other cell cultures such as COS cells, C127 cells, Chinese hamster ovary cells, *Spodoptera frugiperda* (Sf9) cells, and so forth. The protein may be produced as an intracellular mature or fusion protein, or may be secreted when the DNA encoding an appropriate compatible signal is included in the gene.

The present invention for the first time enables large scale production of recombinant human IL-3, so that this protein—in purified form—can now be used as a therapeutic agent. The methods described herein provide means for producing glycosylated as well as unglycosylated forms of the protein, which can be purified to substantially pure human IL-3. "Purified " human IL-3 refers to human IL-3 as defined above which is free of other proteins which normally accompany it.

B. Retrieval of cDNA Encoding Human IL-3

Human IL-3 was isolated according to the following strategy .

1. A procedure was developed which allowed for reproducible production of hemopoietic growth factors (HGFs) by human leucocytes.

2. mRNA was prepared from such producing cells and transcribed into double-stranded cDNA.

3. The cDNA was screened with a complete mIL-3 cDNA which contained both the coding and untranslated 3' downstream portions to obtain DII.

4. The hybridyzing cDNA clone DII was inserted into an expression vector pLO to obtain pLB4 which was expressed in COS cells to confirm the presence of the sequence encoding human IL-3. Conditioned media from these cells showed the biological activity expected of hIL-3.

The human cDNA was retrievable using this procedure because despite considerable lack of homology with the murine coding sequence, a surprising degree of homology was present in the 3' untranslated region. Applicants are unaware of any prior disclosure of the use of a 3' untranslated sequence homology to retrieve an alternate species gene.

In more detail, conditioned medium of lymphocytes cultured in the presence of 12-0-tetradecanoylphorbol-13 acetate (TPA) and concanavalin A (Con A) is a suitable source for human HGFs as determined by assay of the medium using stimulation of mouse CFU-S in suspension cultures, proliferation of mIL-3 dependent DA-1 cells, human hemopoietic progenitor assays by colony formation in vitro, and in vitro stimulation of acute leukemia blasts. A cDNA library from human lymphocytes was constructed in lambda gt-10 phage (20) and screened using the HindIII-XbaI fragment of mIL-3 cDNA, for the occurrence of mIL-3 related sequences. No hybridizing clones were identified.

However, when complete murine IL-3 cDNA was used as probe, four clones were identified. Restriction enzyme analysis of the largest clone (D11) indicated a 910 bp insert containing an internal EcoRI site (at position 411, FIG. 1).

(It was investigated whether this EcoRI site had arisen by ligation of two independent cDNA fragments or was a naturally occurring site. Southern analysis of restriction enzyme digested human DNA using labeled 5' and 3' EcoRI fragments of clone D11 as probe, revealed identical DNA fragments following digestion with HindIII (15 kb) and BamHI (4.6 kb). Furthermore, the DNA sequence around the EcoRI site does not correspond to linker sequence (pCCGAATTCGG) used for inserting cDNA into phage DNA, indicating that these EcoRI fragments are derived from a single mRNA.)

From hybridization and sequencing experiments it was concluded that the small clones (II, IV and VI) are identical to the 3' nucleotide sequence of clone D11 and derived from the same mRNA species.

Computer assisted alignment (FIG. 1) of the D11 cDNA and the mIL-3, cDNA revealed sequence homology in the 5' terminal 100 bp, between nucleotides 236–269 and between nucleotides 598–803 in the 3' terminal region (68%, 71% and 73% homology, respectively). In particular, the region between nucleotides 706 and 763 is highly conserved (93% homology) and contains repetitive AT-rich sequences. The low homology in the 5' terminal 600 bp of the human cDNA (52%) precludes detection by hybridization with the HindIII-XbaI fragment of mIL-3.

Analysis of the human cDNA clone for an encoded protein shows an open reading frame up to the termination codon TGA at position 495–497 (FIG. 1). The first ATG triplet is probably the actual initiation codon of the encoded polypeptide. The putative encoded protein consists of a hydrophobic leader peptide of 19 amino acids, which is probably cleaved between the glycine and alanine residues (22, 23).

The alignment of the predicted amino acid residues of the human and mouse IL-3 (FIG. 1) reveals a homology of 50%, for the leader peptide (residues −26 to +1) and 28% for the mature protein (residues 1 to 133). Within the leader peptide, there are two conserved regions of four amino acids (residues −13 to −10 and −3 to +1) of which the second one encloses the processing site. The mature protein is 133 amino acids long and has a molecular weight of 15 kd. The mature protein has four conserved domains (residues 15–36, 54–61, 74–91 and 107–118) and contains two potential glycosylation sites (residues 15–17 and 70–72). Both cysteine residues present in the human protein (positions 16 and 84) are conserved and may play an essential role in protein folding by disulfide bridge formation.

In order to verify that this human cDNA encodes a functional protein that resembles mIL-3, the D11 cDNA was inserted in an eucaryotic expression vector (pLO, containing a SV40 transcription unit) to obtain the expression vector pLB4 and transfected to COS 1 cells. The COS/pLB4 conditioned medium (CM) was tested for (1) its capacity to stimulate colony formation by human bone marrow cells, and (2) to stimulate human acute myelogenous leukemia (AML) blasts.

In vitro colony growth of human hemopoietic progenitors depleted of myelomonocytic (Vim-2 positive) and T-lymphocytic (T-3 positive) accessory cells, was efficiently stimulated by COS/pLB4 CM. The data demonstrate stimulation of progenitors of several hemopoietic differentiation lineages and of a subpopulation of BFU-E by COS/pLB4 CM.

In a separate experiment, bone marrow was enriched for progenitor cells by density centrifugation, E-rosette sedimentation to remove T-lymphocytes and adherence to remove mononuclear phagocytes and cultured in enriched medium containing fetal calf serum. Under these conditions, the majority of the colonies obtained upon stimulation with COS/pLB4 CM contained two or more hemopoietic differentiation lineages: all contained macrophages, approximately half immature blasts and/or immature erythroid cells and/or neutrophilic granulocytes and a minority, in addition, basophilic or eosinophil granulocytes. These results demonstrate the multilineage stimulatory properties of the protein encoded by the human cDNA clone D11 and its action on developmentally early, multipotent hemopoietic cells.

With respect to AML stimulation, AML-blasts of five patients were stimulated with the COS/pLB4 CM and assayed for a response by measuring $^3$H-TdR incorporation and colony formation. Three of the five leukemia cell samples responded to the COS/pLB4 CM in both assays; characteristic dose-response relationships for colony formation and DNA synthesis of AML blasts of different patients were obtained. The responses to GM-CSF demonstrated further phenotypic differences among the leukemias responding to the COS/pLB4 CM.

These data demonstrate that the D11 cDNA clone contains the complete genetic information for a biologically active protein which is exported into the culture medium in the transformed COS cells. Despite the apparent lack of homology with respect to the protein sequence between the human protein and mIL-3 (only 30%), the proteins are comparable with respect to their biological function. Both proteins exert their effect on developmentally early hemopoietic progenitors of various lineages. The low homology at the amino acid level is also reflected by a low-homology in the coding nucleotide sequence. However, very unexpectedly, a rather high degree of homology—sufficient for retrieval of the human cDNA clone—occurred in the 3' untranslated region.

Southern analysis of human DNA revealed a single hybridizing gene indicating that this cDNA does not belong to a family of closely related genes.

From the foregoing results we conclude that the human cDNA insert in D11 encodes the human homolog of mIL-3. We decided to use the operational term hmulti-CSF for the protein encoded by the cDNA clone D11 in view of its major biological effect and assay.

The identification of hmulti-CSF cDNA clones by virtue of hybridization with the 3' terminal region of the mIL-3 cDNA was unexpected. Whereas homologous DNA sequences are in general predominantly found in the coding region, the hmulti-CSF sequence has extensively diverged (45% homology) in this part of the gene. Analysis of the highly conserved domain in the 3' terminal non-coding region reveals the occurance of 5 ATTTA repeat units which are all preserved in the mIL-3 cDNA (FIG. 1).

hMulti-CSF and mIL-3 display considerably less protein homology than other murine and human growth factors or lymphokines such as GM-CSF (25), interleukin-2 (25), interleukin-1 (26) and interferons (27–29). The biological activity of the mature mIL-3 appears to be contained in the first 79 amino acids, including an absolute requirement for the cysteine residue at position 17 (30). This cysteine residue is conserved in hmulti-CSF (FIG. 1, pos. 16) and may play an essential role in protein folding. The occurrence of a potential glycosylation site around this cysteine residue-may interfere with disulfide bridge formation.

C. Production and Formulation of hmulti-CSF

Applicants have provided a representative variety of expression systems capable of producing human IL-3 protein in a variety of forms—as fusion proteins, as mature intracellular proteins, and as secreted proteins. Applicants are unware of availability anywhere in the art of recombinant forms of human IL-3, or, indeed, of any human IL-3 in a preparation which is free of proteins normally accompanying this desired protein. Accordingly, the invention herein provides, for the first time, the human IL-3 protein in a manner which is capable of adaptation to therapeutic and diagnostic uses.

The human IL-3 can be produced as a fusion protein with sequences heterologous to the human IL-3 amino acid sequence. By "heterologous" is meant a sequence which is not found in human IL-3 itself, but is an unrelated sequence. This heterologous sequence may be derived from a bacterial protein, a yeast protein, a mammalian protein, or any of variety of miscellaneous fortuitously encoded sequences such as, for example, those encoded by polylinkers. It is clear from the results hereinbelow that at least the first 14 amino acids of the N-terminus of the human IL-3 sequence can be replaced by a heterologous sequence, at least if the fusion protein is further extended past the N-terminus.

The protein can also be obtained as a mature intracellular protein by constructs in which the ATG start codon is placed immediately upstream of the desired N-terminus. These intracellular proteins, whether mature or fusion proteins, can be recovered by lysing the cells and purifying the human IL-3 using standard protein purification techniques.

Protein purification is simplified if the human IL-3 is secreted into the medium. When produced in mammalian cells with which the native signal sequence is compatible, this native signal sequence can be used to effect secretion into the medium. In bacterial or yeast systems, signal sequences compatible with these hosts, such as the penicillinase or alpha-amylase sequence in bacteria or the alpha-factor signal sequence in yeast can be used.

When produced recombinantly, the human IL-3 is free of proteins normally accompanying it, and can be purified from the proteins and other materials indigenous to the recombinant host using, for example, chromatographic methods, gel filtration, ammonium sulfate precipitation, and so forth.

As described hereinbelow, the protein is useful for therapeutic and diagnostic purposes. For therapeutic uses, the protein may be formulated in ways standard for pharmaceutical compositions which are used for the administration of proteins. Suitable excipients include, for example, physiological saline, Ringer's solution, and so forth. Alternate formulations, including solid formulations (e.g. lyophilized), can also be employed.

D. Preparation of Antibodies

The availability of recombinant IL-3 protein or parts thereof will permit production of antibodies directed against the protein or parts thereof, as demonstrated hereinbelow. Such antibodies are useful, inter alia, for in vitro detection of colonies producing hIL-3, for therapeutical use, and for the purification of both natural and recombinant hIL-3.

Statement of Utility

The nucleotide sequence of the whole or parts of the cDNA of human IL-3, or closely-related DNA sequences will advantageously enable the detection of genetic abnormalities, including genomic rearrangements, restriction fragment-length polymorphisms, mutations and altered gene expression with the use of such techniques as the analysis of chromosomal DNA using restriction enzymes, DNA and RNA blotting as well as hybridization techniques (Maniatis et al. 1982) and two-dimensional gel electrophoresis (Fisher and Lerman, 1983).

The recombinant hmulti-CSF as provided by the present invention will facilitate a detailed analysis of its role in human hemopoiesis, in particular the possible synergism of hmulti-CSF and various other HGFs. Furthermore, hmulti-CSF is of considerable interest because of its applicability for in vitro diagnosis of human diseases in which hemopoietic progenitor cells are involved, which include the leukemia, as well as potential therapeutic applications aimed at expansion of hemopoiesis in vivo. The effect of hmulti-CSF on various hemopoietic malignancies with respect to terminal differentiation of the leukemic cells also needs to be explored. In addition hMulti-CSF may be required for establishing a proliferative state of human stem cells in gene therapy protocols, since stimulation with mIL-3 was shown to be required for succesful infection of mouse stem cells with recombinant, replication defective retroviruses.

IL-3 protein can also advantageously be used for the detection of early hemopoietic precursor cells in standardised in vitro cultures (Wagemaker and Visser, 1980; Metcalf et al. 1982; Merchav and Wagemaker, 1984, Metcalf, 1986).

IL-3 protein and variants can further be used for the multiplication of hemopoietic stem cells in vitro, possibly in conjunction with other growth factors, for bone marrow transplantation and the genetic manipulation of stem cells (Lowenberg and Dicke, 1977; Wagemaker and Petem, 1978; Lemischka et al, 1986).

The IL-3 protein can be used for the determination of the response pattern of malignant hemopoietic cells in in vitro tests (Touw and Lowenberg, 1985; Griffin et al, 1986; Griffin and Lowenberg, 1986).

The II-3 protein can further be used for the detection of remaining leukemic cells by in vitro methods (Touw and Lowenberg, 1986; Griffin et al, 1986; Griffin and Lowenberg, 1986).

Furthermore, the IL-3 protein can be used in vivo for the treatment and prevention of malignant and non-malignant disorders, either by itself or in combination, in which an obtained specific response by the hemopoietic system can result in a clinical benefit.

These applications include:

- cytopenias and/or immunosuppression due to infections such as AIDS
- cytopenias due to chemotherapy and/or irradiation
- bone disorders such as bone fractures and osteoporosis
- immunodeficienties due to general anaesthetic procedures
- recovery following bone marrow transplantation
- adjunct to vaccinations and adjunctive therapy of infections.

The cloned human IL-3 DNA sequence or closely-related DNA can be used for gene therapy in genetic deviations from the normal IL-3 gene.

To facilitate the above-described analysis, a large quantity of human IL-3 is required. The easiest way to obtain sufficient amounts of the protein is the production with microorganisms in particular yeasts, bacteria and fungi, e.g. Saccharomyces, Kluyveromyces, Aspergillus, Streptomyces, Bacillus and *E. coli* species. Production in mammalian and other eucaryotic systems, such as C127 cells, Spodoptera cells and transgenic animals and plants, is also possible for skilled persons following the teaching of the present invention. These possibilities are all included within the scope of this invention.

As an illustration how to obtain living cells that produce the hum an IL-3 protein by expression of the hIL-3 cDNA, a number of plasmids were constructed and transferred to *E. coli, B. subtilis, B. licheniformis, S. cerevisiae, K. lactis* and C127 cells. Using these host strains the production of recombinant human IL-3 was achieved. The products were tested for their capacity to stimulate human AML blasts as described above for the COS/pLB4 conditioned medium. From these experiments it appeared that the proteins made were biologically active.

The following examples are intended to illustrate but not to limit the invention.

EXAMPLE 1

Retrieval of cDNA Encoding Human multi-CSF (hmulti-CSF)

Human leukocytes stimulated with TPA (5 ng/ml) and ConA (10 ug/ml) produced considerable amounts of HGFs as measured by the murine stem cell proliferation assay and various other colony assays. Cells were harvested 24 hrs after stimulation, because mRNA production is often transient following stimulation with phorbol esters and lectins. Already after 24 hrs, HGFs were easily detectable in the CM.

mRNA Preparation

Cells were harvested, washed with PBS and homogenized in guanidinium isothiocyanate solution (36). RNA was pelleted through a cesium chloride cushion. Oligo(dT)-cellulose chromatography was used for selection of mRNAs (36).

cDNA Synthesis cDNA was synthesized essentially according to Gubler and Hoffman (37), using oligo(dT) as primer and AMV reverse transcriptase. Second strand was synthesized with RNaseH and *E. coli* DNA polymerase I. Gaps were closed with T4-DNA ligase and ends were flushed by T4-DNA polymerase. To protect internal EcoRI restriction sites, the cDNA was methylated with EcoRI methylase. Subsequently, the cDNA was ligated to phosphorylated EcoRI linkers with T4-DNA ligase. After digestion with EcoRI, excess linkers were removed by Sepharose CL-4B chromatography. The material recovered in the void volume of the column was larger than 250 bp and was used for construction of the libraries.

Construction of the Phage cDNA Library.

The cDNA was ligated to lambda gt10 phage arms (20) and packaged with commercial packaging extracts (Gigapack, Vector Cloning Systems). The recombinant phages were propagated in *E. coli* C600 hfl.

Screening of the Phage Library.

Of each plate containing 1–5000 plaques, two nitrocellulose filter replicas were made according to standard procedures. Filters were then hybridized with radiolabeled mIL-3 probe from the HindIII-XbaI fragment of mIL-3 cDNA or with the complete mIL-3 cDNA clone radiolabeled with random primers. The mIL-3 cDNA clone (pL101) was isolated from a WEHI-3B cDNA library. WEHI-3B mRNA was isolated using the guanidinium isothiocyanate CsCl method, size fractionated on sucrose gradient and injected into *Xenopus laevis* oocytes. RNA fractions inducing the oocytes to produce a factor capable of supporting murine stem cell proliferation, were used for synthesis of cDNA as described above, cDNA was tailed with dC residues and inserted in the PstI site of pUC9. mIL-3 clones were identified using-synthetic oligonucleotides (from published mIL-3 sequence, 11). Insert of pL101 was purified on polyacrylamide gel and used for screening of the human cDNA library. Probe DNA was labeled using the random primer method (38). Potential positive plaques were rescreened and plaque purified. In this way four clones were identified, including phage D11.

Sequencing of cDNA Clones.

Recombinant phages were grown at large scale and purified, cDNA inserts were removed from the phage arms by digestion with EcoRI and purified on polyacrylamide gel. The purified fragments were ligated into M13mp18 and pTZ18R DNA digested with EcoRI and used for transformation of *E. coli* JM109. Single strand DNA was prepared and sequenced according to established procedures (39). Sequence data were analyzed using various computer programs (40–43).

The sequence obtained for the insert in phage D11 is shown in FIG. 1. This 910 bp sequence contains the entire coding region for hmulti-CSF and its signal sequence, and exhibits high homology to the murine clone pL101 in the 3' untranslated region. The homology upstream in the coding sequence is relatively more limited. As described above, the protein has a putative 19 amino acid signal sequence followed by a 133 amino acid mature protein containing two glycosylation sites (15–17 and 70–72) and two cysteine residues at 16 and 84.

The deduced amino acid sequence is the same as that encoded by the genomic DNA disclosed by Yang, Y-C, et al. (supra), except for one amino acid—that at position 8 of the putative mature protein; the Yang DNA encodes Ser the cDNA herein encodes Pro.

The intronless sequence obtained in the phage D11 can be used for procaryotic expression, as well as for expression in eucaryotic systems, as illustrated below.

EXAMPLE 2

Expression in Mammalian Cells

A. Construction of the eucaryote expression vector pLB4

Phage D11 (containing the longest cDNA insert) was digested with Hind III and BglII and subcloned in plasmid pT1 (a derivative of pTZ18R, containing some additional restriction sites in the multilinker, see Example 3A). Clones containing the phage fragment containing the cDNA insert were identified by restriction analysis. The cDNA insert was removed from this plasmid by partial digestion with EcoRI and purified by polyacrylamide gel electrophoresis. The appropriate fragment was inserted in a eucaryote expression vector (pLO) in an SV40 transcription unit.

pLO comprises: EcoRI (filled in)—PstI of pBR322 (1–755), PstI-AvaI of pBR329 (756–1849), AvaI-PvuII adapter (1850–1868), PvuII-HindIII (filled in) of SV40 (promoter) (1869–2211), PvuII-BamHI adapter containing the unique EcoRI site (2211–2251), MboI "splice fragment" of SV40 (2252–2861), BclI-BamHI (filled in) "poly A fragment" of SV40 (2862–3098), PvuII-HindIII promoter fragment of SV40 (3099–3440), HindIII-BamHI Eco gpt gene (3441–4501), MboI "splice fragment" of SV40 (4502–5111) and the BclI-BamHI (filled in) "poly A fragment" of SV40 (5112–5348).

Figure 2:
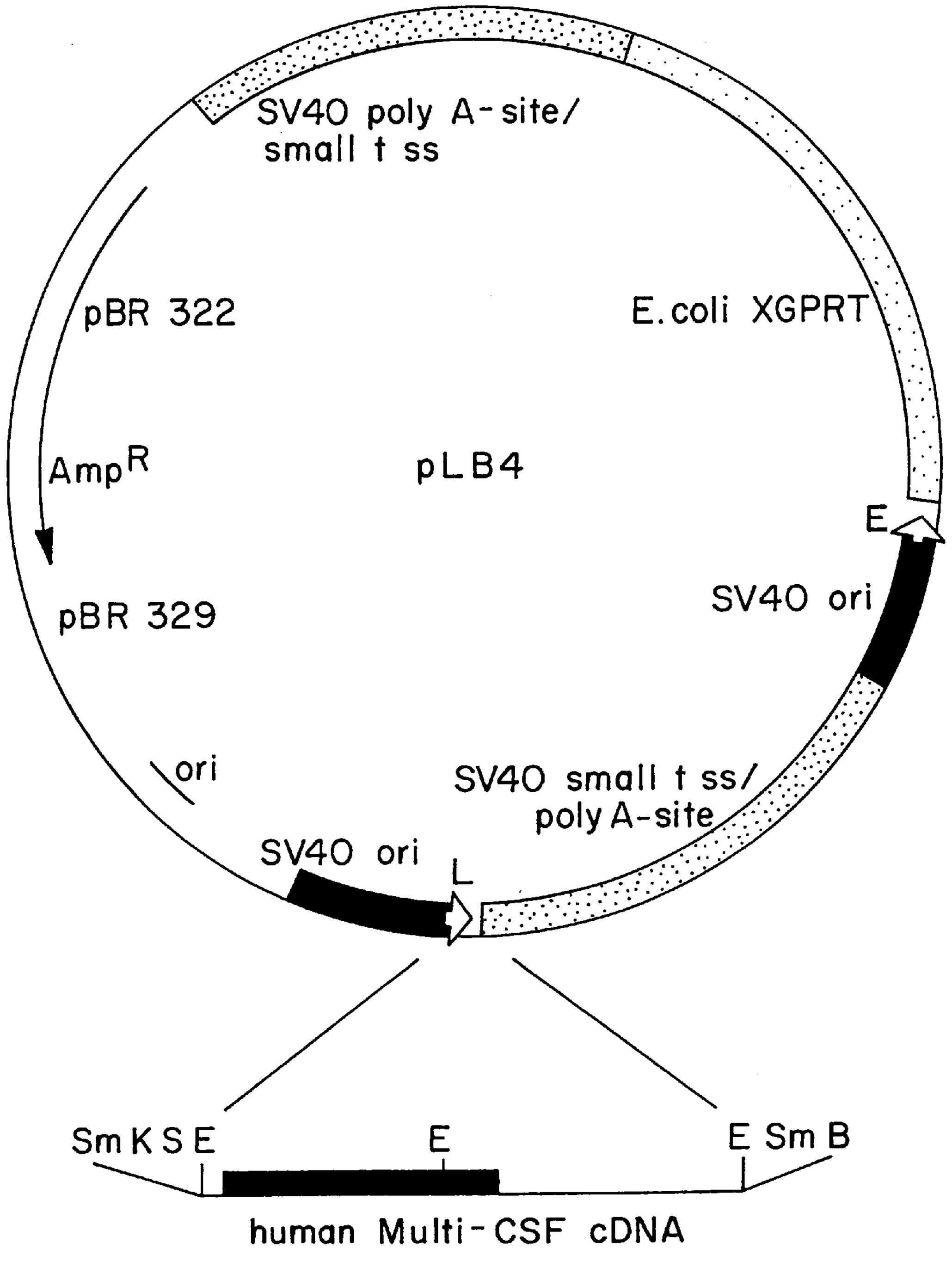
FIG. 2 shows the construction of plasmid pLB4 containing human IL-3 cDNA. E=EcoRI, Sm=SmaI, B=BamHI, S=SstI, K=KpnI.

The Eco gpt transcription unit is of no importance in transient expression of proteins in COS 1 cells. The resultant expression plasmid for hmulti-CSF was termed pLB4 and was purified on CsCl. This plasmid in *E. coli* was deposited with the Centraal Bureau of Schimmelcultures (CBS), Baarn, the Netherlands, under the provisions of the Budapest Treaty on Dec. 12, 1986 under CBS 568.86. The construct is shown in FIG. 2.

B. Expression of hmulti-CSF in COS 1 Cells and Bioassays.

pLB4 DNA was transfected to COS 1 cells using the calcium phosphate coprecipitation method (45). Cells were cultured for 48–72 hours in alpha medium containing 10% fetal calf serum. The culture medium was recovered, filtered and used in assays for establishing its biologic activity. Human bone marrow progenitor colony assays and acute myeloid blasts colony and proliferation assays were performed as follows. Bone marrow was obtained from hematologically normal adult volunteers by posterior iliac crest puncture following informed consent. The mononucleated cells were separated by density gradient centrifugation on a Ficoll gradient (Nijegaard and Co., Oslo, Norway), washed and resuspended in Hanks balanced salt solution (HBSS). Myeloid cells and T-lymphocytes were then removed. For this purpose, marrow cells were lysed following incubation with monoclonal antibodies OKT-3 (CD3; Ortho, Ravitan, N.Y.) and Vim 2 (myelo-monocytic cells, 46) at saturating concentrations in the presence of rabbit complement (40%; 30 minutes, 25°C.) according to established procedures (47). The cells were washed two times in HBSS, resuspended in Iscove's modified Dulbecco's medium (IMDM) and cultured in the presence of autologous plasma according to Fauser and Messner (16), as described before (48), at a concentration of 1.5–3x$10^4$/ml. Erythropoietin 1 U/ml (sheep, step III, Connaught, Willowdale, Canada) and, COS/pLB4-CM were added as growth stimulating activities. Results of standard cultures with phytohaemagglutinin stimulated leukocytes CM (PH-LCM) in direct comparison with COS/pLB4 CM are also given. Sixty percent of the colonies were plucked and identified by microscopical analysis. The CM from COS cells transfected with the vector without insert (pLO) failed to stimulate colony formation by itself.

Figure 3:
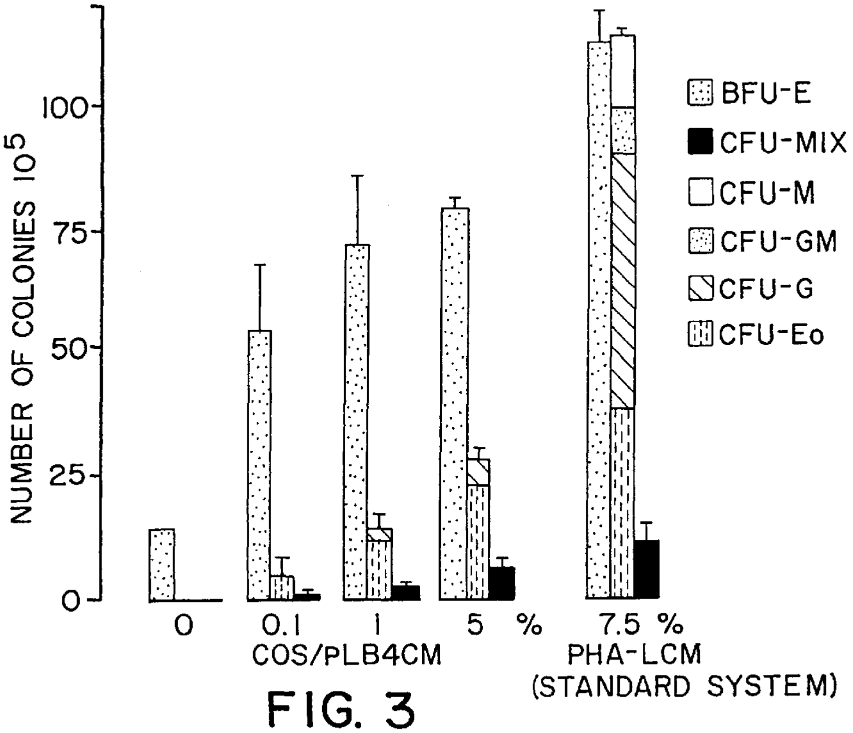
FIG. 3 shows the biological activity of COS/pLB4 CM on human bone marrow progenitors. The mean numbers of erythrdid (BFU-E), granulocyte-macrophage (CFU-GM), granulocyte (CFU-G), eosinophil (CFU-Eo), macrophage (CPU-M) and mixed (CFU-MIX) colonies (±SD) are shown for duplicate cultures stimulated with graded volumes of COS/pLB4 CM.

The results are shown in FIG. 3. As shown in the figure, the mean numbers of erythroid (BFU-E), granulocyte-macrophage (CFU-GM), granulocyte (CFU-G), eosinophil (CFU-Eo), macrophage (CFU-M) and mixed (CFU-MIX) colonies (±SD) are shown of duplicated cultures stimulated with graded volumes of COS/pLB4 CM.

Induction of AML Proliferation (see FIG. 4).

Figure 4A:
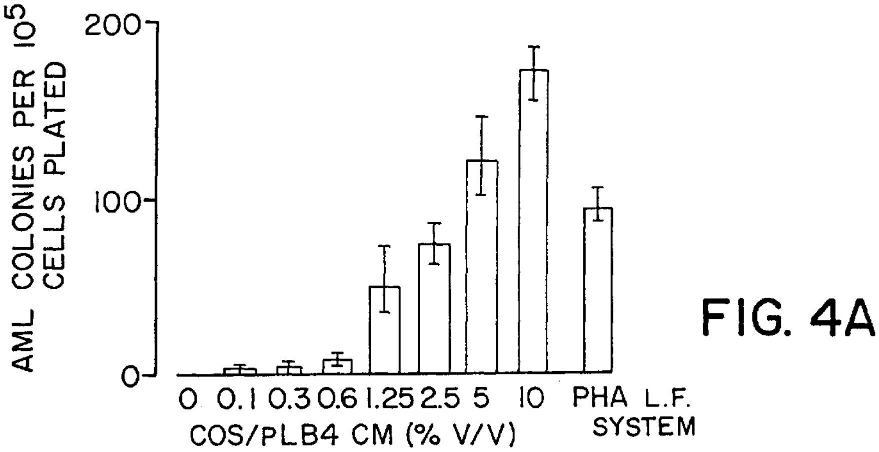
FIG. 4 shows induction of AML proliferation by COS/pLB4 CM as assessed in a colony culture assay (panel A) and in a DBA synthesis ($^3$H-TdR incorporation) assay (panel B).
Figure 4B:
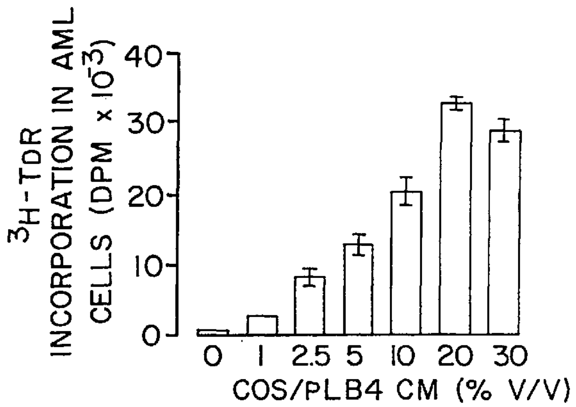

AML blasts were purified using a bovine albumin (BSA) density gradient. Residual T-lymphocytes were removed from the AML samples by E rosette sedimentation (17, 49, 50). AML (patient 1) colony formation was determined not only in the established PHA leukocyte feeder (PHA 1.f) system, but also in a modified version of the technique in which the leukocytes were replaced by COS/pLB4 CM, permitting assessment of its colony-stimulating activity (17, 18, 49, 50) as shown in FIG. 4A. All experiments were performed in triplicate. DNA synthesis of AML blasts (patient 2) was assayed by thymidine uptake as described (51) with results shown in FIG. 4B. Both assays showed a dose dependent relationship to COS/pLB4 CM added. Addition of control COS medium did not affect AML proliferation in either assay.

C. Construction of eucaryotic expression vector pLB4/BPV

In order to establish stable cell lines expressing human IL-3, C127 cells (ATCC CRL 1616) were transfected with a derivative of pLB4. This derivative was constructed by insertion of the entire BPV-1 genome (69) into pLB4 by the following strategy. The BPV-1 BamHI fragment was excised from the vector pdBPV-MMTneo (342–12) (70). The BamHI sticky ends were filled in using Klenow polymerase. Then the vector pLB4 was cleaved at the unique EcoRV site within the Eco gpt gene. Subsequently, the blunt-ended BPV-1 fragment was cloned into the EcoRV cleaved pLB4, resulting in the vector pLB4/BPV which is able to replicate in C127 cells. pLB4/BPV was transfected to C127 cell using the calcium phosphate precipitation method (45). The transfected cells were cultured for 16 days, after which foci were picked from the culture dishes. Several independent cell lines were established. The pLB4/BPV vector appears to be stably maintained within the cells, as judged by Southern blotting of Hirt extracts (71) of several cell lines. Conditioned culture medium was tested for IL-3 activity using the AML proliferation assay. The stable cell lines produce active human IL-3.

EXAMPLE 3

Construction of *E. coli* Expression Vectors

A. Construction of pGB/IL-301 (see FIGS. 5, 6, 7 and 8)

For construction of *E. coli* expression vectors, the following modifications were performed according to standard procedures (36).

Figure 5:
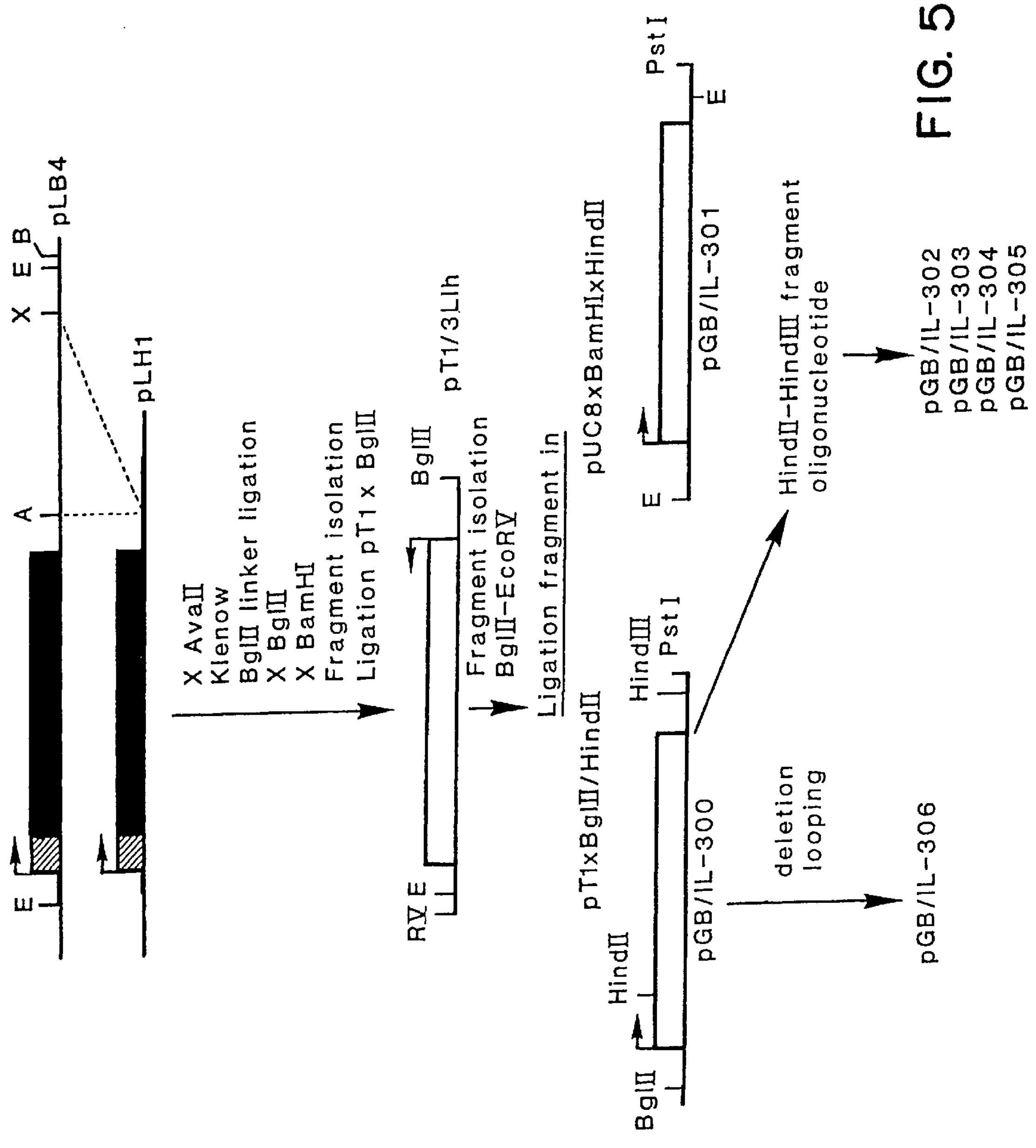
FIG. 5 shows a construction diagram of the *E. coli* expression vectors pGB/IL-301, GB/IL-302, pGB/IL-303, pGB/IL-304, pGB/IL-305 and pGB/IL-306. In this Figure X stands for XhoI, E for EcoRI, B for BamHI and A for AvaI site.

1. The 3'-terminal noncoding sequences between the AvaI site (position 541) and the XhoI site (position 856) in pLB4 were deleted by fusion of the DNA fragments following filling of the sticky ends with Klenow enzyme (FIG. 5).

2. For introduction of the hmulti-CSF insert into a bacterial expression sector, the following steps were performed. The pLH1 vector was digested with AvaII and the recessed ends filled with Klenow polymerase. Following ligation of a BglII linker (CAGATCTG), the DNA was digested with BglII and BamHI. The BglII-BamHI hmulti-CSF fragment was purified on polyacrylamide gel and subcloned in the BglII site of pT1, a derivate of pTZ18R (Pharmacia) modified in the multiple cloning site (see FIG. 6). Two clones were obtained, which had the insert in the opposite orientation with respect to the lacZ promoter (see FIG. 5). Inserts of these two clones were isolated on polyacrylamide gel following digestion with BglII and EcoRV and subcloned in pT1 digested with BglII and HindII. The junction of the BglII linker and the hmulti-CSF DNA was verified by sequence analysis and showed a fusion of the linker to the AvaII site located at nt 1 of the cDNA clone (this AvaII site had arisen by ligation of the EcoRI linker to the cDNA molecule). Since this construct (pGB/IL-300) was not in phase with the lacZ protein, the BglII-EcoRV insert was subcloned into BamHI and HindII digested pUC8 (52). The resulting construct (pGB/IL-301, see FIGS. 5, 7 and 8) was tested for production of a lacZ/hmulti-CSF fusion protein.

Figure 7:
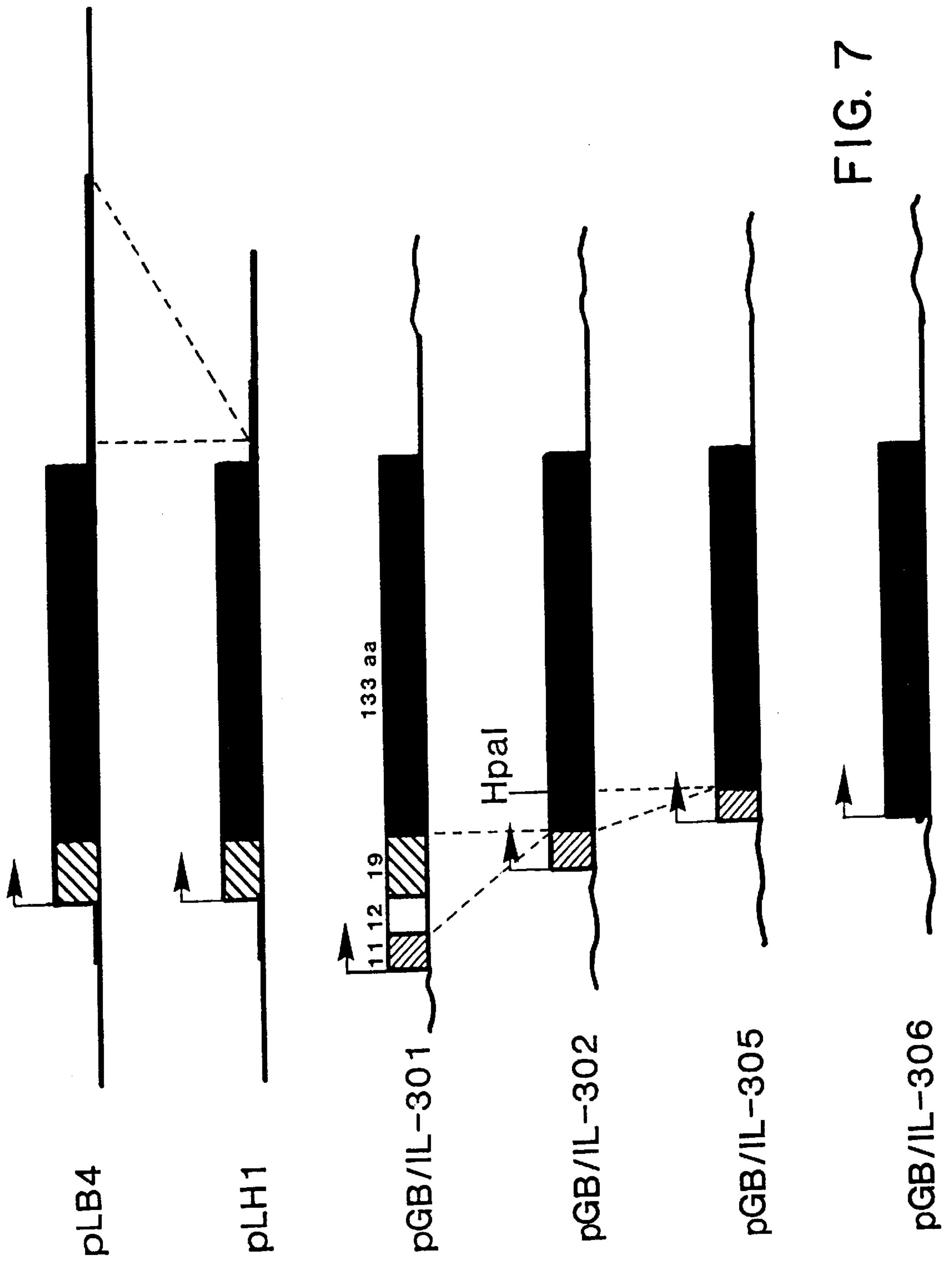
FIG. 7 shows a schematic presentation of hmulti-CSF expression clones. For the eucaryote expression plasmids pLB4 and pLH1 only the hmulti-CSF cDNA insert is shown. Leader peptide (▨) and mature hmulti-CSF protein (■) coding regions are indicated in boxes. Bacterial expression clones of hmulti-CSF (derived from pLH1) contain the lacZ and multi-linker protein coding region (▩), the 5' terminal noncoding region of hmulti-CSF (☐) and the hmulti-CSF coding region. The arrow marks the ATG startcodon used in the particular vector.

B. Construction of pGB/IL-302, pGB/IL-303, pGB/IL-304 and pGB/IL-305 (FIGS. 5, 7 and 8)

Several base changes were introduced into the coding sequence for the N-terminal part of the fusion proteins by introduction of synthetic oligo nucleotides into pGB/IL-300. The new expression vectors, called pGB/IL-302, pGB/IL-303 and pGB/IL-3024 were constructed as follows: the HindII-HindIII fragment of pGB/IL-300 was isolated on agarose gel and ligated to a synthetic oligonucleotides comprising the nucleotides 99–137 of hmulti-CSF and a 5' terminal SalI recognition sequence and inserted into pTZ18R digested with SalI and HindIII. The sequence of several clones was established. Indeed, several base changes were observed, resulting in modifications of the hmulti-CSF protein. Inserts of several clones were transferred to pUC8 for expression of the lacZ fusion protein (pGB/IL-302, pGB/IL-303). Clone pGB/IL-304 was made in fase with lacZ by ligation of the SalI site following filling of recessed ends with Klenow. Construction was verified by PvuI digestion. Several clones lacked a synthetic oligonucleotide and were found to be fused in frame to the lacZ protein. One example of these clones was called pGB/IL-305.

C. Construction of pGB/IL-306 (see FIGS. 5, 7 and 8)

An expression vector coding for a protein lacking the lacZ N-terminal amino acids was made from pGB/IL-300 by deletion looping as described in (53). The synthetic oligonucleotide comprised 22 nucleotides upstream of the pTZ lacZ gene including the ATG start codon and the first 24 nucleotides coding for mature IL-3. This plasmid was called pGB/IL-306 (FIGS. 5, 7 and 8).

E. coli strains containing the plasmids pGB/IL-300, pGB/IL-301 and pGB/IL-302 were deposited with CBS on Jul. 13, 1987 under CBS 377.87, CBS 379.87 and CBS 378.87, respectively.

FIG. 8 shows the sequence of fusion regions for the various plasmids constructed. The sequence of the clones is given from the start of the lacZ protein coding region in either pUC8 or pTZ18R (lower case letters) and of the hmulti-CSF coding region (upper case letters) and up to the ClaI site at position 158. Mutations in the hmulti-CSF DNA sequence are underlined, resulting in $trp^{13} \rightarrow arg^{13}$ (pGB/IL-302,); $leu^9 \rightarrow pro^9$ and $trp^{13} \rightarrow arg^{13}$ (pGB/IL-303); $met^3 \rightarrow thr^3$ and a silent change (pGB/IL-304).

In the priority application EP 87201322.2, filed on Jul. 13, 1987, other designations were used for these plasmids as follows:

pGB/IL-300=pT-hIL3;
pGB/IL-301=pUC/hmulti;
pGB/IL-302=pUC/hmultiΔ1A;
pGB/IL-303=pUC/hmultiΔ1B;
pGB/IL-304=pUC/hmultiΔ1C;
pGB/IL-305=pUC/hmultiΔ2;
pGB/IL-306=pTZ/hmulti;

D. Expression of lacZ/hmulti-CSF Fusion Proteins and Mature, hmulti-CSF in E. coli E. coli strains (JM 109) carrying various expression vectors were grown in LB medium containing 50 μg/ml of ampicillin at 37° C. until an optical density of 0.5 at 550 nm was reached. Subsequently IPTG (isoproyl beta-D-thiogalactoside, Pharmacia) was added to the culture to a final concentration of 1 mM and incubation was continued for 3–4 hours.

Plasmids pGB/IL-306 and pGB/IL-302 were also transformed to E. coli DH1 (wild type lacZ operon). Those strains were grown in LB medium or 2× TY medium containing 50 μg/ml of ampicillin at 37° C. for 16 hours.

Bacteria were collected by centrifugation and sonicated in buffer containing 0.1 M Tris/HCl, pH 8.0; 5 mM EDTA 0.2% Nonidet P40 (NP-40) and 1 mM phenylmethylsulfonyl fluoride (PMSF) and centrifuged for 30 min at 20,000×g. Polyacrylamide gel electrophoresis of the pellet and supernatant fractions showed that the bulk of the hmulti-CSF proteins is stored in the bacteria in an insoluble form.

Figure 9:
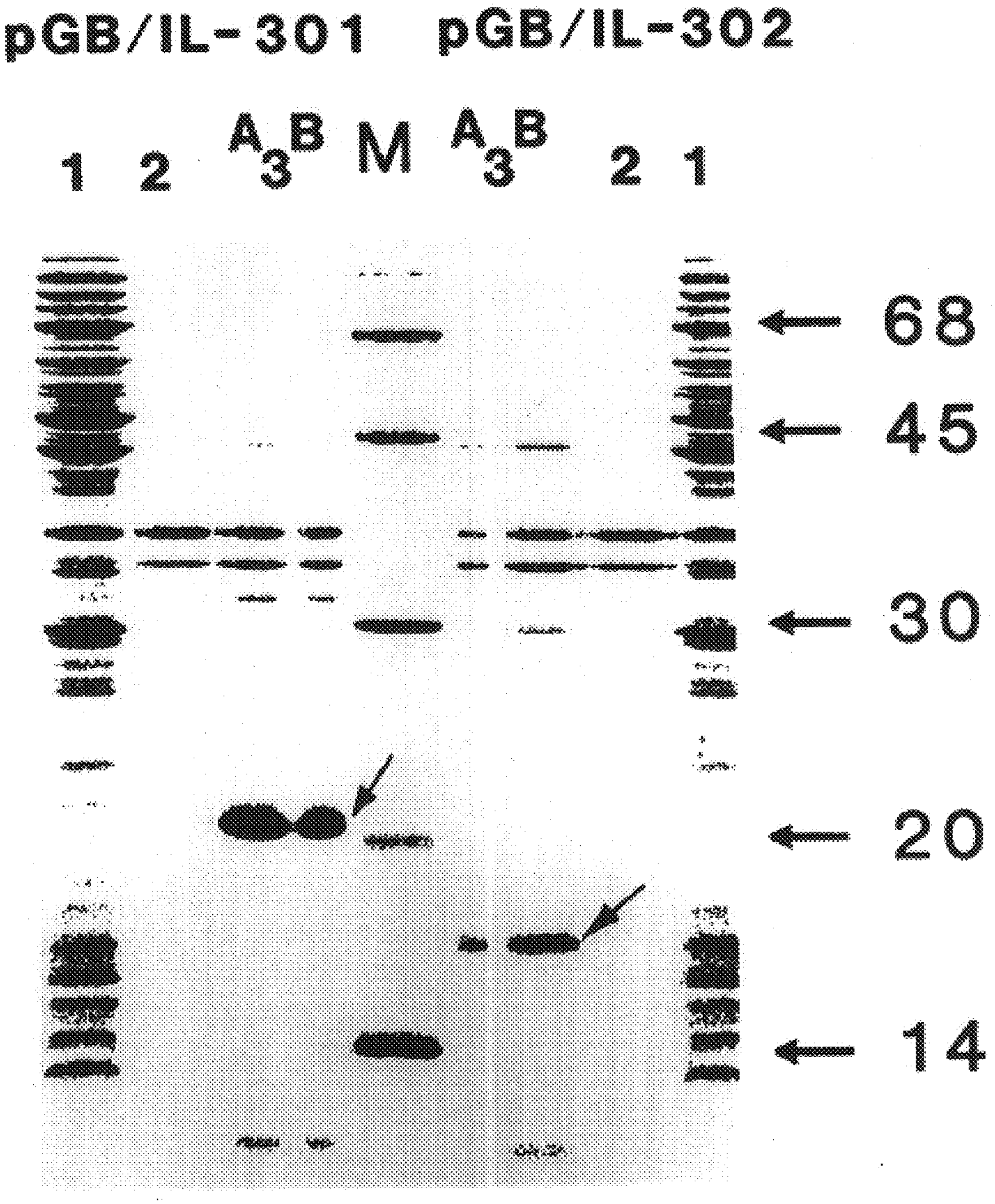
FIG. 9 shows polyacrylamide gel-electrophoresis of bacterial hmulti-CSF produced from bacteria containing pGB/IL-301 and pGB/IL-302.

The pellet was re-extracted with 0.5% NP-40 buffer and finally solubilized with 8 M urea 0.1 M Tris/HCl, pH 8.0 and 5 mM dithiothreitol. Thus, an extensive purification of the fusion proteins was achieved (FIG. 9).

As shown in the figure, inclusion bodies from bacteria (E. coli) containing pGB/IL-301 and pGB/IL-302 were isolated as described. Lanes 1 show the 0.2% NP40 supernatant (sample corresponds to 0.1 ml of the original bacterial culture). Lanes 2 show the 0.5% NP40 supernatant (0.2 ml) and lanes 3 the pellet solubilized in 8M urea buffer (A: 0.05 ml; B: 0.2 ml). The proteins were separated on a 13.5% SDS-polyacrylamide gel and stained with Coomassie Brilliant Blue. Molecular weights (in kd) of marker proteins (lane M) are denoted on the right. The human multi-CSF fusion proteins are indicated by arrows. The fusion protein encoded by pGB/IL-301 has a MW as expected of about 20 kd; that produced from pGB/IL-302, of about 16 kd.

E. Determination of Biological Activity of Bacterial hmulti-CSF Preparations.

Figure 10:
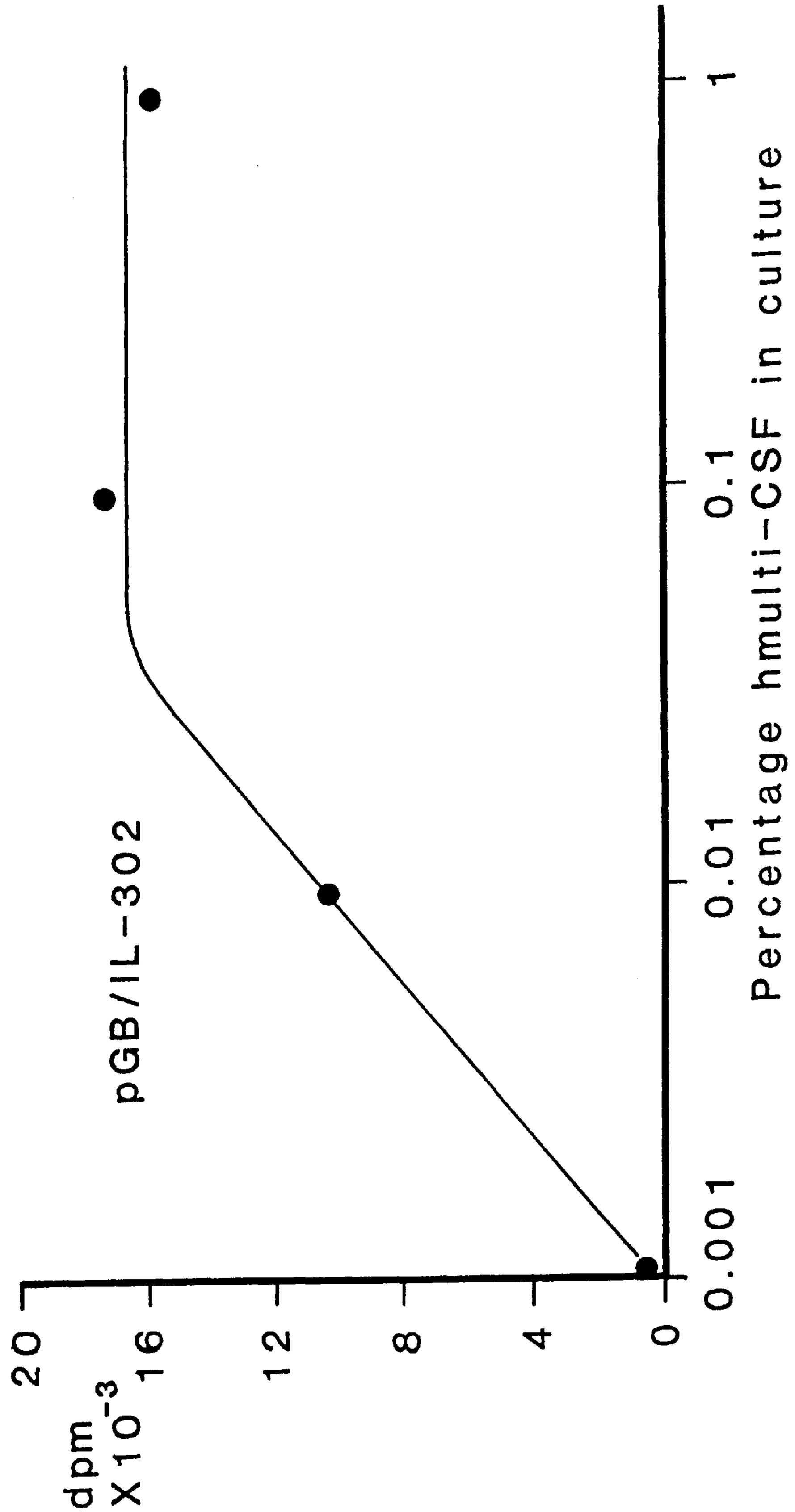
FIG. 10 shows the titration of hmulti-CSF fusion protein on AML blast cells.

Bacterial protein preparations were diluted in alpha medium containing 1% bovine serum albumin, filter sterilized and assayed in the AML blast proliferation assay. Diluted samples were added to purified AML blasts and cultured for four days. DNA synthesis was measured using $^3H$ thymidine as described (51). One unit per ml is defined as the amount of hmulti-CSF required for half maximal proliferation of AML blasts. FIG. 10 shows this titration. Various dilutions of the urea extracted protein preparation of bacteria containing the plasmid pGB/IL-302, were assayed for the stimulation of AML blast proliferation using $^3H$-thymidine. The fusion protein concentration of this protein preparation was 33 μg/ml. Based on the presented titration curve, the activity of this preparation is 16,000 units/ml.

The amount of bacterial fusion protein in the preparations was estimated from polyacrylamide gel-electrophoresis and used for calculating specific activities.

The results are shown in the following table:

TABLE 1

Biological Activity of Bacterial hmulti-CSF Preparations

| | $Mr (\times 10^{-3})$ lacZ/hmulti (1) | ug protein per ml (2) | units per ml (3) | Specific activity units per mg IL-3 |
|---|---|---|---|---|
| pGB/IL-301 | 20 | 20 | 45 | 4,500 |
| pGB/IL-302/303 | 16 | 5 | 2400 | 480,000 |
| pGB/IL-304 | 18 | ND (4) | 18 | — |
| pGB/IL 305 | 16 | 1 | 300 | 300,000 |
| pGB/IL 306 | 15 | ND | 70 | ND |

(1) Approximate molecular weights are estimated from the DNA sequence of the fusion protein (FIG. 8).
(2) IL-3 concentrations were estimated on SDS-polyacrylamide gel and calculated per ml of starting culture.
(3) Activity of urea solubilized protein was determined in the AML proliferation assay and is expressed per ml of starting culture.
(4) Not determined.

From these results it was concluded that human multi-CSF expressed as a fusion protein in E. coli was obtained in biologically active form. The results show that changes introduced into the N-terminus of the fusion proteins may influence the specific activity of these proteins.

EXAMPLE 4

Preparation of Antibody Preparations Capable of Immunospecific Reaction with Human IL-3 Protein A. Polyclonal Rabbit Anti-Human IL-3 Antiserum.

A preparative gel was made from a lysate of E. coli containing the plasmid pGB/IL-301. The 20 kd band with the IL-3 fusion protein was sliced out, minced in saline with a mortar and emulsified in a 1:1 ratio in Complete Freund's Adjuvant containing 1 mg of *Mycobacterium tuberculosis* H37RA per ml. New Zealand White rabbits (spf) were immunized with 1 ml of the emulsion (with ±100 μg IL-3 fusion protein) divided over 5 injection sites (2× i.m. in the thighs, 3× s.c. on the back). Booster injections of the same antigen in Incomplete Freund's Adjuvant were given at week 2, 4 and 6. Serum was collected at week 8 by venapuncture from the ear.

One volume of serum was absorbed with 9 volumes of sonicated pUC8 containing *E. coli* (overnight at 4° C.) to remove nonspecific antibodies. Immunoblotting of all IL-3 constructs made in *E. coli, B. licheniformis, B. subtilis, S. cerevisiae* and *K. lactis* showed immunospecific reaction with the absorbed sera at a dilution of 1 in 6500.

Figure 11:
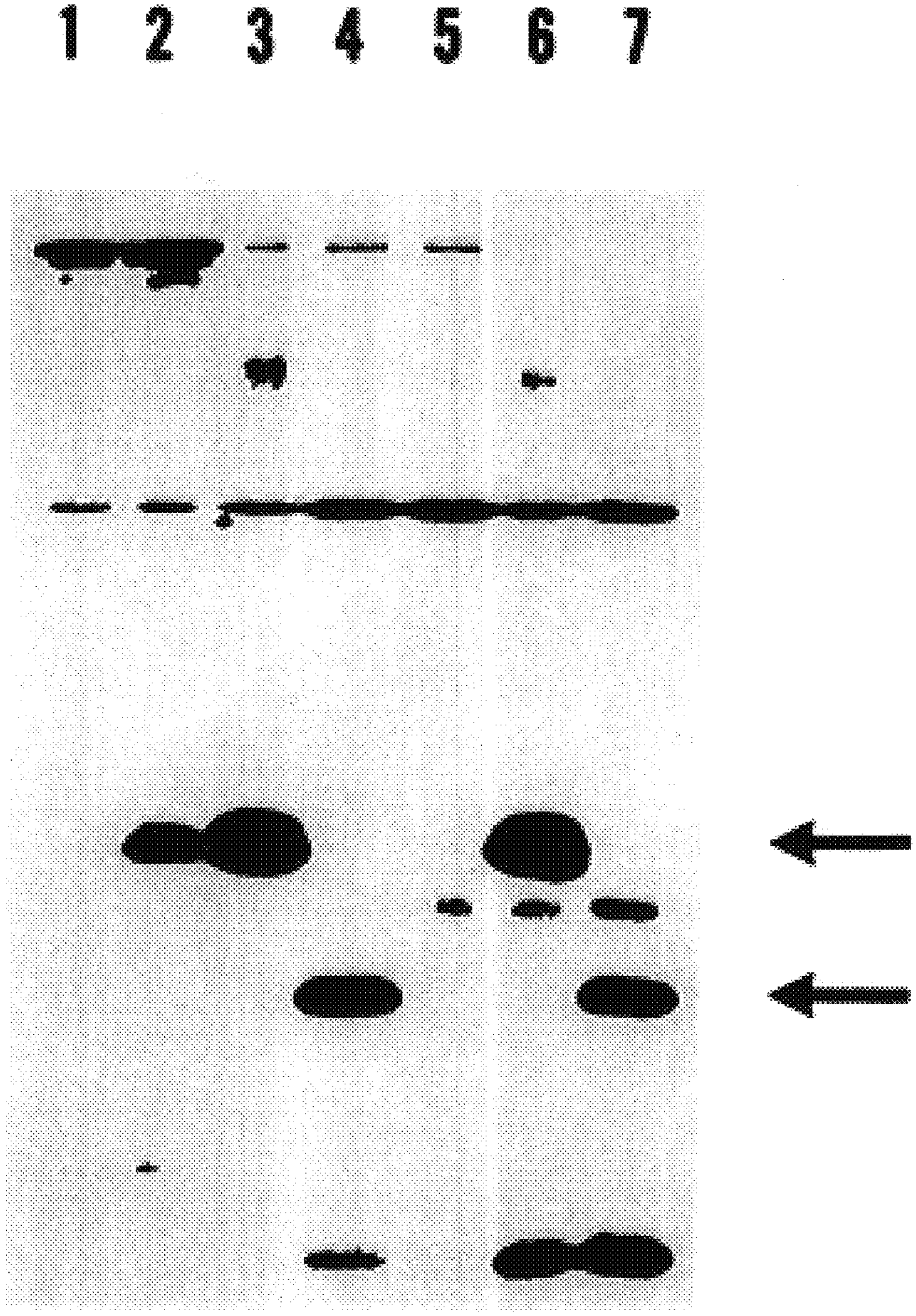
FIG. 11 shows a Western blot demonstrating the IL-3 specific reaction of rabbit antisera raised against the 21 kd protein isolated from a lysate of *E. coli* transformed with pGB/IL-301.

Some of these results are shown in FIG. 11. The proteins were isolated from the recombinant hosts as described above and were separated on a 13.5% polyacrylamide gel and blotted onto a nitrocellulose membrane. Lane 1: *E. coli* containing pTZ18R (control); Lane 2: pGB/IL-301; Lane 3: pGB/IL-301; Lane 4: pGB/IL-302; Lane 5: pUC19 (control); Lane 6: pGB/IL-301; Lane 7: pGB-IL-302. Lanes 6 and 7 show proteins present in the pellet after the sonification of the bacteria. Lanes 3, 4 and 5 show proteins present in the pellet after the first washing step. Lanes 1 and 2 show the final urea-solubilized protein fractions.

The arrows show the fusion proteins (of the expected size) expressed from pGB/IL-301 and pGB/IL-302.

Figure 12B:
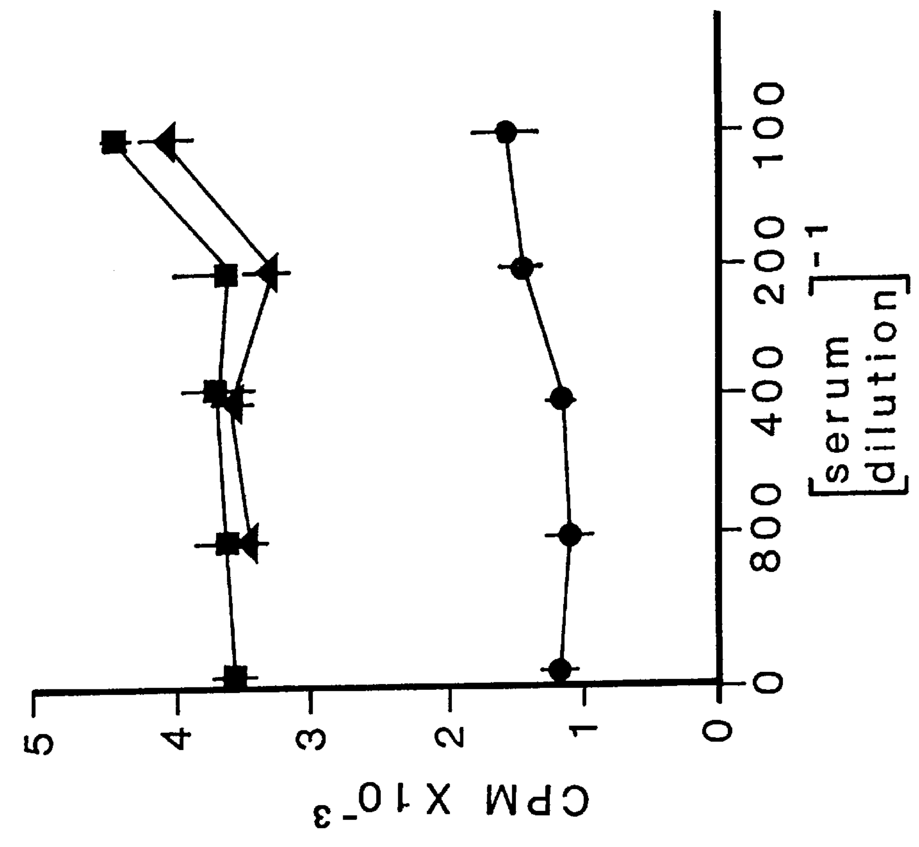
FIG. 12 shows the effect of the antisera of FIG. 11 on IL-3 activity.
Figure 12A:
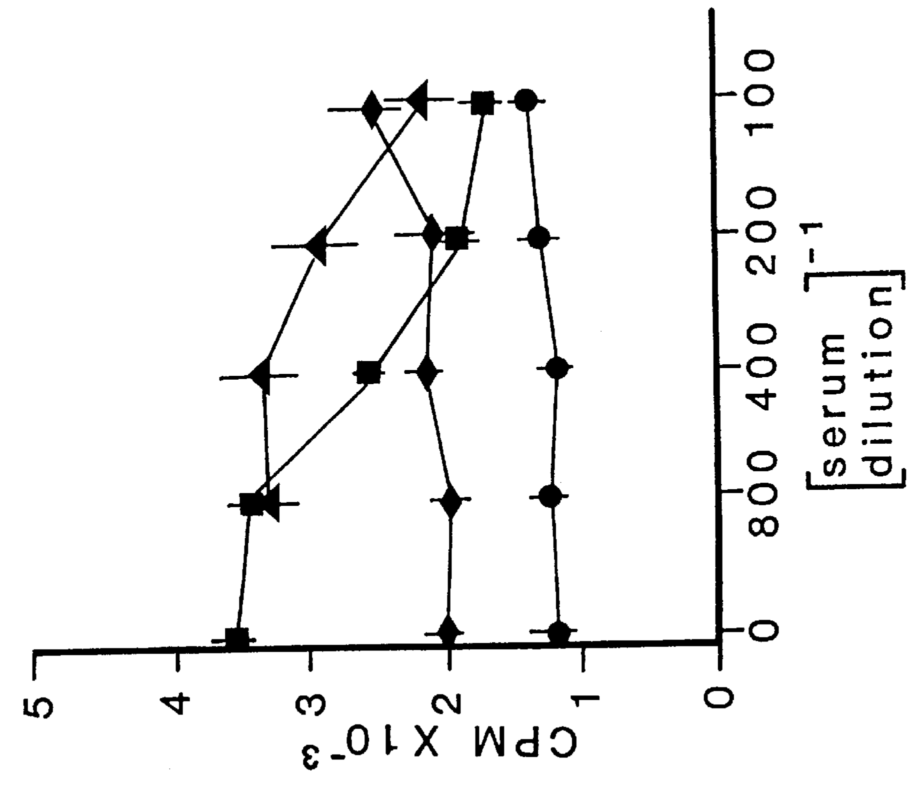

FIG. 12A shows the inhibition of IL-3 dependent proliferation of AML blast cells by anti-IL-3 antiserum. FIG. 12B shows that the preimmune serum does not affect the action of IL-3 on AML blast cell proliferation. In both panels, ▲=IL-3 at 10 U/ml; ■=IL-3 at IU/ml; ●=control, no addition.

FIG. 12A shows IL-3 dependent growth in the AML blast proliferant assay (51) was inhibited by the sera in a dose dependent manner: FIG. 12B shows preimmune sera do not have this effect. As control, GM-CSF dependent growth was unaffected by these sera in the same assay (FIG. 12A where ♦=GM-CSF at 100 U/ml.)

B. Monoclonal Mouse Anti-Human IL-3 Antibodies

Balb/C mice were immunized with 3×0.1 ml (s.c.) of the same emulsion as used for the rabbits. A booster (0.1 ml imp.) of antigen in Incomplete Freund's Adjuvant was given at week 2 and three days later spleen lymphocytes were fused with SP2/0 myeloma cells according to standard procedures (65). Hybridoma supernates were screened in the Enzyme Lined Immunosorbent Assay, using a lysate of *E. coli* pGB/IL-302 (containing the 17 kd IL-3 fusion product) as a positive control and a lysate of *E. coli* pUC8 as negative control. In total, 29 IL-3 hybridoma cultures secreting antibodies specific for IL-3 were selected and stabilized.

EXAMPLE 5

Construction of Bacillus Expression Vectors

General cloning techniques were used (36).

Figure 13:
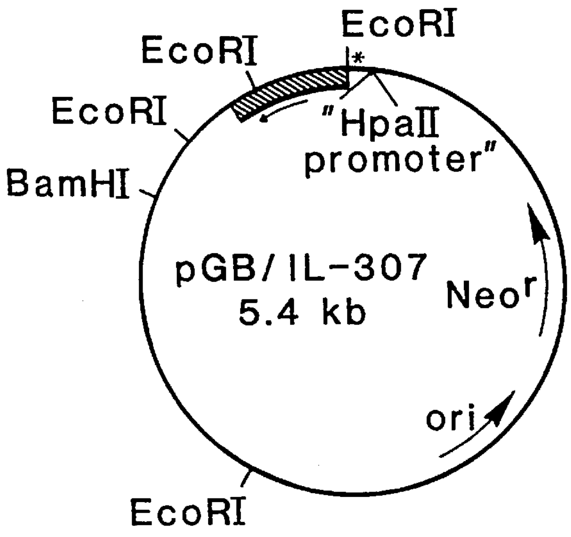
FIG. 13 (SEQ ID NO:19) shows a schematic representation of plasmid pGB/IL-307. The box (▩) indicates the human IL-3 coding sequence. The N-terminal amino acids of the fusion protein are depicted below the drawing.

A. Construction of pGB/IL-307 (FIG. 13)

For construction of pGB/IL-307 the SmaI fragment of pLB4 carrying the hmulti-CSF gene, was ligated into PvuII digested pUB110 (54). After transformation to competent cells (56) of DB105 (a spo- derivative of the protease deficient strain DB104 (55)), two clones were obtained, as expected: the fragment was cloned in both orientations. The plasmid that harbored the fragment in the correct orientation with respect to the so-called "Hpa II promoter" (57) was called pGB/IL-307. In this case a fusion protein will be made (see FIG. 13).

B. Construction of pGB/IL-310

A hmulti-CSF expression plasmid was prepared as described below.

Figure 14:
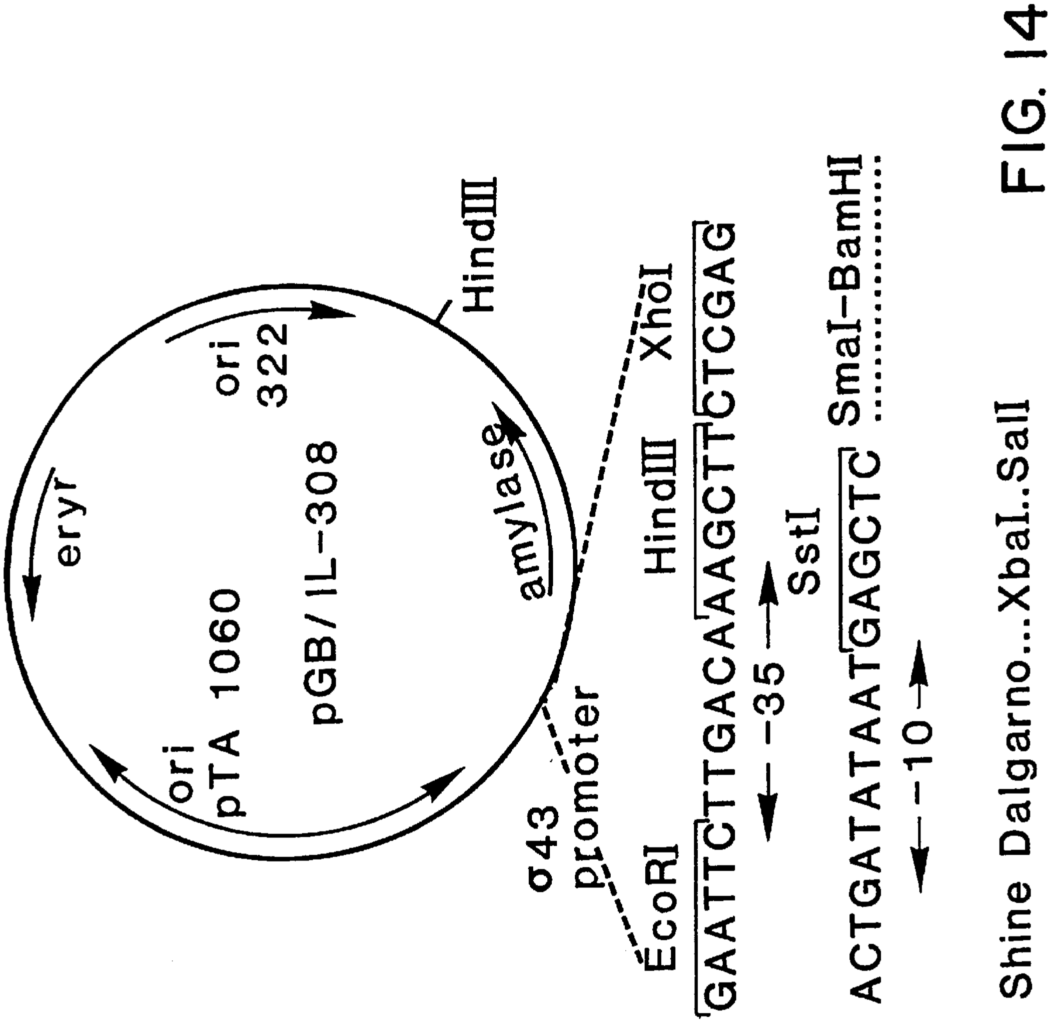
FIG. 14 (SEQ ID NO:20) shows a schematic representation of plasmid pGB/IL-308. The nucleotide sequence of the promoter region is depicted below the drawing.

1. Promoter cloning (FIG. 14).

For expression in Bacillus a synthetic $\sigma^{43}$ promoter as described (58) is used (the promoter used to be called $\sigma^{55}$).

Plasmids pPROM55s (58), the promoter containing plasmid, and pGPA14 (59) were digested with EcoRI and XbaI. The promoter fragment was ligated into the vector fragment, which had been purified on an agarose gel. After transformation to *E. coli* (JM 101), the correct plasmid was obtained and called pGB/IL-308 (FIG. 14).

Figure 15:
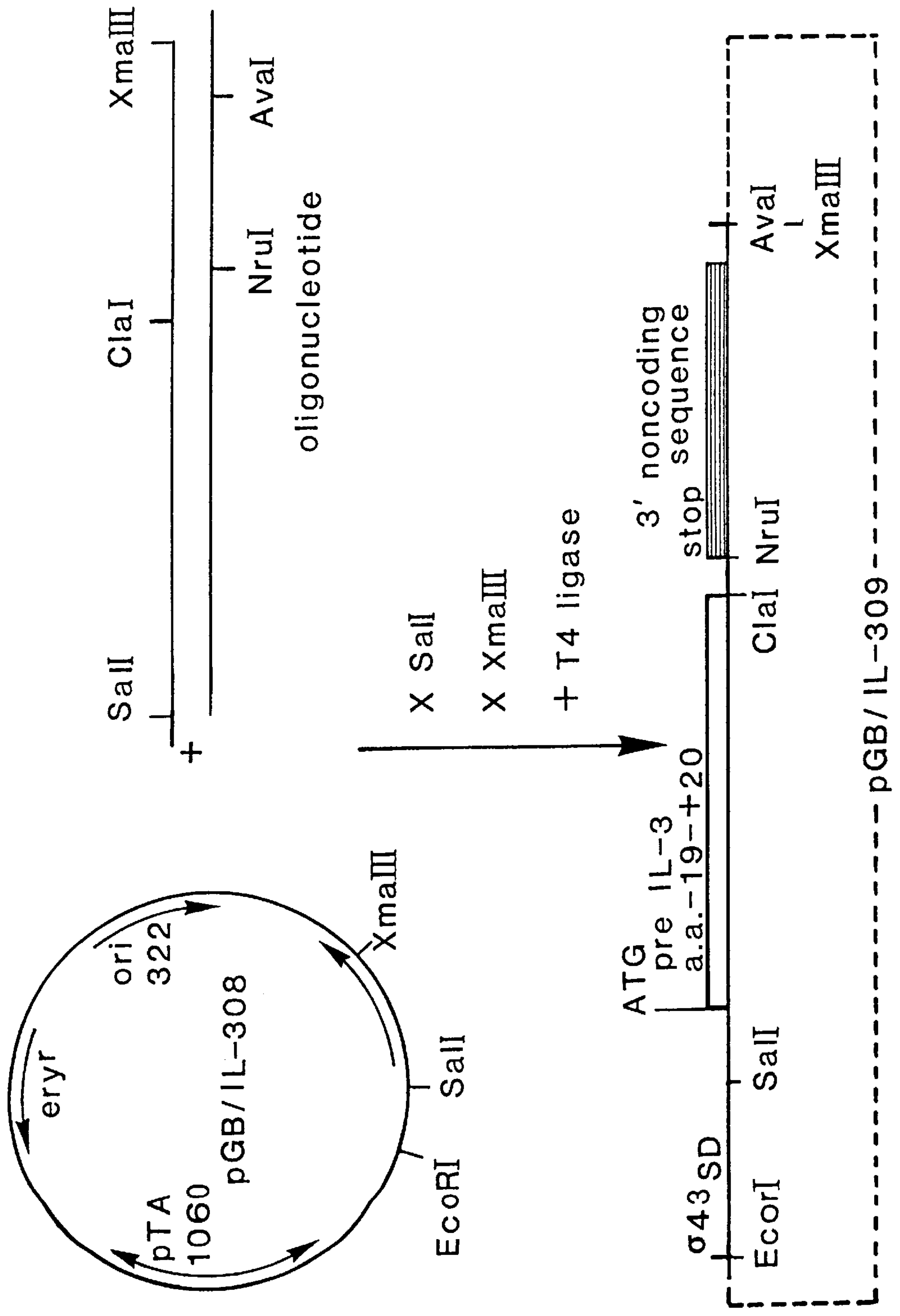
FIG. 15 shows the construction of plasmid pGB/IL-309. The first box (☐) indicates a part of the human IL-3 sequence, viz. the signal sequence plus 20 amino acids of the mature protein. The other box (≡) indicates part of the 3' noncoding region of the IL-3 cDNA sequence.

2. Introduction of a synthetic oligonucleotide into pGB/IL-308 (FIG. 15).

A synthetic oligonucleotide comprising the nucleotides 39–158 and 484–546 of hmulti-CSF, a 5' terminal SalI recognition sequence and a 39 terminal XmaIII site was ligated into SalI-XmaIII digested pGB/IL-308. The ligation mixture was introduced into JM101. After analysis of a number of transformants, the correct plasmid was found, pGB/IL-309.

Figure 16:
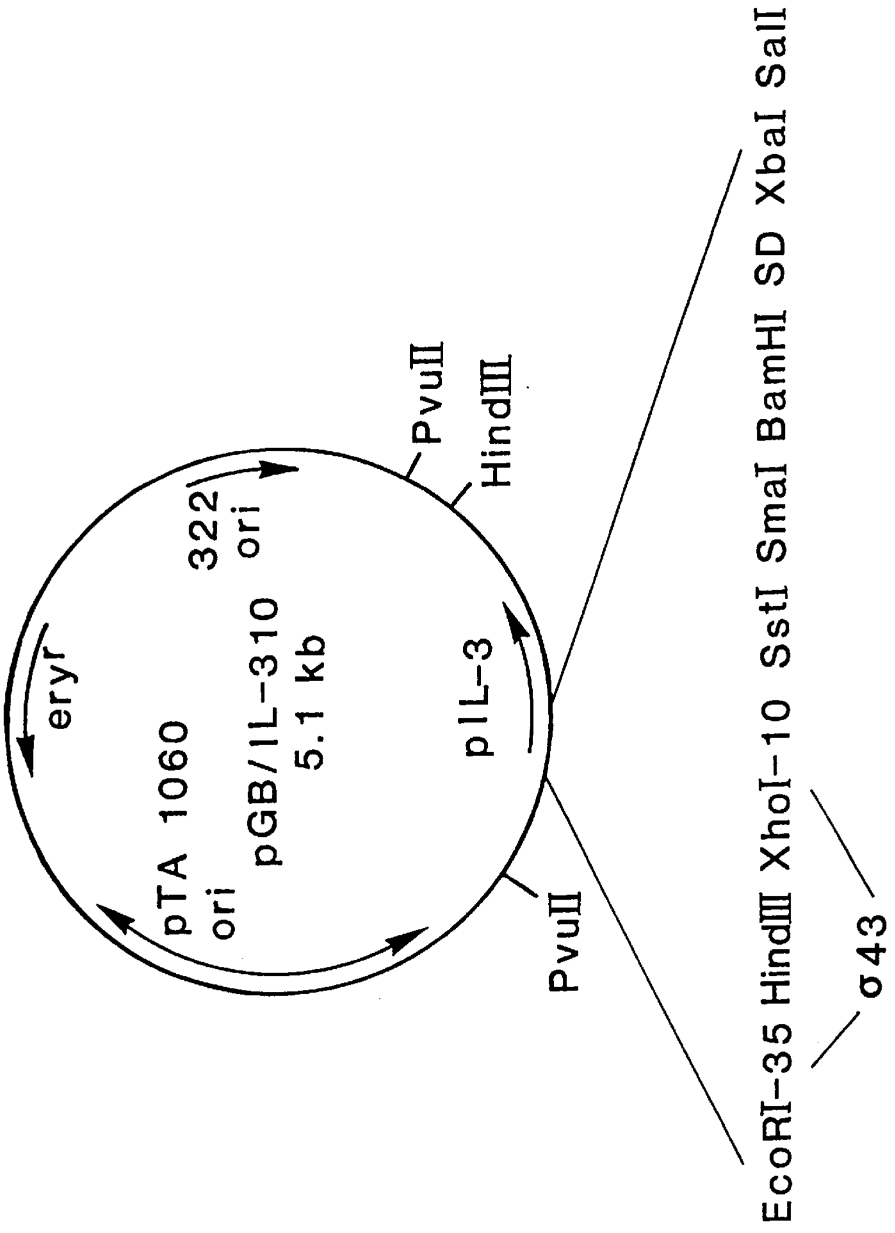
FIG. 16 is a schematic representation of plasmid pGB/IL-310.

3. Introduction of hIL3 (FIG. 16).

After transformation to and isolation from *B. subtilis* DB105, the plasmid pGB/IL-309 was digested with XmaIII. The recessed ends were filled in with Klenow polymerase, and the plasmid was cleaved with ClaI. The plasmid pGB/IL-307 was digested with AvaI, the ends filled in with Klenow and then digested with ClaI. Subsequently, the hmulti-CSF containing fragment was ligated into the pGB/IL-309 fragment and transformed to JM101. The resulting plasmid was called pGB/IL-310 (FIG. 16). This plasmid harbored the hIL-3. gene with its own signal sequence. After isolation of the correct plasmid, it was also introduced into *B. subtilis* DB105.

C. Construction of pGB/IL-311 and pGB/IL-312 (FIGS. 17, 18)

pGB/IL-310 was partially digested with HindIII and totally with PvuI. The two hmulti-CSF containing PvuII-digested with HindIII and SmaI.

FIG. 17 show& the nucleotide sequence of plasmid pBHA1. The plasmid consists of positions 11–105 and 121–215, bacteriophage FD terminator (double): positions 221–307; a part of plasmid pBR322 (viz. positions 2069–2153): positions 313–768; bacteriophage F1, origin of replication (viz. positions 5482–5943): positions 772–2571; part of plasmid pBR322, viz. the origin of replication and the beta-lactamase gene: positions 2572–2685; transposon Tn903, complete genome: positions 2719–2772; tryptophan terminator (double): positions 2773–3729; transposon Tn9, the chloramphenicolacetyltransferase gene. The nucleotides at position 3005 (A), 3038 (C), 3302 (A) and 3409 (A) differ from the wild type cat coding sequence. These mutations were introduced so as to eliminate the NcoI, BalI, EcoRI and PvuII sites: positions 3730–3804; multiple cloning site: positions 3807–7264; part of plasmid pUB110, viz. the replication function and kanamycin resistance gene (EcoRI-PvuII fragment) (66, 67): positions 7267–7331; multiple cloning site. The fragments wear put together by known cloning techniques,.e.g. filling in of sticky ends with Klenow, adapter cloning, etc. All data were derived from Genbank®, National Nucleic Acid Sequence Data Bank, NIH, USA.

Figure 18:
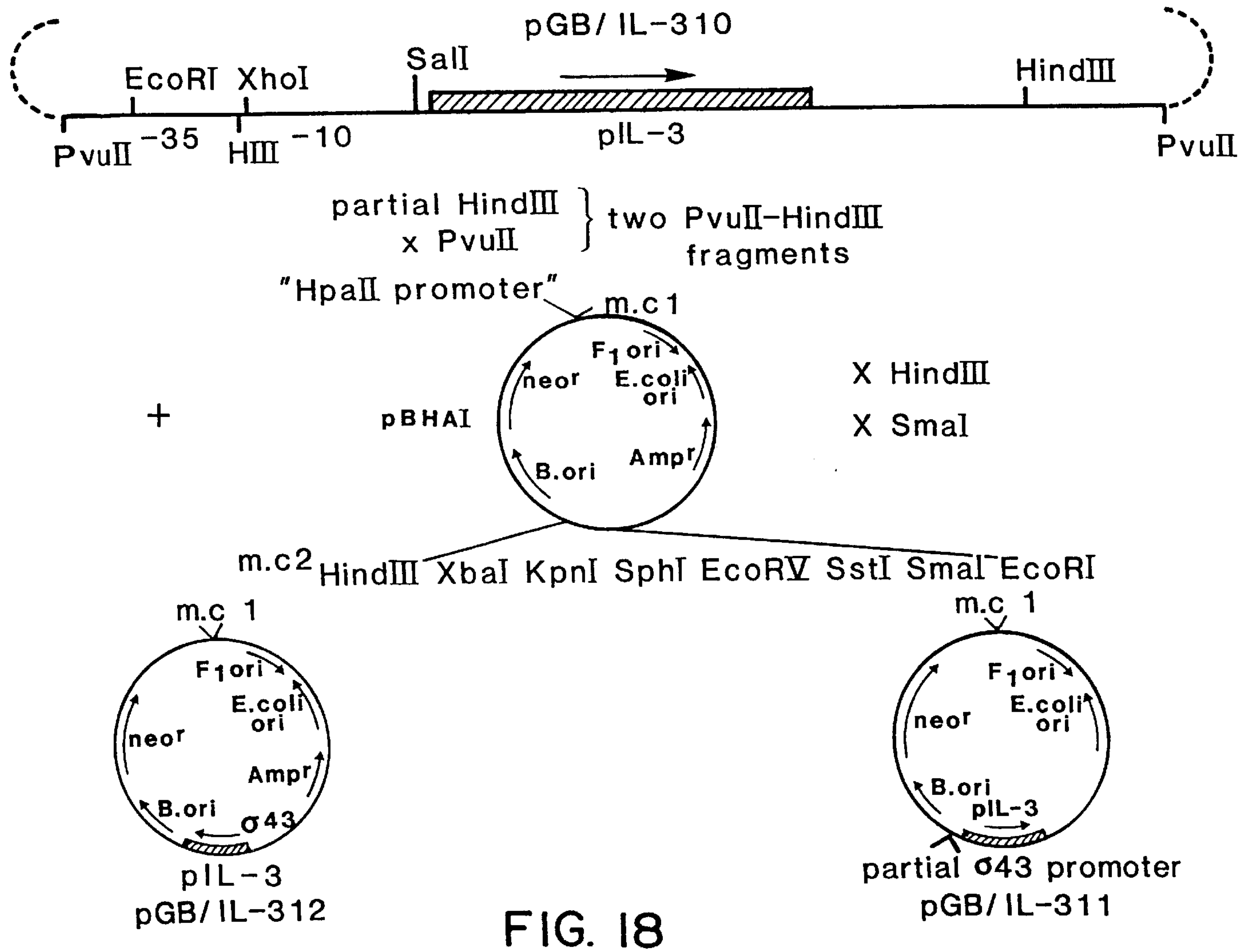
FIG. 18 shows the constriction of the plasmids pGB/IL-311 and pGB/IL-312. The box (▨) indicates the precursor human IL-3 coding region.

After transformation to JM101 and analysis of a number of ampicillin resistant colonies, two different plasmids were found: pGB/IL-312, which harbored the complete gene with complete control sequences, and pGB/IL-311, which contained the complete gene and the promoter lacking the −35 region in the other orientation (see FIG. 18).

pGB/IL-311 has been transformed to *B. subtilis* DB105 and *B. licheniformis* strain 7399 (Δamy, spo-, exo- protease negative, $rif^r$, see ref. 68).

Figure 19:
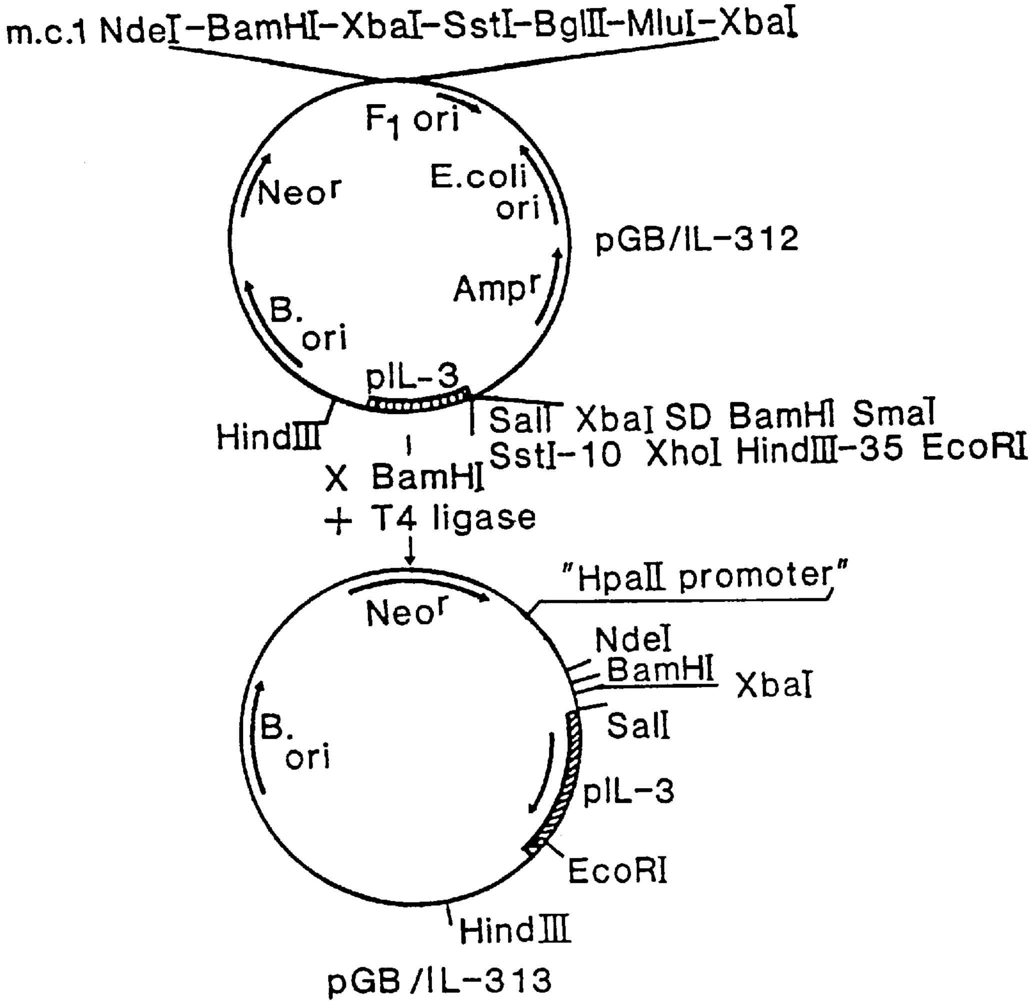
FIG. 19 (SEQ ID NO:22 & SEQ ID NO:23) shows the construction of the plasmid pGB/IL-313. The sequence at the 5' side of the IL-3 sequence is depicted below the drawings.

D. Construction of pGB/IL-313 (FIG. 19).

In order to obtain a smaller plasmid, with the hmulti-CSF gene behind the "HpaII promoter", pGB/IL-312 was digested with BamHI and religated. The ligaton mixture was transformed into DB105 competent cells. A number of neomycin resistant colonies were analysed and the correct plasmid was obtained. The plasmid was called pGB/IL-313.

Figure 20:
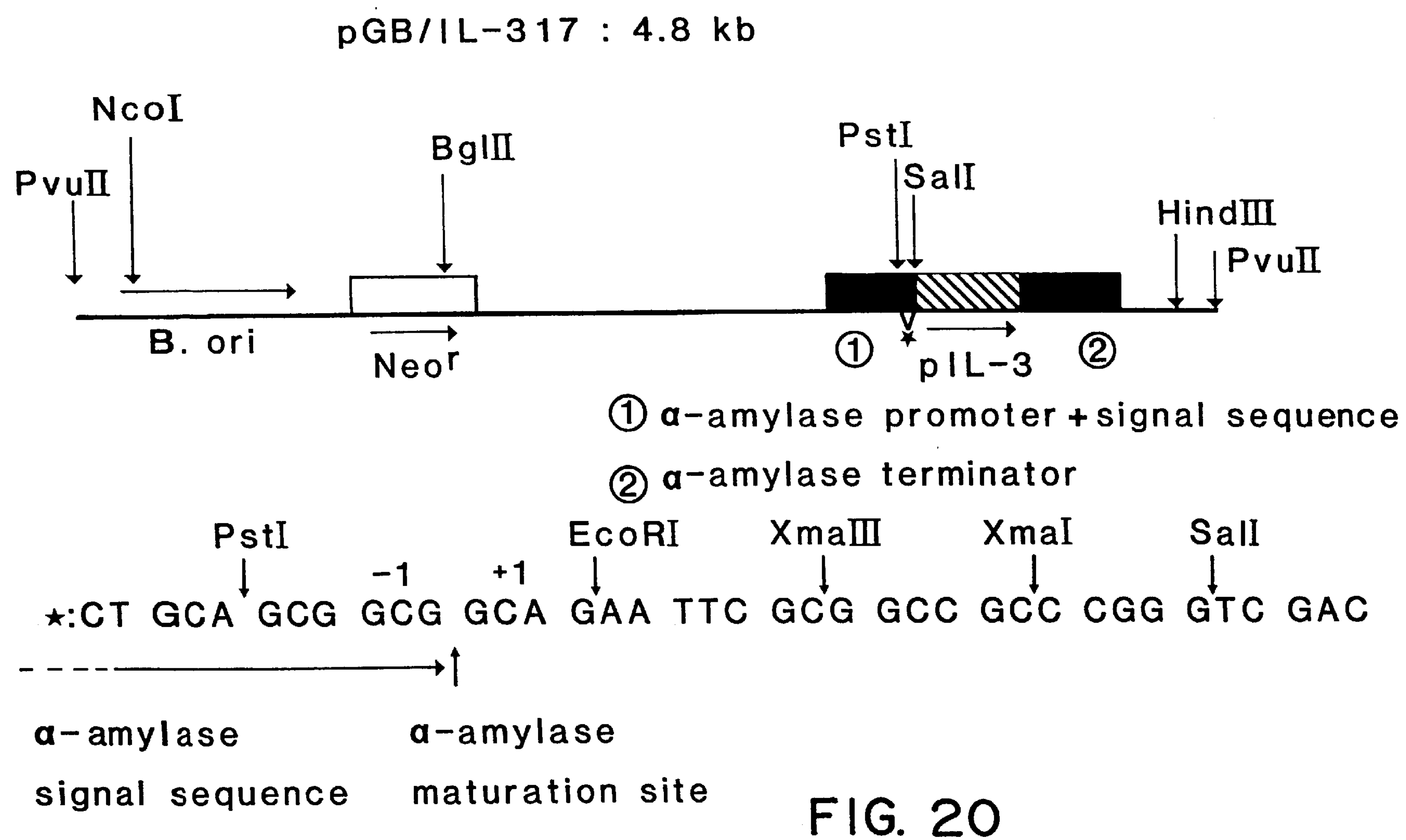
FIG. 20 (SEQ ID NO:24) shows a schematic representation of plasmid pGB/IL-317.
Figure 2I:
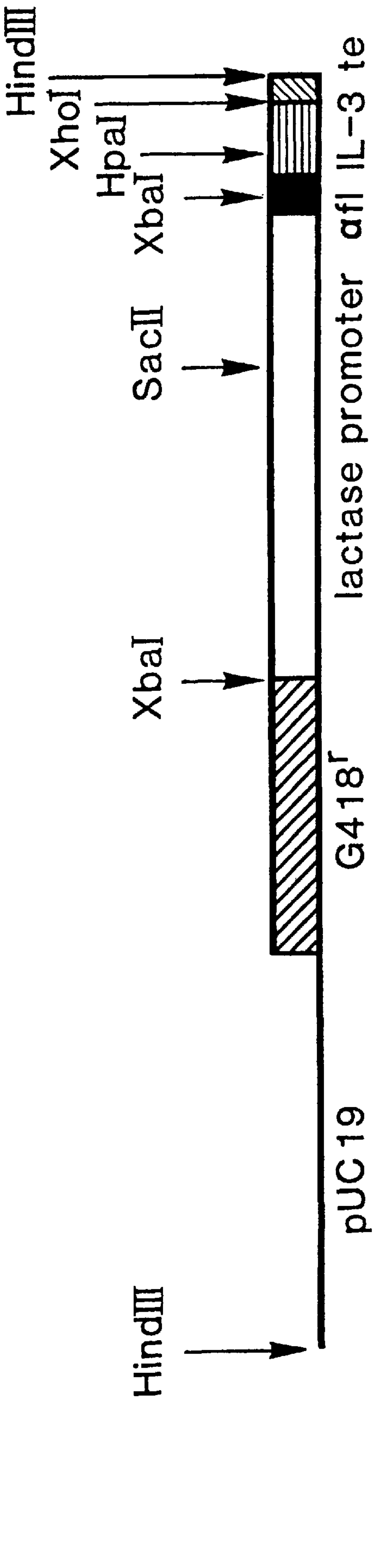

E. Construction of pGB/IL-317 (FIG. 20)

In order to clone the hmulti-CSF gene behind the *B. licheniformis* alpha-amylase transcriptional and translational initiation region and signal sequence, one of the earlier described pOL5-delta vectors (68) was used, viz. pOL5-2 delta. Besides the alpha-amylase signal sequence (29 amino acids long) this plasmid harbors one amino acid of the alpha-amylase mature sequence (an Ala) followed by a multiple cloning site: EcoRI-XmaIII-XmaI-SalI-HindIII (68).

The SalI-PvuII fragment of plasmid pGB/IL-310 containing the hmulti-CSF gene was ligated into the SalI-PvuII digested pOL5-2 delta vector and transformed to DB105. The resulting plasmid was called pGB/IL-317 (FIG. 20). The hIL-3 gene still harbors its own signal sequence on this plasmid. The plasmid was also introduced into *B. licheniformis* 7399.

F. Expression of Five Expression Plasmids in Bacillus Strains

*B. subtilis* and *B. licheniformis* strains carrying the expression plasmids mentioned below were grown in TSB medium containing 20 μg/ml neomycin or 10 μg/ml erythromycin at 37° C. (for 16–24 hours)l 300 μg/ml of the culture was centrifuged. The pellet was resuspended in sample buffer and analyzed using polyacrylamide gel-electrophoresis followed by Western blotting. The supernatant was TCA precipitated, and the pellet was resuspended in sample buffer. Both supernatant and pellet were analyzed for IL-3 protein (see Table 2).

To determine the biological activity of the produced proteins, the following steps were carried out: The cellpellets were resuspended in a buffer containing 0.1 M Tris/HCl pH 8.0 and 10 mM $MgCl_2$. Lysozyme was added to a final concentration of 1 mg/ml and PMSF to a final concentration of 1 mM. The solution was incubated for 30 min. at 37° C. Subsequently DNase (final concentration 20 μg/ml) was added and the solution was incubated for 15 min. at 20° C. Finally, the biological activity of this preparation as well as of the supernatant of the cultured cells was determined as4 described. The results are shown in Table 2.

TABLE 2

Expression of the Bacillus Vectors

| Plasmid | Strain | MW IL-3 Pellet (kd) | MW IL-3 supernatant (kd) | Biological activity pellet | Biological activity supernatant |
|---|---|---|---|---|---|
| pGB/IL-307 | DB105 | 21 | — | + | − |
| pGB/IL-310 | DB105 | 15;17 | 15;17 | − | − |
| pGB/IL-311 | DB105 | 12.5;15 | — | + | − |
| | T399 | — | — | + | − |
| pGB/IL-313 | DB105 | 15;17 | 12.5;15 | + | − |
| | T399 | — | — | + | − |
| pGB/IL-317 | DB105 | 12.5,15<br>17;20 | 12.5;15<br>17 | + | + |
| | T399 | 12.5;15<br>17;20 | 12.5;15<br>17 | + | + |

It can be concluded, that in *B. subtilis,* using pGB/IL-307, a fusion protein is made that has IL-3 activity. When the human IL-3 gene only contains its own signal sequence no significant secretion of human IL-3 is obtained. All IL-3. activity is found intracellularly. In those cases it seems that beside precursor IL-3 mature IL-3 (15 kd) has been formed in the cell. Thus, some transport across the membrane might have taken place, but the protein is not transported across the cell wall. However, using the alpha-amylase regulation and secretion signals (pGB/IL-317) most of the IL-3 activity appeared to be secreted into the culture medium. Besides a degradation product, two proteins are detected in the supernatant, one of about 15 kd and one of about 17 kd, most probably mature IL-3 and precursor IL-3, respectively. These data indicate that both processing sites, viz. the alpha-amylase and the hmulti-CSF processing site, are used. In the cell the most abundant product is precursor IL-3 containing the alpha-amylase signal sequence (the 20 kd protein) as shown by Western blotting. Sometimes a degradation product is detected.

EXAMPLE 6

Construction of *Kluyveromyces lactis* Expression Vectors

A. Construction of pGB/IL-316

A DNA fragment comprising the Tn5 gene (61) conferring resistance to gentamycin G418, under the direction of the alcohol dehydrogenase I (ADHI) promoter from *S. cerevisiae,* similar to that described by Bennetzen and Hall (62), was inserted into the SmaI site of pUC19 (63). An *E. coli* strain containing the obtained plasmid, pUC-G418, was deposited with CBS on Dec. 4, 1987 under CBS 872.87.

Into the XbaI-HindIII cleaved pUC-G418 vector a XbaI-HindIII fragment from plasmid pGB903 (64) containing the *K. lactis* lactase promoter and calf prochymosin DNA was inserted, resulting in plasmid pGB/IL-314.

The SalI-HindIII fragment from this plasmid was replaced by a synthetic DNA fragment containing a small multiple cloning site and the lactase terminator (see FIGS. 21, 22). The resulting plasmid is designated pGB/IL-315.

In the SacII-XhoI cleaved pGB/IL-315 vector the following fragments were ligated:

1. The SacII-XbaI fragment from pKS105 (U.S. pat. appln. Ser. No. 078,539, 64), carrying the 3' part of the lactase promoter and the 5' part of the alpha-factor signal sequence of *S. cerevisiae.*

2. A synthetic oligonucleotide comprising the 3' part: of the alpha-factor signal sequence starting at the XbaI site and the 5' part of the mature hIL-3 cDNA sequence upto the 5' half of the HpaI site (aa-residue 14).

3. The HpaI-XhoI fragment carrying most part of the hIL-3 cDNA sequence (residue 15–133 plus the 3' non-coding region). The resulting plasmid, designated pGB/IL-316, is depicted schematically in FIG. 21. The complete vector sequence from the SacII site in the lactase promoter sequence up to the HindIII site at the end of the synthetic terminator is given in FIG. 22.

FIG. 22 shows the nucleotide sequence of plasmid pGB/IL-316 between the unique Sac II Site in the lactase promoter and the Hind III site behind the terminator (residues 4457 to 7204). Residues 4457 to 6100 comprise the lactase promoter sequence. Residues 6101 to 6355 comprise the alpha factor signal sequence. Residues 6356 to 7115 comprise the sequence for mature human IL-3 plus the 3' noncoding cDNA sequence. Residues 7116 to 7204 comprise the synthetic terminator sequence.

B. Construction of pGB/IL-318

An expression vector similar to pGB/IL-316 was constructed in which the coding information for the alpha factor signal sequence of *S. cerevisiae* was replaced by the alpha-factor signal sequence of *K. lactis* (64). The remaining part of the plasmid is identical to pGB/IL-316. The sequence of pGB/IL-318 between the SacII site in the lactase promoter and the HindIII site behind the terminator (residues 4457 to 7190) is given in FIG. 23.

Residues 4457 to 6087 comprises the sequence of the lactase promoter and a small linker sequence. Residues 6088 to 6342 comprise the *K. lactis* alpha factor signal sequence. Residues 6343 to 7102 comprise the sequence for mature human IL-3 plus the 3' noncoding cDNA sequence. Residues 7103 to 7190 comprise the synthetic terminator sequence.

C. Transformation of *Kluyveromyces Lactis* and Analysis of Secreted hIL-3

Plasmids pGB/IL-316 and pGB/IL-318 were digested at the unique SacII site in the lactase promoter region, and used to transform *K. lactis* strain CBS 2360 (see 64). Integration of the plasmids is thus targeted to the chromosomal lactase gene promoter region. The resulting G418 resistant transformants were grown to saturation in liquid YEPD medium, and the culture supernatants and cell lysates were assayed for IL-3 activity using the AML cell DNA synthesis assay.

Virtually all IL-3 appeared to be secreted into the culture medium, and to be active. The proteins from the culture supernatant were precipitated using ethanol and analyzed using denaturing polyacrylamide gel-electrophoresis followed by Western blotting. The predominant product has an apparent MW of about 21 kd, whereas also a distinct band at about 15 kd is observed. The latter product most probably corresponds to the mature unglycosylated IL-3, whereas the 21 kd product is the product carrying core glycosylation at the two potential glycosylation sites. Incubation with Endoglycosidase H results in a protein migrating in the 15 kd range, suggesting that all IL-3 is processed correctly during the secretion process and that the bulk of the protein is being glycosylated.

EXAMPLE 7

Construction of a *Saccharomyces Cerevisiae* Expression Vector

A. Construction of pGB/IL-319

First an expression vector called pGB/TEFact was constructed. On this pTZ18R (Pharmacia) derived plasmid the *S. cerevisiae* translation elongation factor (EP-1alpha) promoter sequence, which was cloned and sequenced as described (73,74), is coupled by means of a small SalI-BglII-XhoI linker to the *S. cerevisiae* actin transcription terminator sequence (75), which was synthesized using an Applied Biosystems DNA synthesizer. The sequence of the expression cassette is given in FIG. 24. Residues 1 to 949 comprise the EF-1alpha promoter. Residues 950 to 967 comprise the sequence of the SalI-BglII-XhoI linker. Residues 968 to 1113 comprise the actin terminator sequence.

The unique SmaI site in pGB/TEFact was used to introduce the G418 resistance cassette described in Example 6. The resulting plasmid was called pGB/TEFactG418.

Finally, the hIL-3 expression vector pGB/IL-318 was constructed by introduction of the following DNA sequences into the SalI-XhoI cleaved pGB/TEFactG418 plasmid:

- The SalI-NruI fragment from pGB/IL-316 carrying the *S. cerevisiae* alpha factor signal sequence and the hIL-3 coding sequence upto the NruI site.
- A synthetic NruI-XhoI DNA fragment comprising the remaining nucleotides coding for hIL-3 and the XhoI recognition sequence immediately following the TGA stopcodon.

B. Transformation of *Saccharomyces Cerevisiae* and Analysis of Secreted hIL-3

Plasmid pGB/IL-319 was-cleaved at the unique EcoRI site in the EF-1α promoter. Integration of the plasmid is thus targeted to the chromosomal EF-1α region. *S. cerevisiae* wild type strain D273-103 (alpha; ATCC 25657) was transformed as described for *K. lactis* (64). The G418-resistant colonies were picked and transformants were given to saturation in liquid YEPD medium. The culture supernatant was assayed for hIL-3 activity using the AML assay. The protein produced by *S. cerevisiae* was found biologically active.

The proteins from the supernatant were precipitated using ethanol and subsequently analyzed by polyacrulamide gel-electrophoresis followed by Western blotting. Two prominent products could be distinguished on the Western blot, a 21 kd glycosylated product and an unglycolysed product of about 15 kd.

REFERENCES

1 Metcalf D., Blood 67, 257–267 (1986).
2 Whetton A. D. and Dexter T. M. TIBS 11, 207–211 (1986).
3 Wagemaker G., In “Bone Marrow Transplantation” (eds. Van Bekkum D. W. and Lowenberg B.) Marcel Dekker Inc. New York 1–72 (1985).
4 Dorssers L. et. al., Exp. Hematol. 12, 357, 1984.
5 Till J. E. and McCulloch E. A., Radiat. Res. 14, 213–222 (1961).
6 Hapel A. J., et. al., Blood 65, 1453–1459 (1985).
7 Scheven B. A. A., Nature 321, 79–81 (1986).
8 Garland J. M. and Crompton S. Exp. Hematol. 11, 757–761 (1983).
9 Stanley E. R. et. al., Cell 45, 667–674 (1986).
10 Kreigler A. B. et. al., Blood 60, 503–508 (1982).
11 Fung M. C. et. al., Nature 307, 233–237 (1984).
12 Yokata T. et. al., Proc. Natl. Acad. Sci. USA, 81, 1070–1074 (1984).
13 Lowenberg B. and Dicke K. A., Exp. Hematol. 5, 319–331 (1977).
14 Wagemaker G. and Peters M. F., Cell. Tiss. Kinet. 11, 45–56 (1978).
15 Ihle J. N., et. al., In “advances in viral oncology”, vol. 4 (ed Klein G.) 95–137, Raven Press, New York 1984.
16 Fauser A. A. and Messner H. A. Blood 52, 1243–1248 (1978).
17 Lowenberg B. et. al., Leuk. Res. 4, 143–149 (1980).
18 Lowenberg B. et. al., Blood 59, 64–645 (1982).
19 Buick R. N. et. al., Blood 54, 95–104 (1979).
20 Huynh T. V. et. al., In “DNA cloning”, vol. 1 (Ed. Glover D. M.) IRL press, Oxford 45–78 (1985).
21 Kozak M. Cell 44, 283–292 (1983).
22 Von Heijne G. Eur J. Biochem 133, 17–21 (1983).
23 Perlman D. and Halvorson H. O., J. Mol. Biol. 167, 391–409 (1983).
24 Shaw G. and Kamen R. Cell 46, 659–667 (1986).
25 Schrader J. W., et. al., Proc. Natl. Acad. Sci. USA 83, 2458–2462 (1986).
26 March C. J., et. al., Nature 315, 641–647 (1985).
27 Higashi Y. et. al., J. Biol. Chem. 258, 9522–9529 (1983).
28 Dijkema R. et. al., EMBO J. 4, 761–767 (1985).
29 Zwarthoff E. C. et. al., Nucleic Acid Res. 13, 791–804 (1985).
30 Clark-Lewis I. et. al., Science 231, 134–139 (1986).
31 Kindler V. et. al., Proc. Natl. Acad. Sci. USA 83, 1001–1005 (1986).
32 DeLamarter J. F. et. al., EMBO J. 10, 2575–2581 (1985).
33 Lemischka I. R. et. al., Cell 45, 917–927 (1986).

34 Yu-Chung Yang et. al., Cell 47, 3–10 (1986.).
35 Miyatake S. et. al., Proc. Natl. Acad. Sci. USA 82, 316–320 (1985).
36 Maniatis T. et. al., In "Molecular Cloning, A. laboratory manual". Cold Spring Harbor Laboratories, New York (1982).
37 Gubler D. and Hofmann B. J., Gene 25, 263–269 (1983).
38 Feinberg A. P. and Vogelstein B. Anal. Biochem. 132, 6–13 (1983).
39 Sanger F. et. al., Proc. Natl. Acad. Sci. USA 74, 5463 (1977).
40 Queen C. and Korn L. J. Nucleic Acid Res. 12, 581–599 ( 1984).
41 Staden R. Nucleic Acid Res. 10, 2951–2961 (1982).
42 Devereux J., et. al., Nucleic Acid Res. 12, 387–395 (1984).
43 Lipman D. J. and Pearson W. R. Science 227, 1435–1441 (1985).
44 Subramani S. and Southern P. J., Anal. Bioch. 135, 1–15 (1983).
45 Wigler M., et. al., Cell 14, 725–731 (1978).
46 Majdic O., et. al., Int. J. Cancer 33, 617–623 (1984).
47 Lowenberg B. and Bauman J. G. J. Blood 66, 1225–1232 (1984).
48 Delwel R., et. al., Blood 68, 41–45 (1986)
49 Swart K. et. al., Blood 59, 816–821 (1982).
50 Swart K. and Lowenberg B. Cancer Res. 44, 657–660 (1984).
51 Touw I. et. al., Blood 68, 1088–1094 (1986).
52 Vieira, J. and Messing J., Gene 19, 259–268 (1982)
53 Osinga, K. A. et al., Nucleic Acids Res. 11, 8595–8608 (1983)
54. Gryczan, T. C. et al., J. Bacteriology 134, 318–329 (1978)
55. Kawamura, F. and Doi, R. H., J. Bacteriology 160, 442–444 (1984)
56. Bron, S. and Venema, G., Mutat. Res. 15, 1–10 (1972).
57. Zyprian, E. and Matzura, H., DNA 5, 219–225 (1986).
58. EPA 0224294, published Jun. 3, 1987.
59. EPA 0244042, published Nov. 4, 1987.
60. Stanssens P. et al., In "Protein Engineering and Site-Directed Mutagenesis". Twenty-Fourth Harden Conference. Program and Abstracts (1985) (Fersht, A. R. and Winter, G., edts).
61. Reiss, B. et al., EMBO J. 3, 3317–3322 (1984).
62. Bennetzen, J. L. and Hall, B. D., J. Biol. Chem. 257, 3018–3025 (1982).
63. Yanisch-Perron, C. et al., Gene 33, 103–119 (1985).
64. U.S. appl. Ser. No. 078,539, filed Jul. 28, 1987.
65. Salfre, S. and Milstein, C., Meth Enz 73, 3–75 (1981).
66. McKenzie, T. et al., Plasmid 15, 93–103 (1986).
67. McKenzie, T. et al., Plasmid 17, 83–85 (1987).
68. European Patent Application 87201379.2, filed Jul. 20, 1987.
69. Chen, E. Y. et al., Nature 299, 529–534 (1982).
70. Law, M-F. et al., Mol. Cell Biol. 3, 2110–2115 (1983)
71. Hirt, B., J. Mol. Biol. 26, 365–367 (1967).
72. Suarez Rendueles, M. P. et al., FEBS Lett. 131, 296–300 (1981).
73. Najata, S. et al., EMBO J. 3, 1825–1830 (1984).
74. Nagashima, K. et al., Gene 45, 265–273 (1986).
75. Gallwitz, D. and Sures, I., Proc. Natl. Acad. Sci. USA 77, 2546–2550 (1980).

We claim:

1. Purified human interleukin-3 having the amino acid sequence numbered +1 to +133 of SEQ ID NO:2.

2. The interleukin-3 of claim 1 in glycosylated form.

3. The interleukin-3 of claim 1 in unglycosylated form.

4. Purified interleukin-3 produced by purifying the protein encoded by the DNA sequence of nucleotides 96–494 of SEQ ID NO:1 wherein said protein is recombinantly expressed in a transformed host cell containing said DNA sequence.

5. The interleukin-3 of claim 4 in glycosylated form.

6. The interleukin-3 of claim 4 in unglycosylated form.

7. The interleukin-3 of claim 4 wherein said host cell is selected from the group consisting of Saccharomyces, Kluyveromyces, *E. coli,* Bacillus, COS, C127 and insect cells.

8. A method to produce an antibody or cells capable of producing an antibody, which method comprises obtaining an antibody or cells capable of producing an antibody from a vertebrate host injected with the purified human IL-3 of any one of claims 22 to 28, wherein said antibody is capable of immunospecific reaction with human IL-3.

9. A recombinant cDNA molecule which encodes human IL-3 having a proline at position 8, wherein said human IL-3 has the amino acid sequence of amino acids +1 to +133 of SEQ ID NO:2.

10. A recombinant cDNA molecule according to claim 9 which comprises the nucleotide sequence of nucleotides 96–494 of SEQ ID NO:1.

11. An expression cassette capable of expressing a nucleotide sequence encoding human IL-3 which IL-3 has the amino acid sequence of amino acids +1 to +133 of SEQ ID NO:2, said sequence having a proline at position 8, in a recombinant host cell, which expression cassette comprises a DNA molecule containing a nucleotide sequence encoding said human IL-3 operably linked to control sequences effective for expression in said host cell.

12. An expression cassette according to claim 11, wherein said encoding DNA is cDNA having the nucleotide sequence of nucleotides 96–494 of SEQ ID NO:1.

13. An expression cassette according to claim 11 or 12, wherein the control sequences comprise a promoter selected from the group consisting of the lac promoter, the HpaII promoter, the $\sigma^{73}$ promoter, the alpha-amylase promoter, the EF-1 alpha promoter and the SV40 promoter.

14. A method for producing human IL-3 having the amino acid sequence of amino acids +1 to +133 of SEQ ID NO:2, thus having a proline at position 8, comprising culturing a host cell modified to contain the expression cassette of claim 11 under conditions wherein said nucleotide sequence encoding said IL-3 is expressed and said human IL-3 is produced.

15. A method according to claim 14, wherein said host cell is selected from the group consisting of a yeast cell, a bacterial cell, a fungal cell and a cultured animal cell.

16. The method of claim 15 or 14 wherein the DNA encoding human IL-3 has the nucleotide sequence of nucleotides 96–494 of SEQ ID NO:1.

17. A method according to claim 15, wherein said host cell is a yeast cell selected from the group consisting of a Saccharomyces cell and a Kluyveromyces cell.

18. A method according to claim 15, wherein said host cell is a bacterial cell selected from the group consisting of an *E. coli* cell and a Bacillus cell.

19. A method according to claim 15, wherein said host cell is a cultured animal cell selected from the group consisting of a COS cell, a C127 cell and an insect cell.

20. A transformed living host cell comprising recombinant DNA encoding human IL-3 having a proline at position 8 of the mature IL-3 protein molecule wherein said mature IL-3 protein molecule has the amino acid sequence of amino acids +1 to +133 of SEQ ID NO:2.

21. A transformed living host cell according to claim 20, which is selected from the group consisting of a yeast cell, a bacterial cell, a fungal cell and a cultured animal cell.

22. A transformed living host cell according to claim 21, which is a yeast cell selected from the group consisting of a Saccharomyces cell and a Kluyveromyces cell.

23. A transformed host cell according to claim 21, which is a bacterial cell selected from the group consisting of an *E. coli* cell and a Bacillus cell.

24. A transformed host cell according to claim 21, which is a cultured animal cell selected from the group consisting of a COS cell, a C127 cell and an insect cell.

25. The transformed living host cell of any one of claims 20–24 wherein said DNA encoding human IL-3 has the nucleotide sequence of nucleotides 96–494 of SEQ ID NO:1.

26. A derivative of human interleukin-3, said derivative having an amino acid sequence corresponding to the amino acid sequence of the protein expressed by a plasmid selected from the group consisting of pGB/IL-301, pGB/IL-302, pGB/IL-303, pGB/IL-304, pGB/IL-305 and pGB/IL-306.

27. The derivative of claim 26 in glycosylated form.

28. The derivative of claim 26 in unglycosylated form.

29. The derivative of claim 26, having an amino acid sequence of the protein expressed by the plasmid pGB/IL-301.

30. The derivative of claim 26, having an amino acid sequence of the protein expressed by the plasmid pGB/IL-302.

31. The derivative of claim 26, having an amino acid sequence of the protein expressed by the plasmid pGB/IL-303.

32. The derivative of claim 26, having an amino acid sequence of the protein expressed by the plasmid pGB/IL-304.

33. The derivative of claim 26, having an amino acid sequence of the protein expressed by the plasmid pGB/IL-305.

34. The derivative of claim 26, having an amino acid sequence of the protein expressed by the plasmid pGB/IL-306.

* * * * *

SEQUENCE LISTING

```
(1) GENERAL INFORMATION:

   (iii) NUMBER OF SEQUENCES: 27


(2) INFORMATION FOR SEQ ID NO: 1:

     (i) SEQUENCE CHARACTERISTICS:
          (A) LENGTH: 910 base pairs
          (B) TYPE: nucleic acid
          (C) STRANDEDNESS: double
          (D) TOPOLOGY: linear

    (ii) MOLECULE TYPE: cDNA to mRNA

   (iii) HYPOTHETICAL: NO

   (iii) ANTI-SENSE: NO

    (vi) ORIGINAL SOURCE:
          (A) ORGANISM: Homo sapiens

   (vii) IMMEDIATE SOURCE:
          (B) CLONE: D11

    (ix) FEATURE:
          (A) NAME/KEY: CDS
          (B) LOCATION: 39..497

    (ix) FEATURE:
          (A) NAME/KEY: sig_peptide
          (B) LOCATION: 39..95

    (ix) FEATURE:
          (A) NAME/KEY: mat_peptide
```

-continued

```
          (B) LOCATION: 96..497

    (xi) SEQUENCE DESCRIPTION: SEQ ID NO: 1:

GACCAGAACA AGACAGAGTG CCTCCTGCCG ATCCAAAC ATG AGC CGC CTG CCC         53
                                          Met Ser Arg Leu Pro
                                          -19             -15

GTC CTG CTC CTG CTC CAA CTC CTG GTC CGC CCC GGA CTC CAA GCT CCC      101
Val Leu Leu Leu Leu Gln Leu Leu Val Arg Pro Gly Leu Gln Ala Pro
                -10                 -5                   1

ATG ACC CAG ACA ACG CCC TTG AAG ACA AGC TGG GTT AAC TGC TCT AAC      149
Met Thr Gln Thr Thr Pro Leu Lys Thr Ser Trp Val Asn Cys Ser Asn
          5                  10                  15

ATG ATC GAT GAA ATT ATA ACA CAC TTA AAG CAG CCA CCT TTG CCT TTG      197
Met Ile Asp Glu Ile Ile Thr His Leu Lys Gln Pro Pro Leu Pro Leu
     20                  25                  30

CTG GAC TTC AAC AAC CTC AAT GGG GAA GAC CAA GAC ATT CTG ATG GAA      245
Leu Asp Phe Asn Asn Leu Asn Gly Glu Asp Gln Asp Ile Leu Met Glu
 35                  40                  45                  50

AAT AAC CTT CGA AGG CCA AAC CTG GAG GCA TTC AAC AGG GCT GTC AAG      293
Asn Asn Leu Arg Arg Pro Asn Leu Glu Ala Phe Asn Arg Ala Val Lys
                 55                  60                  65

AGT TTA CAG AAC GCA TCA GCA ATT GAG AGC ATT CTT AAA AAT CTC CTG      341
Ser Leu Gln Asn Ala Ser Ala Ile Glu Ser Ile Leu Lys Asn Leu Leu
             70                  75                  80

CCA TGT CTG CCC CTG GCC ACG GCC GCA CCC ACG CGA CAT CCA ATC CAT      389
Pro Cys Leu Pro Leu Ala Thr Ala Ala Pro Thr Arg His Pro Ile His
         85                  90                  95

ATC AAG GAC GGT GAC TGG AAT GAA TTC CGG AGG AAA CTG ACG TTC TAT      437
Ile Lys Asp Gly Asp Trp Asn Glu Phe Arg Arg Lys Leu Thr Phe Tyr
    100                 105                 110

CTG AAA ACC CTT GAG AAT GCG CAG GCT CAA CAG ACG ACT TTG AGC CTC      485
Leu Lys Thr Leu Glu Asn Ala Gln Ala Gln Gln Thr Thr Leu Ser Leu
115                 120                 125                 130

GCG ATC TTT TGAGTCCAAC GTCCAGCTCG TTCTCTGGGC CTTCTCACCA              534
Ala Ile Phe

CAGAGCCTCG GGACATCAAA AACAGCAGAA CTTCTGAAAC CTCTGGGTCA TCTCTCACAC    594

ATTCCAGGAC CAGAAGCATT TCACCTTTTC CTGCGGCATC AGATGAATTG TTAATTATCT    654

AATTTCTGAA ATGTGCAGCT CCCATTTGGC CTTGTGCGGT TGTGTTCTCA TTTTTATCCC    714

ATTGAGACTA TTTATTTATG TATGTATGTA TTTATTTATT TATTGCCTGG AGTGTGAACT    774

GTATTTATTT TAGCAGAGGA GCCATGTCCT GCTGCTTCTG CAAAAAACTC AGAGTGGGGT    834

GGGGAGCATG TTCATTTGTA CCTCGAGTTT TAAACTGGTT CCTAGGGATG TGTGAGAATA    894

AACTAGACTC TGAACA                                                    910


(2) INFORMATION FOR SEQ ID NO: 2:

     (i) SEQUENCE CHARACTERISTICS:
          (A) LENGTH: 152 amino acids
          (B) TYPE: amino acid
          (D) TOPOLOGY: linear

    (ii) MOLECULE TYPE: protein

    (xi) SEQUENCE DESCRIPTION: SEQ ID NO: 2:

Met Ser Arg Leu Pro Val Leu Leu Leu Leu Gln Leu Leu Val Arg Pro
-19             -15                 -10                  -5

Gly Leu Gln Ala Pro Met Thr Gln Thr Thr Pro Leu Lys Thr Ser Trp
              1               5                  10
```

-continued

```
Val Asn Cys Ser Asn Met Ile Asp Glu Ile Ile Thr His Leu Lys Gln
     15                  20                  25

Pro Pro Leu Pro Leu Leu Asp Phe Asn Asn Leu Asn Gly Glu Asp Gln
 30                  35                  40                  45

Asp Ile Leu Met Glu Asn Asn Leu Arg Arg Pro Asn Leu Glu Ala Phe
                 50                  55                  60

Asn Arg Ala Val Lys Ser Leu Gln Asn Ala Ser Ala Ile Glu Ser Ile
             65                  70                  75

Leu Lys Asn Leu Leu Pro Cys Leu Pro Leu Ala Thr Ala Ala Pro Thr
         80                  85                  90

Arg His Pro Ile His Ile Lys Asp Gly Asp Trp Asn Glu Phe Arg Arg
     95                 100                 105

Lys Leu Thr Phe Tyr Leu Lys Thr Leu Glu Asn Ala Gln Ala Gln Gln
110                 115                 120                 125

Thr Thr Leu Ser Leu Ala Ile Phe
                130
```

(2) INFORMATION FOR SEQ ID NO: 3:

(i) SEQUENCE CHARACTERISTICS:
(A) LENGTH: 851 base pairs
(B) TYPE: nucleic acid
(C) STRANDEDNESS: double
(D) TOPOLOGY: linear (ii) MOLECULE TYPE: cDNA to mRNA (iii) HYPOTHETICAL: NO (iii) ANTI-SENSE: NO (vi) ORIGINAL SOURCE:
(A) ORGANISM: Mus musculus (ix) FEATURE:
(A) NAME/KEY: CDS
(B) LOCATION: 29..529

(ix) FEATURE:
(A) NAME/KEY: sig_peptide
(B) LOCATION: 29..106

(ix) FEATURE:
(A) NAME/KEY: mat_peptide
(B) LOCATION: 107..529
(D) OTHER INFORMATION: /product= "Interleukin-3"
/citation= ([1])

(x) PUBLICATION INFORMATION:
(A) AUTHORS: Miyatake, S.
Yokota, T.
Lee, F.
Arai, K.-I.
(B) TITLE: Structure of the chromosomal gene for murine interleukin-3
(C) JOURNAL: Proc. Natl. Acad. Sci. U.S.A.
(D) VOLUME: 82
(F) PAGES: 316-320
(G) DATE: 1985

(xi) SEQUENCE DESCRIPTION: SEQ ID NO: 3:

```
GAACCCCTTG GAGGACCAGA ACGAGACA ATG GTT CTT GCC AGC TCT ACC ACC        52
                               Met Val Leu Ala Ser Ser Thr Thr
                               -26 -25                 -20

AGC ATC CAC ACC ATG CTG CTC CTG CTC CTG ATG CTC TTC CAC CTG GGA      100
Ser Ile His Thr Met Leu Leu Leu Leu Leu Met Leu Phe His Leu Gly
            -15                 -10                  -5

CTC CAA GCT TCA ATC AGT GGC CGG GAT ACC CAC CGT TTA ACC AGA ACG      148
```

-continued

```
Leu Gln Ala Ser Ile Ser Gly Arg Asp Thr His Arg Leu Thr Arg Thr
          1               5                  10

TTG AAT TGC AGC TCT ATT GTC AAG GAG ATT ATA GGG AAG CTC CCA GAA      196
Leu Asn Cys Ser Ser Ile Val Lys Glu Ile Ile Gly Lys Leu Pro Glu
 15                  20                  25                  30

CCT GAA CTC AAA ACT GAT GAT GAA GGA CCC TCT CTG AGG AAT AAG AGC      244
Pro Glu Leu Lys Thr Asp Asp Glu Gly Pro Ser Leu Arg Asn Lys Ser
                 35                  40                  45

TTT CGG AGA GTA AAC CTG TCC AAA TTC GTG GAA AGC CAA GGA GAA GTG      292
Phe Arg Arg Val Asn Leu Ser Lys Phe Val Glu Ser Gln Gly Glu Val
             50                  55                  60

GAT CCT GAG GAC AGA TAC GTT ATC AAG TCC AAT CTT CAG AAA CTT AAC      340
Asp Pro Glu Asp Arg Tyr Val Ile Lys Ser Asn Leu Gln Lys Leu Asn
         65                  70                  75

TGT TGC CTG CCT ACA TCT GCG AAT GAC TCT GCG CTG CCA GGG GTC TTC      388
Cys Cys Leu Pro Thr Ser Ala Asn Asp Ser Ala Leu Pro Gly Val Phe
     80                  85                  90

ATT CGA GAT CTG GAT GAC TTT CGG AAG AAA CTG AGA TTC TAC ATG GTC      436
Ile Arg Asp Leu Asp Asp Phe Arg Lys Lys Leu Arg Phe Tyr Met Val
 95                 100                 105                 110

CAC CTT AAC GAT CTG GAG ACA GTG CTA ACC TCT AGA CCA CCT CAG CCC      484
His Leu Asn Asp Leu Glu Thr Val Leu Thr Ser Arg Pro Pro Gln Pro
                115                 120                 125

GCA TCT GGC TCC GTC TCT CCT AAC CGT GGA ACC GTG GAA TGT TAAAACAGCA   536
Ala Ser Gly Ser Val Ser Pro Asn Arg Gly Thr Val Glu Cys
            130                 135                 140

GGCAGAGCAC CTAAAGTCTG AATGTTCCTC ATGGCCCATG GTCAAAAGGA TTTTACATTC    596

CTTTATGCCA TCAAATGTCT TATCAATTTA TCTACTTTCT GAAATTTACA ACTCTCCTTT    656

GGCTTTACCT AATTATGTTC CTATTTTATT CCATTAAGGC TATTTATTTA TGTATTTATG    716

TATTTATTTA TTTATTGCCT TCTGTGATGT GAGTATATCT GTTTTAGCTG AGGAGGAGTT    776

TCTCCAAAGA AAATTCCAAG GAAGACTGGG GCCATGTTCA TTTGTCCCTT GTGGAAATAA    836

ATAACTTTGA ACAAA                                                     851
```

(2) INFORMATION FOR SEQ ID NO: 4:

(i) SEQUENCE CHARACTERISTICS:
(A) LENGTH: 166 amino acids
(B) TYPE: amino acid
(D) TOPOLOGY: linear (ii) MOLECULE TYPE: protein (xi) SEQUENCE DESCRIPTION: SEQ ID NO: 4:

```
Met Val Leu Ala Ser Ser Thr Thr Ser Ile His Thr Met Leu Leu Leu
-26 -25                 -20                 -15

Leu Leu Met Leu Phe His Leu Gly Leu Gln Ala Ser Ile Ser Gly Arg
-10                  -5                   1               5

Asp Thr His Arg Leu Thr Arg Thr Leu Asn Cys Ser Ser Ile Val Lys
             10                  15                  20

Glu Ile Ile Gly Lys Leu Pro Glu Pro Glu Leu Lys Thr Asp Asp Glu
         25                  30                  35

Gly Pro Ser Leu Arg Asn Lys Ser Phe Arg Arg Val Asn Leu Ser Lys
     40                  45                  50

Phe Val Glu Ser Gln Gly Glu Val Asp Pro Glu Asp Arg Tyr Val Ile
 55                  60                  65                  70

Lys Ser Asn Leu Gln Lys Leu Asn Cys Cys Leu Pro Thr Ser Ala Asn
                 75                  80                  85
```

-continued

Asp Ser Ala Leu Pro Gly Val Phe Ile Arg Asp Leu Asp Asp Phe Arg
            90                  95                  100

Lys Lys Leu Arg Phe Tyr Met Val His Leu Asn Asp Leu Glu Thr Val
        105                 110                 115

Leu Thr Ser Arg Pro Pro Gln Pro Ala Ser Gly Ser Val Ser Pro Asn
    120                 125                 130

Arg Gly Thr Val Glu Cys
135                 140

(2) INFORMATION FOR SEQ ID NO: 5:

(i) SEQUENCE CHARACTERISTICS:
(A) LENGTH: 60 base pairs
(B) TYPE: nucleic acid
(C) STRANDEDNESS: double
(D) TOPOLOGY: linear (ii) MOLECULE TYPE: DNA (synthetic)

(iii) HYPOTHETICAL: NO (iii) ANTI-SENSE: NO (vii) IMMEDIATE SOURCE:
(B) CLONE: pTZ18R (xi) SEQUENCE DESCRIPTION: SEQ ID NO: 5:

GGGAATTCGA GCTCGGTACC CGGGGATCCT CTAGAGTCGA CCTGCAGGCA TGCAAGCTTG 60

(2) INFORMATION FOR SEQ ID NO: 6:

(i) SEQUENCE CHARACTERISTICS:
(A) LENGTH: 87 base pairs
(B) TYPE: nucleic acid
(C) STRANDEDNESS: double
(D) TOPOLOGY: linear (ii) MOLECULE TYPE: DNA (synthetic)

(iii) HYPOTHETICAL: NO (iii) ANTI-SENSE: NO (vii) IMMEDIATE SOURCE:
(B) CLONE: pT1

(xi) SEQUENCE DESCRIPTION: SEQ ID NO: 6:

GGGAATCCGA GCTCGATATC AAGCTTAGAT CTCGAGGGGG ATCCTCTAGA GTCGACCTGC 60

AGGCATGCAA GCTGCATATG CAGCTTG 87

(2) INFORMATION FOR SEQ ID NO: 7:

(i) SEQUENCE CHARACTERISTICS:
(A) LENGTH: 189 base pairs
(B) TYPE: nucleic acid
(C) STRANDEDNESS: double
(D) TOPOLOGY: linear (ii) MOLECULE TYPE: cDNA to mRNA (iii) HYPOTHETICAL: NO (iii) ANTI-SENSE: NO (vii) IMMEDIATE SOURCE:
(B) CLONE: pGB/IL-301

(ix) FEATURE:
(A) NAME/KEY: CDS

-continued

```
        (B) LOCATION: 1..189

    (xi) SEQUENCE DESCRIPTION: SEQ ID NO: 7:

ATG ACC ATG ATT ACG AAT TCC CGG GGA TCT GGA CCA GAA CAA GAC AGA        48
Met Thr Met Ile Thr Asn Ser Arg Gly Ser Gly Pro Glu Gln Asp Arg
  1               5                  10                  15

GTG CCT CCT GCC GAT CCA AAC ATG AGC CGC CTG CCC GTC CTG CTC CTG        96
Val Pro Pro Ala Asp Pro Asn Met Ser Arg Leu Pro Val Leu Leu Leu
             20                  25                  30

CTC CAA CTC CTG GTC CGC CCC GGA CTC CAA GCT CCC ATG ACC CAG ACA       144
Leu Gln Leu Leu Val Arg Pro Gly Leu Gln Ala Pro Met Thr Gln Thr
         35                  40                  45

ACG CCC TTG AAG ACA AGC TGG GTT AAC TGC TCT AAC ATG ATC GAT           189
Thr Pro Leu Lys Thr Ser Trp Val Asn Cys Ser Asn Met Ile Asp
     50                  55                  60


(2) INFORMATION FOR SEQ ID NO: 8:

     (i) SEQUENCE CHARACTERISTICS:
          (A) LENGTH: 63 amino acids
          (B) TYPE: amino acid
          (D) TOPOLOGY: linear

    (ii) MOLECULE TYPE: protein

    (xi) SEQUENCE DESCRIPTION: SEQ ID NO: 8:

Met Thr Met Ile Thr Asn Ser Arg Gly Ser Gly Pro Glu Gln Asp Arg
  1               5                  10                  15

Val Pro Pro Ala Asp Pro Asn Met Ser Arg Leu Pro Val Leu Leu Leu
             20                  25                  30

Leu Gln Leu Leu Val Arg Pro Gly Leu Gln Ala Pro Met Thr Gln Thr
         35                  40                  45

Thr Pro Leu Lys Thr Ser Trp Val Asn Cys Ser Asn Met Ile Asp
     50                  55                  60


(2) INFORMATION FOR SEQ ID NO: 9:

     (i) SEQUENCE CHARACTERISTICS:
          (A) LENGTH: 102 base pairs
          (B) TYPE: nucleic acid
          (C) STRANDEDNESS: double
          (D) TOPOLOGY: linear

    (ii) MOLECULE TYPE: cDNA to mRNA

   (iii) HYPOTHETICAL: NO

   (iii) ANTI-SENSE: NO

   (vii) IMMEDIATE SOURCE:
          (B) CLONE: pGB/IL-302

    (ix) FEATURE:
          (A) NAME/KEY: CDS
          (B) LOCATION: 1..102

    (xi) SEQUENCE DESCRIPTION: SEQ ID NO: 9:

ATG ACC ATG ATT ACG AAT TCC CGG GGA TCC TCT AGA GTC GAC CCC ATG        48
Met Thr Met Ile Thr Asn Ser Arg Gly Ser Ser Arg Val Asp Pro Met
  1               5                  10                  15

ACC CAG ACA ACG CCC TTG AAG ACA AGC CGG GTT AAC TGC TCT AAC ATG        96
Thr Gln Thr Thr Pro Leu Lys Thr Ser Arg Val Asn Cys Ser Asn Met
             20                  25                  30

ATC GAT                                                               102
Ile Asp
```

-continued

```
(2) INFORMATION FOR SEQ ID NO: 10:

     (i) SEQUENCE CHARACTERISTICS:
          (A) LENGTH: 34 amino acids
          (B) TYPE: amino acid
          (D) TOPOLOGY: linear

    (ii) MOLECULE TYPE: protein

    (xi) SEQUENCE DESCRIPTION: SEQ ID NO: 10:

Met Thr Met Ile Thr Asn Ser Arg Gly Ser Ser Arg Val Asp Pro Met
  1               5                  10                  15

Thr Gln Thr Thr Pro Leu Lys Thr Ser Arg Val Asn Cys Ser Asn Met
             20                  25                  30

Ile Asp


(2) INFORMATION FOR SEQ ID NO: 11:

     (i) SEQUENCE CHARACTERISTICS:
          (A) LENGTH: 102 base pairs
          (B) TYPE: nucleic acid
          (C) STRANDEDNESS: double
          (D) TOPOLOGY: linear

    (ii) MOLECULE TYPE: cDNA to mRNA

   (iii) HYPOTHETICAL: NO

   (iii) ANTI-SENSE: NO

   (vii) IMMEDIATE SOURCE:
          (B) CLONE: pGB/IL-303

    (ix) FEATURE:
          (A) NAME/KEY: CDS
          (B) LOCATION: 1..102

    (xi) SEQUENCE DESCRIPTION: SEQ ID NO: 11:

ATG ACC ATG ATT ACG AAT TCC CGG GGA TCC TCT AGA GTC GAC CCC ATG        48
Met Thr Met Ile Thr Asn Ser Arg Gly Ser Ser Arg Val Asp Pro Met
  1               5                  10                  15

ACC CAG ACA ACG CCC CCG AAG ACA AGC CGG GTT AAC TGC TCT AAC ATG        96
Thr Gln Thr Thr Pro Pro Lys Thr Ser Arg Val Asn Cys Ser Asn Met
             20                  25                  30

ATC GAT                                                               102
Ile Asp


(2) INFORMATION FOR SEQ ID NO: 12:

     (i) SEQUENCE CHARACTERISTICS:
          (A) LENGTH: 34 amino acids
          (B) TYPE: amino acid
          (D) TOPOLOGY: linear

    (ii) MOLECULE TYPE: protein

    (xi) SEQUENCE DESCRIPTION: SEQ ID NO: 12:

Met Thr Met Ile Thr Asn Ser Arg Gly Ser Ser Arg Val Asp Pro Met
  1               5                  10                  15

Thr Gln Thr Thr Pro Pro Lys Thr Ser Arg Val Asn Cys Ser Asn Met
             20                  25                  30

Ile Asp


(2) INFORMATION FOR SEQ ID NO: 13:

     (i) SEQUENCE CHARACTERISTICS:
```

-continued

```
          (A) LENGTH: 141 base pairs
          (B) TYPE: nucleic acid
          (C) STRANDEDNESS: double
          (D) TOPOLOGY: linear

    (ii) MOLECULE TYPE: cDNA to mRNA

   (iii) HYPOTHETICAL: NO

   (iii) ANTI-SENSE: NO

   (vii) IMMEDIATE SOURCE:
          (B) CLONE: pGB/IL-304

    (ix) FEATURE:
          (A) NAME/KEY: CDS
          (B) LOCATION: 1..141

    (xi) SEQUENCE DESCRIPTION: SEQ ID NO: 13:

ATG ACC ATG ATT ACG AAT TTA ATA CGA CTC ACT ATA GGG AAT TCG AGC       48
Met Thr Met Ile Thr Asn Leu Ile Arg Leu Thr Ile Gly Asn Ser Ser
  1               5                  10                  15

TCG GTA CCC GGG GAT CCT CTA GAG TCG ATC GAC CCC ACG ACC CAG ACA       96
Ser Val Pro Gly Asp Pro Leu Glu Ser Ile Asp Pro Thr Thr Gln Thr
             20                  25                  30

ACG CCC CTG AAG ACA AGC TGG GTT AAC TGC TCT AAC ATG ATC GAT          141
Thr Pro Leu Lys Thr Ser Trp Val Asn Cys Ser Asn Met Ile Asp
         35                  40                  45


(2) INFORMATION FOR SEQ ID NO: 14:

     (i) SEQUENCE CHARACTERISTICS:
          (A) LENGTH: 47 amino acids
          (B) TYPE: amino acid
          (D) TOPOLOGY: linear

    (ii) MOLECULE TYPE: protein

    (xi) SEQUENCE DESCRIPTION: SEQ ID NO: 14:

Met Thr Met Ile Thr Asn Leu Ile Arg Leu Thr Ile Gly Asn Ser Ser
  1               5                  10                  15

Ser Val Pro Gly Asp Pro Leu Glu Ser Ile Asp Pro Thr Thr Gln Thr
             20                  25                  30

Thr Pro Leu Lys Thr Ser Trp Val Asn Cys Ser Asn Met Ile Asp
         35                  40                  45


(2) INFORMATION FOR SEQ ID NO: 15:

     (i) SEQUENCE CHARACTERISTICS:
          (A) LENGTH: 93 base pairs
          (B) TYPE: nucleic acid
          (C) STRANDEDNESS: double
          (D) TOPOLOGY: linear

    (ii) MOLECULE TYPE: cDNA to mRNA

   (iii) HYPOTHETICAL: NO

   (iii) ANTI-SENSE: NO

   (vii) IMMEDIATE SOURCE:
          (B) CLONE: pGB/IL-305

    (ix) FEATURE:
          (A) NAME/KEY: CDS
          (B) LOCATION: 1..93

    (xi) SEQUENCE DESCRIPTION: SEQ ID NO: 15:

ATG ACC ATG ATT ACG AAT TTA ATA CGA CTC ACT ATA GGG AAT TCG AGC       48
Met Thr Met Ile Thr Asn Leu Ile Arg Leu Thr Ile Gly Asn Ser Ser
```

-continued

```
  1               5                  10                  15

TCG GTA CCC GGG GAT CCT CTA GAG AAC TGC TCT AAC ATG ATC GAT            93
Ser Val Pro Gly Asp Pro Leu Glu Asn Cys Ser Asn Met Ile Asp
             20                  25                  30


(2) INFORMATION FOR SEQ ID NO: 16:

     (i) SEQUENCE CHARACTERISTICS:
          (A) LENGTH: 31 amino acids
          (B) TYPE: amino acid
          (D) TOPOLOGY: linear

    (ii) MOLECULE TYPE: protein

    (xi) SEQUENCE DESCRIPTION: SEQ ID NO: 16:

Met Thr Met Ile Thr Asn Leu Ile Arg Leu Thr Ile Gly Asn Ser Ser
  1               5                  10                  15

Ser Val Pro Gly Asp Pro Leu Glu Asn Cys Ser Asn Met Ile Asp
             20                  25                  30


(2) INFORMATION FOR SEQ ID NO: 17:

     (i) SEQUENCE CHARACTERISTICS:
          (A) LENGTH: 66 base pairs
          (B) TYPE: nucleic acid
          (C) STRANDEDNESS: double
          (D) TOPOLOGY: linear

    (ii) MOLECULE TYPE: cDNA to mRNA

   (iii) HYPOTHETICAL: NO

   (iii) ANTI-SENSE: NO

   (vii) IMMEDIATE SOURCE:
          (B) CLONE: pGB/IL-306

    (ix) FEATURE:
          (A) NAME/KEY: CDS
          (B) LOCATION: 1..66

    (xi) SEQUENCE DESCRIPTION: SEQ ID NO: 17:

ATG GCT CCC ATG ACC CAG ACA ACG CCC CCG AAG ACA AGC CGG GTT AAC        48
Met Ala Pro Met Thr Gln Thr Thr Pro Pro Lys Thr Ser Arg Val Asn
  1               5                  10                  15

TGC TCT AAC ATG ATC GAT                                                66
Cys Ser Asn Met Ile Asp
             20


(2) INFORMATION FOR SEQ ID NO: 18:

     (i) SEQUENCE CHARACTERISTICS:
          (A) LENGTH: 22 amino acids
          (B) TYPE: amino acid
          (D) TOPOLOGY: linear

    (ii) MOLECULE TYPE: protein

    (xi) SEQUENCE DESCRIPTION: SEQ ID NO: 18:

Met Ala Pro Met Thr Gln Thr Thr Pro Pro Lys Thr Ser Arg Val Asn
  1               5                  10                  15

Cys Ser Asn Met Ile Asp
             20


(2) INFORMATION FOR SEQ ID NO: 19:

     (i) SEQUENCE CHARACTERISTICS:
          (A) LENGTH: 37 amino acids
```

-continued (B) TYPE: amino acid
(D) TOPOLOGY: linear (ii) MOLECULE TYPE: peptide (iii) HYPOTHETICAL: NO (iii) ANTI-SENSE: NO (v) FRAGMENT TYPE: N-terminal (vii) IMMEDIATE SOURCE:
(B) CLONE: pGB/IL-307

(xi) SEQUENCE DESCRIPTION: SEQ ID NO: 19:

```
Met Ser Tyr Ala Val Cys Arg Met Glu Lys Val Lys Ser Gly Val Pro
1               5                   10                  15

Ser Ser Asn Ser Gly Pro Glu Gln Asp Arg Val Pro Pro Ala Asp Pro
            20                  25                  30

Asn Met Ser Arg Leu
        35
```

(2) INFORMATION FOR SEQ ID NO: 20:

(i) SEQUENCE CHARACTERISTICS:
(A) LENGTH: 41 base pairs
(B) TYPE: nucleic acid
(C) STRANDEDNESS: double
(D) TOPOLOGY: linear (ii) MOLECULE TYPE: DNA (synthetic)

(iii) HYPOTHETICAL: NO (iii) ANTI-SENSE: NO (vii) IMMEDIATE SOURCE:
(B) CLONE: pGB/IL-308

(ix) FEATURE:
(A) NAME/KEY: promoter
(B) LOCATION: 1..41

(xi) SEQUENCE DESCRIPTION: SEQ ID NO: 20:

```
GAATTCTTGA CAAAGCTTCT CGAGACTGAT ATAATGAGCT C                          41
```

(2) INFORMATION FOR SEQ ID NO: 21:

(i) SEQUENCE CHARACTERISTICS:
(A) LENGTH: 7336 base pairs
(B) TYPE: nucleic acid
(C) STRANDEDNESS: double
(D) TOPOLOGY: circular (ii) MOLECULE TYPE: DNA (plasmid)

(iii) HYPOTHETICAL: NO (iii) ANTI-SENSE: NO (vii) IMMEDIATE SOURCE:
(B) CLONE: pBHA1

(xi) SEQUENCE DESCRIPTION: SEQ ID NO: 21:

```
AATTCACCTC GAAAGCAAGC TGATAAACCG ATACAATTAA AGGCTCCTTT TGGAGCCTTT      60

TTTTTTGGAG ATTTTCAACG TGAAAAAATT ATTATTCGCA ATTCCAAGCT AATTCACCTC     120

GAAAGCAAGC TGATAAACCG ATACAATTAA AGGCTCCTTT TGGAGCCTTT TTTTTTGGAG     180

ATTTTCAACG TGAAAAAATT ATTATTCGCA ATTCCAAGCT CTGCCTCGCG CGTTTCGGTG     240
```

-continued

```
ATGACGGTGA AAACCTCTGA CACATGCAGC TCCCGGAGAC GGTCACAGCT TGTCTGTAAG    300
CGGATGCAGA TCACGCGCCC TGTAGCGGCG CATTAAGCGC GGCGGGTGTG GTGGTTACGC    360
GCAGCGTGAC CGCTACACTT GCCAGCGCCC TAGCGCCCGC TCCTTTCGCT TTCTTCCCTT    420
CCTTTCTCGC CACGTTCGCC GGCTTTCCCC GTCAAGCTCT AAATCGGGGG CTCCCTTTAG    480
GGTTCCGATT TAGTGCTTTA CGGCACCTCG ACCCCAAAAA ACTTGATTAG GGTGATGGTT    540
CACGTAGTGG GCCATCGCCC TGATAGACGG TTTTTCGCCC TTTGACGTTG GAGTCCACGT    600
TCTTTAATAG TGGACTCTTG TTCCAAACTG GAACAACACT CAACCCTATC TCGGTCTATT    660
CTTTTGATTT ATAAGGGATT TTGCCGATTT CGGCCTATTG GTTAAAAAAT GAGCTGATTT    720
AACAAAAATT TAACGCGAAT TTTAACAAAA TATTAACGTT TACAATTTGA TCTGCGCTCG    780
GTCGTTCGGC TGCGGCGAGC GGTATCAGCT CACTCAAAGG CGGTAATACG GTTATCCACA    840
GAATCAGGGG ATAACGCAGG AAAGAACATG TGAGCAAAAG GCCAGCAAAA GGCCAGGAAC    900
CGTAAAAAGG CCGCGTTGCT GGCGTTTTTC CATAGGCTCC GCCCCCCTGA CGAGCATCAC    960
AAAAATCGAC GCTCAAGTCA GAGGTGGCGA AACCCGACAG GACTATAAAG ATACCAGGCG   1020
TTTCCCCCTG GAAGCTCCCT CGTGCGCTCT CCTGTTCCGA CCCTGCCGCT TACCGGATAC   1080
CTGTCCGCCT TTCTCCCTTC GGGAAGCGTG GCGCTTTCTC AATGCTCACG CTGTAGGTAT   1140
CTCAGTTCGG TGTAGGTCGT TCGCTCCAAG CTGGGCTGTG TGCACGAACC CCCCGTTCAG   1200
CCCGACCGCT GCGCCTTATC CGGTAACTAT CGTCTTGAGT CCAACCCGGT AAGACACGAC   1260
TTATCGCCAC TGGCAGCAGC CACTGGTAAC AGGATTAGCA GAGCGAGGTA TGTAGGCGGT   1320
GCTACAGAGT TCTTGAAGTG GTGGCCTAAC TACGGCTACA CTAGAAGGAC AGTATTTGGT   1380
ATCTGCGCTC TGCTGAAGCC AGTTACCTTC GGAAAAAGAG TTGGTAGCTC TTGATCCGGC   1440
AAACAAACCA CCGCTGGTAG CGGTGGTTTT TTTGTTTGCA AGCAGCAGAT TACGCGCAGA   1500
AAAAAAGGAT CTCAAGAAGA TCCTTTGATC TTTTCTACGG GGTCTGACGC TCAGTGGAAC   1560
GAAAACTCAC GTTAAGGGAT TTTGGTCATG AGATTATCAA AAAGGATCTT CACCTAGATC   1620
CTTTTAAATT AAAAATGAAG TTTTAAATCA ATCTAAAGTA TATATGAGTA AACTTGGTCT   1680
GACAGTTACC AATGCTTAAT CAGTGAGGCA CCTATCTCAG CGATCTGTCT ATTTCGTTCA   1740
TCCATAGTTG CCTGACTCCC CGTCGTGTAG ATAACTACGA TACGGGAGGG CTTACCATCT   1800
GGCCCCAGTG CTGCAATGAT ACCGCGAGAC CCACGCTCAC CGGCTCCAGA TTTATCAGCA   1860
ATAAACCAGC CAGCCGGAAG GGCCGAGCGC AGAAGTGGTC CTGCAACTTT ATCCGCCTCC   1920
ATCCAGTCTA TTAATTGTTG CCGGGAAGCT AGAGTAAGTA GTTCGCCAGT TAATAGTTTG   1980
CGCAACGTTG TTGCCATTGC TGCAGGCATC GTGGTGTCAC GCTCGTCGTT TGGTATGGCT   2040
TCATTCAGCT CCGGTTCCCA ACGATCAAGG CGAGTTACAT GATCCCCCAT GTTGTGCAAA   2100
AAAGCGGTTA GCTCCTTCGG TCCTCCGATC GTTGTCAGAA GTAAGTTGGC CGCAGTGTTA   2160
TCACTCATGG TTATGGCAGC ACTGCATAAT TCTCTTACTG TCATGCCATC CGTAAGATGC   2220
TTTTCTGTGA CTGGTGAGTA CTCAACCAAG TCATTCTGAG AATAGTGTAT GCGGCGACCG   2280
AGTTGCTCTT GCCCGGCGTC AACACGGGAT AATACCGCGC CACATAGCAG AACTTTAAAA   2340
GTGCTCATCA TTGGAAAACG TTCTTCGGGG CGAAAACTCT CAAGGATCTT ACCGCTGTTG   2400
AGATCCAGTT CGATGTAACC CACTCGTGCA CCCAACTGAT CTTCAGCATC TTTTACTTTC   2460
ACCAGCGTTT CTGGGTGAGC AAAAACAGGA AGGCAAAATG CCGCAAAAAA GGGAATAAGG   2520
GCGACACGGA AATGTTGAAT ACTCATACTC TTCCTTTTTC AATATTATTG AAGCAGACAG   2580
TTTTATTGTT CATGATGATA TATTTTTATC TTGTGCAATG TAACATCAGA GATTTTGAGA   2640
```

-continued

CACAACGTGG CTTTGTTGAA TAAATCGAAC TTTTGCTGAG TTGACTCCCC GCGCGCGATG 2700

GGTCGAATTT GCTTTCGAAA AAAAAGCCCG CTCATTAGGC GGGCTAAAAA AAAGCCCGCT 2760

CATTAGGCGG GCTCGAATTT CTGCCATTCA TCCGCTTATT ATCACTTATT CAGGCGTAGC 2820

AACCAGGCGT TTAAGGGCAC CAATAACTGC CTTAAAAAAA TTACGCCCCG CCCTGCCACT 2880

CATCGCAGTA CTGTTGTAAT TCATTAAGCA TTCTGCCGAC ATGGAAGCCA TCACAGACGG 2940

CATGATGAAC CTGAATCGCC AGCGGCATCA GCACCTTGTC GCCTTGCGTA TAATATTTGC 3000

CCATAGTGAA AACGGGGGCG AAGAAGTTGT CCATATTCGC CACGTTTAAA TCAAAACTGG 3060

TGAAACTCAC CCAGGGATTG GCTGAGACGA AAAACATATT CTCAATAAAC CCTTTAGGGA 3120

AATAGGCCAG GTTTTCACCG TAACACGCCA CATCTTGCGA ATATATGTGT AGAAACTGCC 3180

GGAAATCGTC GTGGTATTCA CTCCAGAGCG ATGAAAACGT TTCAGTTTGC TCATGGAAAA 3240

CGGTGTAACA AGGGTGAACA CTATCCCATA TCACCAGCTC ACCGTCTTTC ATTGCCATAC 3300

GAAATTCCGG ATGAGCATTC ATCAGGCGGG CAAGAATGTG AATAAAGGCC GGATAAAACT 3360

TGTGCTTATT TTTCTTTACG GTCTTTAAAA AGGCCGTAAT ATCCAGCTAA ACGGTCTGGT 3420

TATAGGTACA TTGAGCAACT GACTGAAATG CCTCAAAATG TTCTTTACGA TGCCATTGGG 3480

ATATATCAAC GGTGGTATAT CCAGTGATTT TTTTCTCCAT TTTAGCTTCC TTAGCTCCTG 3540

AAAATCTCGA TAACTCAAAA AATACGCCCG GTAGTGATCT TATTTCATTA TGGTGAAAGT 3600

TGGAACCTCT TACGTGCCGA TCAACGTCTC ATTTTCGCCA AAAGTTGGCC CAGGGCTTCC 3660

CGGTATCAAC AGGGACACCA GGATTTATTT ATTCTGCGAA GTGATCTTCC GTCACAGGTA 3720

TTTATTCGAA GACGAAAGGG CATCGCGCGC GGGGAATTCC CGGGAGAGCT CGATATCGCA 3780

TGCGGTACCT CTAGAAGAAG CTTGGAGACA AGGTAAAGGA TAAAACAGCA CAATTCCAAG 3840

AAAAACACGA TTTAGAACCT AAAAAGAACG AATTTGAACT AACTCATAAC CGAGAGGTAA 3900

AAAAAGAACG AAGTCGAGAT CAGGGAATGA GTTTATAAAA TAAAAAAAGC ACCTGAAAAG 3960

GTGTCTTTTT TTGATGGTTT TGAACTTGTT CTTTCTTATC TTGATACATA TAGAAATAAC 4020

GTCATTTTTA TTTTAGTTGC TGAAAGGTGC GTTGAAGTGT TGGTATGTAT GTGTTTTAAA 4080

GTATTGAAAA CCCTTAAAAT TGGTTGCACA GAAAAACCCC ATCTGTTAAA GTTATAAGTG 4140

ACTAAACAAA TAACTAAATA GATGGGGGTT TCTTTTAATA TTATGTGTCC TAATAGTAGC 4200

ATTTATTCAG ATGAAAAATC AAGGGTTTTA GTGGACAAGA CAAAAAGTGG AAAAGTGAGA 4260

CCATGGAGAG AAAAGAAAAT CGCTAATGTT GATTACTTTG AACTTCTGCA TATTCTTGAA 4320

TTTAAAAAGG CTGAAAGAGT AAAAGATTGT GCTGAAATAT TAGAGTATAA ACAAAATCGT 4380

GAAACAGGCG AAAGAAAGTT GTATCGAGTG TGGTTTTGTA AATCCAGGCT TTGTCCAATG 4440

TGCAACTGGA GGAGAGCAAT GAAACATGGC ATTCAGTCAC AAAAGGTTGT TGCTGAAGTT 4500

ATTAAACAAA AGCCAACAGT TCGTTGGTTG TTTCTCACAT TAACAGTTAA AAATGTTTAT 4560

GATGGCGAAG AATTAAATAA GAGTTTGTCA GATATGGCTC AAGGATTTCG CCGAATGATG 4620

CAATATAAAA AAATTAATAA AAATCTTGTT GGTTTTATGC GTGCAACGGA AGTGACAATA 4680

AATAATAAAG ATAATTCTTA TAATCAGCAC ATGCATGTAT TGGTATGTGT GGAACCAACT 4740

TATTTTAAGA ATACAGAAAA CTACGTGAAT CAAAAACAAT GGATTCAATT TTGGAAAAAG 4800

GCAATGAAAT TAGACTATGA TCCAAATGTA AAAGTTCAAA TGATTCGACC GAAAAATAAA 4860

TATAAATCGG ATATACAATC GGCAATTGAC GAAACTGCAA AATATCCTGT AAAGGATACG 4920

GATTTTATGA CCGATGATGA AGAAAAGAAT TTGAAACGTT TGTCTGATTT GGAGGAAGGT 4980

-continued

```
TTACACCGTA AAAGGTTAAT CTCCTATGGT GGTTTGTTAA AAGAAATACA TAAAAAATTA   5040

AACCTTGATG ACACAGAAGA AGGCGATTTG ATTCATACAG ATGATGACGA AAAAGCCGAT   5100

GAAGATGGAT TTTCTATTAT TGCAATGTGG AATTGGGAAC GGAAAAATTA TTTTATTAAA   5160

GAGTAGTTCA ACAAACGGGC CAGTTTGTTG AAGATTAGAT GCTATAATTG TTATTAAAAG   5220

GATTGAAGGA TGCTTAGGAA GACGAGTTAT TAATAGCTGA ATAAGAACGG TGCTCTCCAA   5280

ATATTCTTAT TTAGAAAAGC AAATCTAAAA TTATCTGAAA AGGGAATGAG AATAGTGAAT   5340

GGACCAATAA TAATGACTAG AGAAGAAAGA ATGAAGATTG TTCATGAAAT TAAGGAACGA   5400

ATATTGGATA AATATGGGGA TGATGTTAAG GCTATTGGTG TTTATGGCTC TCTTGGTCGT   5460

CAGACTGATG GGCCCTATTC GGATATTGAG ATGATGTGTG TCATGTCAAC AGAGGAAGCA   5520

GAGTTCAGCC ATGAATGGAC AACCGGTGAG TGGAAGGTGG AAGTGAATTT TGATAGCGAA   5580

GAGATTCTAC TAGATTATGC ATCTCAGGTG GAATCAGATT GGCCGCTTAC ACATGGTCAA   5640

TTTTTCTCTA TTTTGCCGAT TTATGATTCA GGTGGATACT TAGAGAAAGT GTATCAAACT   5700

GCTAAATCGG TAGAAGCCCA AACGTTCCAC GATGCGATTT GTGCCCTTAT CGTAGAAGAG   5760

CTGTTTGAAT ATGCAGGCAA ATGGCGTAAT ATTCGTGTGC AAGGACCGAC AACATTTCTA   5820

CCATCCTTGA CTGTACAGGT AGCAATGGCA GGTGCCATGT TGATTGGTCT GCATCATCGC   5880

ATCTGTTATA CGACGAGCGC TTCGGTCTTA ACTGAAGCAG TTAAGCAATC AGATCTTCCT   5940

TCAGGTTATG ACCATCTGTG CCAGTTCGTA ATGTCTGGTC AACTTTCCGA CTCTGAGAAA   6000

CTTCTGGAAT CGCTAGAGAA TTTCTGGAAT GGGATTCAGG AGTGGACAGA ACGACACGGA   6060

TATATAGTGG ATGTGTCAAA ACGCATACCA TTTTGAACGA TGACCTCTAA TAATTGTTAA   6120

TCATGTTGGT TACGTATTTA TTAACTTCTC CTAGTATTAG TAATTATCAT GGCTGTCATG   6180

GCGCATTAAC GGAATAAAGG GTGTGCTTAA ATCGGGCCAT TTTGCGTAAT AAGAAAAAGG   6240

ATTAATTATG AGCGAATTGA ATTAATAATA AGGTAATAGA TTTACATTAG AAAATGAAAG   6300

GGGATTTTAT GCGTGAGAAT GTTACAGTCT ATCCCGGCAT TGCCAGTCGG GGATATTAAA   6360

AAGAGTATAG GTTTTTATTG CGATAAACTA GGTTTCACTT TGGTTCACCA TGAAGATGGA   6420

TTCGCAGTTC TAATGTGTAA TGAGGTTCGG ATTCATCTAT GGGAGGCAAG TGATGAAGGC   6480

TGGCGCTCTC GTAGTAATGA TTCACCGGTT TGTACAGGTG CGGAGTCGTT TATTGCTGGT   6540

ACTGCTAGTT GCCGCATTGA AGTAGAGGGA ATTGATGAAT TATATCAACA TATTAAGCCT   6600

TTGGGCATTT TGCACCCCAA TACATCATTA AAAGATCAGT GGTGGGATGA ACGAGACTTT   6660

GCAGTAATTG ATCCCGACAA CAATTTGATT AGCTTTTTTC AACAAATAAA AAGCTAAAAT   6720

CTATTATTAA TCTGTTCAGC AATCGGGCGC GATTGCTGAA TAAAAGATAC GAGAGACCTC   6780

TCTTGTATCT TTTTTATTTT GAGTGGTTTT GTCCGTTACA CTAGAAAACC GAAAGACAAT   6840

AAAAATTTTA TTCTTGCTGA GTCTGGCTTT CGGTAAGCTA GACAAAACGG ACAAAATAAA   6900

AATTGGCAAG GGTTTAAAGG TGGAGATTTT TTGAGTGATC TTCTCAAAAA ATACTACCTG   6960

TCCCTTGCTG ATTTTTAAAC GAGCACGAGA GCAAAACCCC CCTTTGCTGA GGTGGCAGAG   7020

GGCAGGTTTT TTTGTTTCTT TTTTCTCGTA AAAAAAAGAA AGGTCTTAAA GGTTTTATGG   7080

TTTTGGTCGG CACTGCCGAC AGCCTCGCAG GACACACACT TTATGAATAT AAAGTATAGT   7140

GTGTTATACT TTACTTGGAA GTGGTTGCCG GAAAGAGCGA AATGCCTCA CATTTGTGCC   7200

ACCTAAAAAG GAGCGATTTA CATATGAGTT ATGCAGTTTG TAGAATGCAA AAAGTGAAAT   7260

CAGGGGGATC CTCTAGAGTC GAGCTCAAGC TAGCTTGGTA CGTACCAGAT CTGAGATCAC   7320

GCGTTCTAGA GGTCGA                                                   7336
```

```
(2) INFORMATION FOR SEQ ID NO: 22:

     (i) SEQUENCE CHARACTERISTICS:
          (A) LENGTH: 90 base pairs
          (B) TYPE: nucleic acid
          (C) STRANDEDNESS: double
          (D) TOPOLOGY: linear

    (ii) MOLECULE TYPE: cDNA to mRNA

   (iii) HYPOTHETICAL: NO

   (iii) ANTI-SENSE: NO

   (vii) IMMEDIATE SOURCE:
          (B) CLONE: pGB/IL-313

    (ix) FEATURE:
          (A) NAME/KEY: CDS
          (B) LOCATION: 18..80

    (ix) FEATURE:
          (A) NAME/KEY: misc_feature
          (B) LOCATION: 88
          (C) IDENTIFICATION METHOD: experimental
          (D) OTHER INFORMATION: /product= "Human interleukin-3"
               /evidence= EXPERIMENTAL
               /note= "This ATG codon encodes the first amino
               acid of pre-IL3"

    (xi) SEQUENCE DESCRIPTION: SEQ ID NO: 22:

AAAGGAGCGA TTTACAT ATG AGT TAT GCA GTT TGT AGA ATG CAA AAA GTG        50
                   Met Ser Tyr Ala Val Cys Arg Met Gln Lys Val
                     1               5                  10

AAA TCA GGG GGA TCC AAG GAG GTG ATC TAGAGTCGAC ATG                    90
Lys Ser Gly Gly Ser Lys Glu Val Ile
             15                  20


(2) INFORMATION FOR SEQ ID NO: 23:

     (i) SEQUENCE CHARACTERISTICS:
          (A) LENGTH: 20 amino acids
          (B) TYPE: amino acid
          (D) TOPOLOGY: linear

    (ii) MOLECULE TYPE: protein

    (xi) SEQUENCE DESCRIPTION: SEQ ID NO: 23:

Met Ser Tyr Ala Val Cys Arg Met Gln Lys Val Lys Ser Gly Gly Ser
  1               5                  10                  15

Lys Glu Val Ile
             20


(2) INFORMATION FOR SEQ ID NO: 24:

     (i) SEQUENCE CHARACTERISTICS:
          (A) LENGTH: 38 base pairs
          (B) TYPE: nucleic acid
          (C) STRANDEDNESS: double
          (D) TOPOLOGY: linear

    (ii) MOLECULE TYPE: DNA (genomic)

   (iii) HYPOTHETICAL: NO

   (iii) ANTI-SENSE: NO

   (vii) IMMEDIATE SOURCE:
          (B) CLONE: pGB/IL-317

    (xi) SEQUENCE DESCRIPTION: SEQ ID NO: 24:
```

-continued

CTGCAGCGGC GGCAGAATTC GCGGCCGCCC GGGTCGAC 38

(2) INFORMATION FOR SEQ ID NO: 25:

(i) SEQUENCE CHARACTERISTICS:
(A) LENGTH: 2748 base pairs
(B) TYPE: nucleic acid
(C) STRANDEDNESS: double
(D) TOPOLOGY: linear (ii) MOLECULE TYPE: DNA (genomic)

(iii) HYPOTHETICAL: NO (iii) ANTI-SENSE: NO (vii) IMMEDIATE SOURCE:
(B) CLONE: pGB/IL-316

(xi) SEQUENCE DESCRIPTION: SEQ ID NO: 25:

CCGCGGGGAT CGACTCATAA AATAGTAACC TTCTAATGCG TATCTATTGA CTACCAACCA 60

TTAGTGTGGT TGCAGAAGGC GGAATTCTCC CTTCTTCGAA TTCAGCTTGC TTTTCATTTT 120

TATTTTCCAT TTTTCAGTTT TTGTTTGTGT CGAATTTAGC CAGTTGCTTC TCCAAGATGA 180

AAAAACCCCT GCGCAGTTTC TGTGTCGCAA GATCCTAATC GACTTTTCCA CCCCCCACAA 240

AAGTAAATGT TTCTTTGTTA CATTCGCGTG GGTAGCTAGC TCCCCGAATC TCAAAGGACT 300

TAGGGACTGC ACTACATCAG AGTGTGTTCA CCTGGTTTGC TGCCTGGTTT GAAAGAAAAG 360

AGCGGGAACT CGCGGGTTCC CGGCGAATAA TCATGCGATA GTCCTTTGGC CTTCCAAGTC 420

GCATGTAGAG TAGACAACAG ACAGGGAGGG CAGGAAGGAT CTTTCACTGA GATCCTGTAT 480

CTTGTTGGGT AAGTCGGATG AAAGGGGAAT CGTATGAGAT TGGAGAGGAT GCGGAAGAGG 540

TAACGCCTTT TGTTAACTTG TTTAATTATT ATGGGGCAGG CGAGAGGGGG AGGAATGTAT 600

GTGTGTGAGG CGGGCGAGAC GGAGCCATCC AGGCCAGGTA GAAATAGAGA AAGCCGAATG 660

TTAGACAATA TGGCAGCGTA GTAGAGTAGG TAGGTAGGCA AGTACTGCTA GCAAAGAGGA 720

GAAGGGTAAG CTCACTCTTC GCATTCCACA CCGTTAGTGT GTCAGTTTAG ACAAAAAAAC 780

AACTACTATA CCAATTAGTA GACTGTGAAC TGACTTTTGG AACGGCTTTT CGGACTGCGA 840

TTATTCGTGA GGAATCAAGG TAGGAATTTG GTCATATTTA CGGACAACAG TGGGTGATTC 900

CCATATGGAG TAGGAAAACG AGATCATGGT ATCCTCAGAT ATGTTGCGGA ATTCTGTTCA 960

CCGCAAAGTT CAGGGTGCTC TGGTGGGTTT CGGTTGGTCT TTGCTTTGCT TCTCCCTTGT 1020

CTTGCATGTT AATAATAGCC TAGCCTGTGA GCCGAAACTT AGGGTAGGCT TAGTGTTGGA 1080

ACGTACATAT GTATCACGTT GACTTGGTTT AACCAGGCGA CCTGGTAGCC AGCCATACCC 1140

ACACACGTTT TTTGTATTCT TCAGTATAGT TGTGAAAAGT GTAGCGGAAA TATGTGGTCC 1200

GAGCAACAGC GTCTTTTTCT AGTAGTGCGG TCGGTTACTT GGTTGACATT GGTATTTGGA 1260

CTTTGTTGCT ACACCATTCA CTACTTGAAG TCGAGTGTGA AGGGTATGAT TTCTAGTGGT 1320

GAACACCTTT AGTTACGTAA TGTTTTCATT GCTGTTTTAC TTGAGATTTC GATTGAGAAA 1380

AAGGTATTTA ATAGCTCGAA TCAATGTGTT ATCATTGTGA AGATGTTCTT CCCTAACTCG 1440

AAAGGTATAT GAGGCTTGTG TTTCTTAGGA GAATTATTAT TCTTTTGTTA TGTTGCGCTT 1500

GTAGTTGGAA AAGGTGAAGA GACAAAAGCT TAACACTTGA AATTTAGGAA AGAGCAGAAT 1560

TTGGCAAAAA AAATAAAAAA AAAATAAACA CGTCGACTTG TGAGCGGATA ACAATCGACA 1620

CATACTCATC GAGAACTGAA AGATATGAGA TTTCCATCGA TTTTTACTGC AGTTTTATTC 1680

-continued

```
GCAGCATCCT CCGCATTAGC TGCTCCAGTC AACACTACAA CAGAAGATGA AACGGCACAA   1740

ATTCCGGCTG AAGCTGTCAT CGGTTACTTA GATTTAGAAG GGGATTTCGA TGTTGCTGTT   1800

TTGCCATTTT CCAACAGCAC AAATAACGGG TTATTGTTTA TAAATACTAC TATTGCCAGC   1860

ATTGCTGCTA AAGAAGAAGG GGTATCTCTA GATAAAAGAG CTCCCATGAC CCAGACAACG   1920

CCCTTGAAGA CAAGCTGGGT TAACTGCTCT AACATGATCG ATGAAATTAT AACACACTTA   1980

AAGCAGCCAC CTTTGCCTTT GCTGGACTTC AACAACCTCA ATGGGGAAGA CCAAGACATT   2040

CTGATGGAAA ATAACCTTCG AAGGCCAAAC CTGGAGGCAT TCAACAGGGC TGTCAAGAGT   2100

TTACAGAACG CATCAGCAAT TGAGAGCATT CTTAAAAATC TCCTGCCATG TCTGCCCCTG   2160

GCCACGGCCG CACCCACGCG ACATCCAATC CATATCAAGG ACGGTGACTG GAATGAATTC   2220

CGGAGGAAAC TGACGTTCTA TCTGAAAACC CTTGAGAATG CGCAGGCTCA ACAGACGACT   2280

TTGAGCCTCG CGATCTTTTG AGTCCAACGT CCAGCTCGTT CTCTGGGCCT TCTCACCACA   2340

GAGCCTCGGG ACATCAAAAA CAGCAGAACT TCTGAAACCT CTGGGTCATC TCTCACACAT   2400

TCCAGGACCA GAAGCATTTC ACCTTTTCCT GCGGCATCAG ATGAATTGTT AATTATCTAA   2460

TTTCTGAAAT GTGCAGCTCC CATTTGGCCT TGTGCGGTTG TGTTCTCATT TTTATCCCAT   2520

TGAGACTATT TATTTATGTA TGTATGTATT TATTTATTTA TTGCCTGGAG TGTGAACTGT   2580

ATTTATTTTA GCAGAGGAGC CATGTCCTGC TGCTTCTGCA AAAAACTCAG AGTGGGGTGG   2640

GGAGCATGTT CATTTGTACC TCGAGAATTT ATACTTAGAT AAGTATGTAC TTACAGGTAT   2700

ATTTCTATGA GATACTGATG TATACATGCA TGATAATATT TAAAGCTT                2748
```

(2) INFORMATION FOR SEQ ID NO: 26:

(i) SEQUENCE CHARACTERISTICS:
(A) LENGTH: 2734 base pairs
(B) TYPE: nucleic acid
(C) STRANDEDNESS: double
(D) TOPOLOGY: linear (ii) MOLECULE TYPE: DNA (genomic)

(iii) HYPOTHETICAL: NO (iii) ANTI-SENSE: NO (vii) IMMEDIATE SOURCE:
(B) CLONE: pGB/IL-318

(xi) SEQUENCE DESCRIPTION: SEQ ID NO: 26:

```
CCGCGGGGAT CGACTCATAA AATAGTAACC TTCTAATGCG TATCTATTGA CTACCAACCA     60

TTAGTGTGGT TGCAGAAGGC GGAATTCTCC CTTCTTCGAA TTCAGCTTGC TTTTCATTTT    120

TATTTTCCAT TTTTCAGTTT TTGTTTGTGT CGAATTTAGC CAGTTGCTTC TCCAAGATGA    180

AAAAACCCCT GCGCAGTTTC TGTGTCGCAA GATCCTAATC GACTTTTCCA CCCCCCACAA    240

AAGTAAATGT TTCTTTGTTA CATTCGCGTG GGTAGCTAGC TCCCCGAATC TCAAAGGACT    300

TAGGGACTGC ACTACATCAG AGTGTGTTCA CCTGGTTTGC TGCCTGGTTT GAAAGAAAAG    360

AGCGGGAACT CGCGGGTTCC CGGCGAATAA TCATGCGATA GTCCTTTGGC CTTCCAAGTC    420

GCATGTAGAG TAGACAACAG ACAGGGAGGG CAGGAAGGAT CTTTCACTGA GATCCTGTAT    480

CTTGTTGGGT AAGTCGGATG AAAGGGGAAT CGTATGAGAT TGGAGAGGAT GCGGAAGAGG    540

TAACGCCTTT TGTTAACTTG TTTAATTATT ATGGGGCAGG CGAGAGGGGG AGGAATGTAT    600

GTGTGTGAGG CGGGCGAGAC GGAGCCATCC AGGCCAGGTA GAAATAGAGA AAGCCGAATG    660

TTAGACAATA TGGCAGCGTA GTAGAGTAGG TAGGTAGGCA AGTACTGCTA GCAAAGAGGA    720
```

-continued

```
GAAGGGTAAG CTCACTCTTC GCATTCCACA CCGTTAGTGT GTCAGTTTAG ACAAAAAAAC    780

AACTACTATA CCAATTAGTA GACTGTGAAC TGACTTTTGG AACGGCTTTT CGGACTGCGA    840

TTATTCGTGA GGAATCAAGG TAGGAATTTG GTCATATTTA CGGACAACAG TGGGTGATTC    900

CCATATGGAG TAGGAAAACG AGATCATGGT ATCCTCAGAT ATGTTGCGGA ATTCTGTTCA    960

CCGCAAAGTT CAGGGTGCTC TGGTGGGTTT CGGTTGGTCT TTGCTTTGCT TCTCCCTTGT   1020

CTTGCATGTT AATAATAGCC TAGCCTGTGA GCCGAAACTT AGGGTAGGCT TAGTGTTGGA   1080

ACGTACATAT GTATCACGTT GACTTGGTTT AACCAGGCGA CCTGGTAGCC AGCCATACCC   1140

ACACACGTTT TTTGTATTCT TCAGTATAGT TGTGAAAAGT GTAGCGGAAA TATGTGGTCC   1200

GAGCAACAGC GTCTTTTTCT AGTAGTGCGG TCGGTTACTT GGTTGACATT GGTATTTGGA   1260

CTTTGTTGCT ACACCATTCA CTACTTGAAG TCGAGTGTGA AGGGTATGAT TTCTAGTGGT   1320

GAACACCTTT AGTTACGTAA TGTTTTCATT GCTGTTTTAC TTGAGATTTC GATTGAGAAA   1380

AAGGTATTTA ATAGCTCGAA TCAATGTGTT ATCATTGTGA AGATGTTCTT CCCTAACTCG   1440

AAAGGTATAT GAGGCTTGTG TTTCTTAGGA GAATTATTAT TCTTTTGTTA TGTTGCGCTT   1500

GTAGTTGGAA AAGGTGAAGA GACAAAAGCT TAACACTTGA AATTTAGGAA AGAGCAGAAT   1560

TTGGCAAAAA AAATAAAAAA AAAATAAACA CGTCGACTTG TGAGCGGATA ACACTCGAGG   1620

GATCTTCATT ATGAAATTCT CTACTATATT AGCCGCATCT ACTGCTTTAA TTTCCGTTGT   1680

TATGGCTGCT CCAGTTTCTA CCGAAACTGA CATCGACGAT CTTCCAATTT CGGTTCCAGA   1740

AGAAGCCTTG ATTGGATTCA TTGACTTAAC CGGGGATGAA GTTTCCTTGT TGCCTGTTAA   1800

TAACGGAACC CACACTGGTA TTCTATTCTT AAACACCACC ATCGCTGAAG CTGCTTTCGC   1860

TGACAAGGAT GATTTGAAGA AGCGCGCTCC CATGACCCAG ACAACGCCCT TGAAGACAAG   1920

CTGGGTTAAC TGCTCTAACA TGATCGATGA AATTATAACA CACTTAAAGC AGCCACCTTT   1980

GCCTTTGCTG GACTTCAACA ACCTCAATGG GGAAGACCAA GACATTCTGA TGGAAAATAA   2040

CCTTCGAAGG CCAAACCTGG AGGCATTCAA CAGGGCTGTC AAGAGTTTAC AGAACGCATC   2100

AGCAATTGAG AGCATTCTTA AAAATCTCCT GCCATGTCTG CCCCTGGCCA CGGCCGCACC   2160

CACGCGACAT CCAATCCATA TCAAGGACGG TGACTGGAAT GAATTCCGGA GGAAACTGAC   2220

GTTCTATCTG AAAACCCTTG AGAATGCGCA GGCTCAACAG ACGACTTTGA GCCTCGCGAT   2280

CTTTTGAGTC CAACGTCCAG CTCGTTCTCT GGGCCTTCTC ACCACAGAGC CTCGGGACAT   2340

CAAAAACAGC AGAACTTCTG AAACCTCTGG GTCATCTCTC ACACATTCCA GGACCAGAAG   2400

CATTTCACCT TTTCCTGCGG CATCAGATGA ATTGTTAATT ATCTAATTTC TGAAATGTGC   2460

AGCTCCCATT TGGCCTTGTG CGGTTGTGTT CTCATTTTTA TCCCATTGAG ACTATTTATT   2520

TATGTATGTA TGTATTTATT TATTTATTGC CTGGAGTGTG AACTGTATTT ATTTTAGCAG   2580

AGGAGCCATG TCCTGCTGCT TCTGCAAAAA ACTCAGAGTG GGGTGGGGAG CATGTTCATT   2640

TGTACCTCGA GAATTTATAC TTAGATAAGT ATGTACTTAC AGGTATATTT CTATGAGATA   2700

CTGATGTATA CATGCATGAT AATATTTAAA GCTT                                2734
```

(2) INFORMATION FOR SEQ ID NO: 27:

(i) SEQUENCE CHARACTERISTICS:
(A) LENGTH: 1113 base pairs
(B) TYPE: nucleic acid
(C) STRANDEDNESS: double
(D) TOPOLOGY: linear (ii) MOLECULE TYPE: DNA (genomic)

-continued (iii) HYPOTHETICAL: NO (iii) ANTI-SENSE: NO (vii) IMMEDIATE SOURCE:
(B) CLONE: pGB/TEFact (xi) SEQUENCE DESCRIPTION: SEQ ID NO: 27:

```
TCGAATTTGC GGGGAGAAGA TGGATCTATG CTAAATCTAA ATAGGCATTT GAAAAACGAC     60

GACGAGTTAC ACGACATATC GCCATCTTTA AATGAGCAAC CACACTGGGA CCTCATAGAG    120

GACGGGTCTC GCTGGAGTAA ATTTTTCAAC GGGATAATTA AGACGACAAG AAGGTTCACG    180

AAATCTTTAA TGAGGTCTTT AGTCAGAGGC AGGAACAGCC GTCAAGGGGG CATAAGACTA    240

CGGTCATCCC CATCTGCCTC TTCGTCCAGC CTTGCCAACA GGGAGTTCTT CAGAGACATG    300

GAGGCTCAAA ACGAAATTAT TGACAGCCTA GACATCAATA GTCATACAAC AGAAAGCGAC    360

CACCCAACTT TGGCTGATAA TAGCGTATAA ACAATGCATA CTTTGTACGT TCAAAATACA    420

ATGCAGTAGA TATATTTATG CATATTACAT ATAATACATA TCACATAGGA AGCAACAGGC    480

GCGTTGGACT TTTAATTTTC GAGGACCGCG AATCCTTACA TCACACCCAA TCCCCCACAA    540

GTGATCCCCC ACACACCATA GCTTCAAAAT GTTTCTACTC CTTTTTTACT CTTCCAGATT    600

TTCTCGGACT CCGCGCATCG CCGTACCACT TCAAAACACC CAAGCACAGC ATACTAAATT    660

TCCCCTCTTT CTTCCTCTAG GGTGTCGTTA ATTACCCGTA CTAAAGGTTT GGAAAAGAAA    720

AAAGAGACCG CCTCGTTTCT TTTTCTTCGT CGAAAAAGGC AATAAAAATT TTTATCACGT    780

TTCTTTTTCT TGAAAATTTT TTTTTTTGAT TTTTTTCTCT TTCGATGACC TCCCATTGAT    840

ATTTAAGTTA ATAAACGGTC TTCAATTTCT CAAGTTTCAG TTTCATTTTT CTTGTTCTAT    900

TACAACTTTT TTTACTTCTT GCTCATTAGA AAGAAAGCAT AGCAATCTAG TCGACAGATC    960

TCTCGAGTGC TTTTGTGCGC GTATGTTTAT GTATGTACCT CTCTCTCTAT TTCTATTTTT   1020

AAACCACCCT CTCAATAAAA TAAAAATAAT AAAGTATTTT TAAGGAAAAG ACGTGTTTAA   1080

GCACTGACTT TATCTACTTT TTGTACGTCT AGA                                1113
```